(12) United States Patent
Kriheli et al.

(10) Patent No.: US 12,064,584 B1
(45) Date of Patent: Aug. 20, 2024

(54) TAMPER PROOF LUER LOCK CONNECTOR AND A VALVE ARRANGEMENT FOR AN ADAPTOR

(71) Applicant: EQUASHIELD MEDICAL LTD., Migdal Tefen (IL)

(72) Inventors: Marino Kriheli, Savion (IL); Raanan Tavor, Yuvalim (IL); Eric Shem-Tov, Ramat Hasharon (IL); Shlomi Dach, Qiryat Yam (IL)

(73) Assignee: Equashield Medical Ltd, Migdal Telen (IL)

( * ) Notice: Subject to any disclaimer, the term of this patent is extended or adjusted under 35 U.S.C. 154(b) by 0 days.

(21) Appl. No.: 18/280,122

(22) PCT Filed: Mar. 3, 2022

(86) PCT No.: PCT/IL2022/050236
§ 371 (c)(1),
(2) Date: Sep. 1, 2023

(87) PCT Pub. No.: WO2022/185313
PCT Pub. Date: Sep. 9, 2022

(30) Foreign Application Priority Data

Mar. 3, 2021 (IL) .......................................... 281248
Oct. 25, 2021 (IL) .......................................... 287544

(51) Int. Cl.
*A61M 39/10* (2006.01)
*A61M 39/22* (2006.01)
*A61J 1/20* (2006.01)

(52) U.S. Cl.
CPC ...... *A61M 39/1011* (2013.01); *A61M 39/225* (2013.01); *A61J 1/2031* (2015.05);
(Continued)

(58) Field of Classification Search
CPC ........ A61J 1/2096; A61J 1/201; A61J 1/2055; A61J 1/2089; A61J 1/1481; A61J 1/2031;
(Continued)

(56) References Cited

U.S. PATENT DOCUMENTS

| 4,729,401 A | 3/1988 | Raines |
| 5,349,984 A | 9/1994 | Weinheimer et al. |

(Continued)

FOREIGN PATENT DOCUMENTS

| EP | 2379162 A1 | 10/2011 |
| EP | 2386324 A1 | 11/2011 |

(Continued)

OTHER PUBLICATIONS

Jul. 9, 2023 International Preliminary Report on Patentability issued on International Application No. PCT/IL2022/050236.
(Continued)

*Primary Examiner* — Kai H Weng
(74) *Attorney, Agent, or Firm* — Whitestone Law, PLLC

(57) ABSTRACT

Some embodiments are directed to a connector for connection with a fluid transfer device, including an outer body having a longitudinal axis; and a luer lock connection port positioned within the outer body and configured to be coupled with an external port of said fluid transfer device. The luer lock connection port can be rotatable about the longitudinal axis at least in one of a clockwise direction and a counter-clockwise direction at least prior to initiation of coupling thereof with the external port. The outer body can be structured, and the luer lock connection port is positioned therewithin, such that to prevent an operator to access, through the outer body, directly by fingertips an exterior of the luer lock connection port after the luer lock connection port has been coupled with the external port.

20 Claims, 59 Drawing Sheets

(52) U.S. Cl.
CPC ............ *A61J 1/2034* (2015.05); *A61J 1/2055* (2015.05); *A61J 1/2065* (2015.05)

(58) Field of Classification Search
CPC .. A61J 1/2034; A61J 1/2065; A61M 39/1011; A61M 2039/1016; A61M 2039/1033; A61M 2039/1027; A61M 39/10; A61M 2039/1038; A61M 2039/1044; A61M 2039/1077

See application file for complete search history.

(56) References Cited

U.S. PATENT DOCUMENTS

| | | | |
|---|---|---|---|
| 5,807,312 | A | 9/1998 | Dzwonkiewicz |
| D720,067 | S | 12/2014 | Rosenquist |
| 2005/0234428 | A1 | 10/2005 | Spohn et al. |
| 2008/0045919 | A1 | 2/2008 | Jakob et al. |
| 2011/0168292 | A1 | 7/2011 | Luzbetak et al. |
| 2011/0178493 | A1 | 7/2011 | Okiyama |
| 2012/0046636 | A1 | 2/2012 | Kriheli |
| 2013/0282142 | A1 | 10/2013 | Perkins et al. |
| 2015/0083950 | A1 | 3/2015 | Okiyama |
| 2015/0231385 | A1 | 8/2015 | Mijers |
| 2016/0106967 | A1 | 4/2016 | Guala |
| 2017/0095404 | A1 | 4/2017 | Fangrow |
| 2017/0203089 | A1 | 7/2017 | Ciccone et al. |
| 2018/0000695 | A1 | 1/2018 | Stroup |
| 2018/0133451 | A1 | 5/2018 | Takeuchi |
| 2018/0296175 | A1 | 10/2018 | Carmody et al. |
| 2019/0093775 | A1 | 3/2019 | Feith et al. |
| 2019/0117515 | A1 | 4/2019 | Fangrow |
| 2020/0038290 | A1 | 2/2020 | Labroc et al. |
| 2020/0323734 | A1* | 10/2020 | Ueda ................... A61M 39/14 |
| 2020/0345996 | A1 | 11/2020 | DeMeritt et al. |

FOREIGN PATENT DOCUMENTS

| | | |
|---|---|---|
| EP | 2379162 B1 | 10/2013 |
| EP | 2712652 A2 | 4/2014 |
| EP | 2712652 A3 | 8/2017 |
| EP | 2712652 B1 | 5/2021 |
| WO | 20070983 A1 | 4/2020 |

OTHER PUBLICATIONS

Jun. 12, 2022 Written Opinion of the International Searching Authority issued on International Application No. PCT/IL2022/050236.

Jun. 12, 2022 International Search Report issued on International Application No. PCT/IL2022/050236.

* cited by examiner

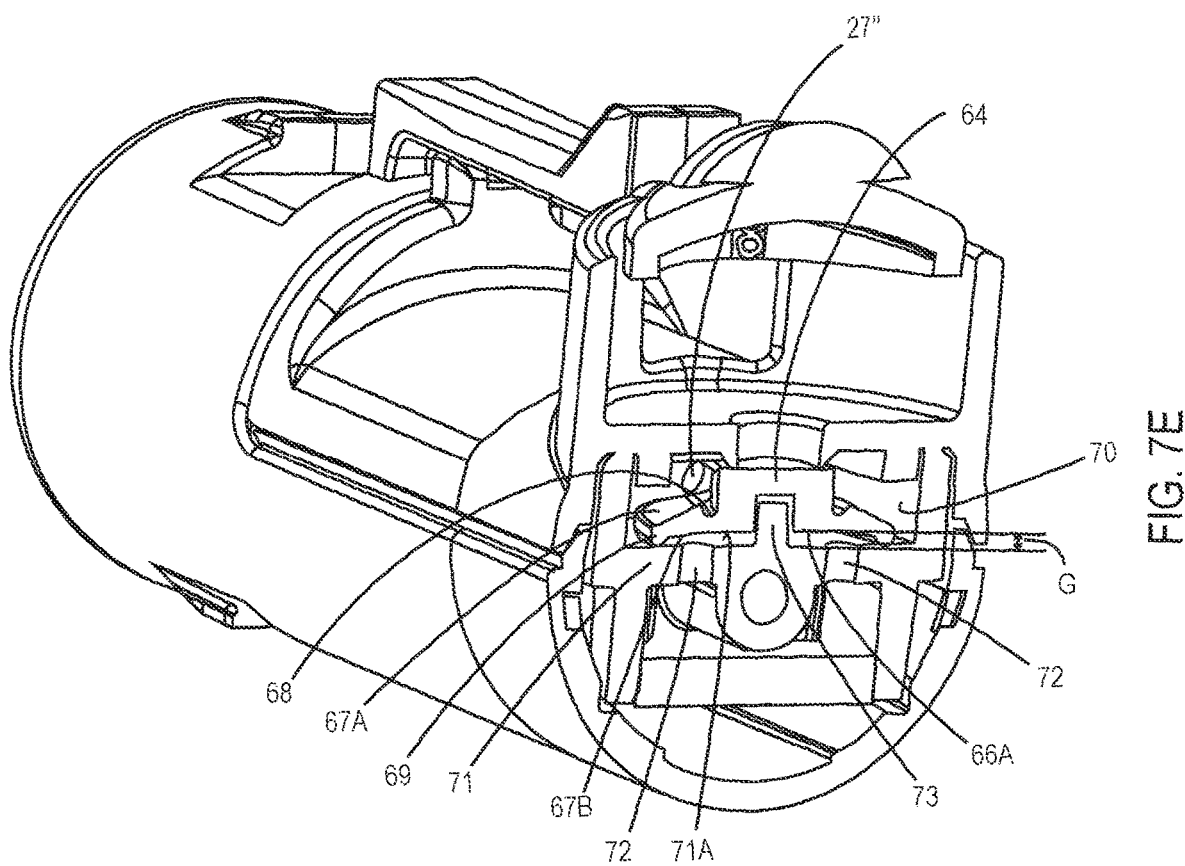

TAMPER PROOF LUER LOCK CONNECTOR AND A VALVE ARRANGEMENT FOR AN ADAPTOR

CROSS REFERENCE TO RELATED APPLICATIONS

This application is a national phase filing under 35 CFR. § 371 of and claims priority to PCT Patent Application No. PCT/IL2022/050236, filed on Mar. 3, 2022, which claims the priority benefit under 35 U.S.C. § 119 of Israeli Patent Application No. 281248, filed on Mar. 3, 2021, and Israeli Patent Application No. 287544, filed on Oct. 25, 2021, the contents of each of which are hereby incorporated in their entireties by reference.

TECHNOLOGICAL FIELD

The presently disclosed subject matter relates to a tamper proof luer lock connector for use with an adaptor in spill proof fluid transfer systems, and a valve arrangement for maintaining a desired air pressure within the adaptor.

BACKGROUND

In fluid transfer systems, especially where transfer of hazardous fluids is involved, the exposure of the fluids to the environment is highly undesirable, and in some cases may even lead to fatal accidents. Thus, the apparatus, such as fluid transfer devices, adaptors, connectors, valves, etc. that are to be used in such systems need to be completely spill proof and contamination free. In certain examples, the connections between some devices need to be such that the connections cannot be accidentally or mischievously disconnected, and at the same time such that those can be disconnected by an operator with proper care and proper technique.

Furthermore, in certain applications, the air pressure keeps on building and/or falling within the systems during transfer of the fluids. Such air pressure, when increased or decreased in an uncontrolled manner, may lead to malfunction of any apparatus or even the whole system.

Thus, there is a need and desire for a fluid transfer apparatus that solves at least some of the problems discussed above.

GENERAL DESCRIPTION

According to a first aspect of the presently disclosed subject matter, there is provided a connector for connection with a fluid transfer device, said connector comprising:
  an outer body having a longitudinal axis; and
  a luer lock connection port positioned within the outer body and configured to be coupled with an external port of said fluid transfer device, the luer lock connection port being rotatable about the longitudinal axis at least in one of a clockwise direction and a counter-clockwise direction at least prior to initiation of coupling thereof with the external port;
  wherein the outer body is structured, and the luer lock connection port is positioned therewithin, such that to prevent an operator to access, through the outer body, directly by fingertips an exterior of the luer lock connection port after the luer lock connection port has been coupled with the external port.

The fluid transfer device can be a generally known luer lock connection device to be used in medical systems, for example in drug mixing systems where safe transfer of hazardous drugs from one container to another is required. In some examples, the fluid transfer device can be any connection device facilitating the transfer of fluids between containers.

The above mentioned connector can be integrated with an adaptor configured to facilitate the connection between a container, either directly or via another corresponding adaptor, and the fluid transfer device. In some examples, the container can be a syringe, and the adaptor can facilitate the connection between the syringe, directly or via a standard syringe adaptor, and a normal female luer lock connection device. In some examples, the adaptor facilitates the conversion of a standard female luer lock port into a docking port for safe connection with female connector of a syringe adaptor.

The outer body can be a generally cylindrical hollow body having a proximal end to be positioned towards the fluid transfer device and a distal end to be positioned towards the container during use thereof. The luer lock connection port can be positioned within the outer body at the proximal end thereof to receive an external port of the fluid transfer device. In specific applications, the external port is the standard female luer lock port. The luer lock connection port can be positioned within the outer body so as to have a common longitudinal axis with the outer body, and such that the luer lock connection port can rotate about that axis.

The luer lock connection port can include threads to receive corresponding threads formed on the external port to be coupled thereto. When the external port is brought in contact with the luer lock connection port to be threaded therewith, the coupling is initiated. The coupling is under process when the external port is being rotated so as to be threaded with the luer lock connection port. As prior to the initiation of the coupling, the luer lock connection port is rotatable within the outer body, thus, when the coupling is to be done, the rotation of the luer lock connection port at least in the direction of the threading, which in general applications can be clockwise, needs to be prevented at least while the coupling is under process. When the external port has been completely threaded with the luer lock connection port, the coupling is completed. The luer lock connection port can rotate about the longitudinal axis after the coupling is completed.

The outer body generally covers the luer lock connection port, when positioned therewithin and coupled to the external port, in such a way that there is no easy access to the luer lock connection port, or at least by fingertips. In some examples, sidewall of the outer body may have one or more openings, each smaller in size than that of fingertip of a child, so that, especially when in use in medical drug delivery systems, a child cannot access the luer lock connection port by fingertips. The inability of the child to access the luer lock connection port assures inability of the child to prevent rotation of the luer lock connection port thereby preventing unintentional decoupling of the luer lock connection port from the external port. The average diameter of the fingertips of a child of about 3-10 years of age is approximately 10-12 mm. Accordingly, in some examples, at least one dimension of each of the one or more openings can be smaller than 10 mm. Therefore, the connector is configured as a tamper proof connector.

The luer lock connection port can be rotatable about the longitudinal axis in both of the clockwise direction and the counter-clockwise direction at least prior to the initiation of coupling thereof with the external port.

The luer lock connection port can be rotatable about the longitudinal axis in both of the clockwise direction and the counter-clockwise direction upon coupling thereof with the external port.

In some examples, the luer lock connection port can be rotatable about the longitudinal axis in at least the counter-clockwise direction upon coupling thereof with the external port.

For the purposes of understanding of whole of the present application, the clockwise and counter-clockwise directions are to be understood as being seen from the direction of the external port towards the luer lock connection port.

The connector can further comprise a coupling facilitating mechanism configured to selectively assume a coupling enabled state at which it restricts the rotation of the luer lock connection port at least in the clockwise direction, and a coupling disabled state at which it allows the rotation of the luer lock connection port at least in the clockwise direction.

The coupling facilitating mechanism can include any structure as understood to a person having ordinary skill in the art as being capable of selectively preventing the rotation of the luer lock connection port within the outer body at least in the direction of threading, which in general applications can be clockwise. If in a particular example, the direction of threading is counter-clockwise, then the coupling facilitating mechanism, in coupling enabled state, can be configured to restrict the rotation of the luer lock connection port at least in the counter-clockwise direction. In some examples, the coupling facilitating mechanism can include a button, key, lever, or the like being external to the connector or being formed in the outer body which can be operated to prevent the rotation of the luer lock connection port within the outer body. In some examples, the coupling facilitating mechanism can include at least one pair of a projection and a catcher, one formed on the luer lock connection port and the other one formed on or operable through the outer body, in that the projection and the catcher can engage each other so as to prevent the rotation of the luer lock connection port within the outer body. The coupling facilitating mechanism can be configured to normally remain in coupling disabled state and can be actuated by an operator to attain the coupling enabled state when the coupling is to be done.

The coupling facilitating mechanism can be configured to assume the coupling enabled state at least during the time when coupling of the luer lock connection port with the external port is under process.

The coupling facilitating mechanism, in its coupling enabled state, can be configured to allow rotation of the luer lock connection port about the longitudinal axis in a counter-clockwise direction. Moreover, the coupling facilitating mechanism, in its coupling disabled state, can be configured to allow rotation of the luer lock connection port about the longitudinal axis in a counter-clockwise direction and/or the clockwise direction.

The luer lock connection port can be configured to axially displace along the longitudinal axis between a first position associated with the coupling disabled state, and a second position associated with the coupling enabled state. In some examples, the luer lock connection port, the outer body, and the coupling facilitating mechanism and positioning thereof with respect to each other can be configured such that the coupling facilitating mechanism can be displaced into the coupling enabled state only when the luer lock connection port and the outer body are at a particular position with respect to each other. The particular position can be defined by an extent to which the luer lock connection port is within the outer body along the longitudinal axis.

According to an example, the luer lock connection port can be configured to freely displace from the first position to the second position upon application of a pushing force by the external port, i.e., the pushing force applied by an operator on the fluid transfer device during the coupling. The first position can be a normal position of the luer lock connection port within the outer body at which it can freely rotate in clockwise as well as counter-clockwise direction about the longitudinal axis. When in the first position, the luer lock connection port is spaced from the proximal end of the outer body at a first extent. At the second position, the luer lock connection port is spaced from the proximal end of the outer body at a second extent being greater than the first extent. When the luer lock connection port is in the second position, the coupling facilitating mechanism either automatically attains or can be actuated to attain the coupling enabled state and in response thereto, the rotation of the luer lock connection port in the clockwise direction is restricted. Although, at the coupling enabled state, the rotation of the luer lock connection port in the counter-clockwise direction may or may not be restricted.

The coupling facilitating mechanism can comprise at least one locking member mounted on an external surface of the luer lock connection port and at least one arresting member mounted on an internal surface of the outer body, wherein at the second position, the locking member engages with the arresting member, thereby restricting the rotation of the luer lock connection port at least in the clockwise direction. At the first position, the locking member can disengage from the arresting member. In some examples, the luer lock connection port can have at least one sidewall extending generally parallel to the longitudinal axis and a back wall extending generally perpendicular to the longitudinal axis. The sidewall and the back wall of the luer lock connection port can have respective exterior surfaces facing the outer body and opposite interior surfaces. The outer body can have at least one sidewall corresponding to that of the luer lock connection port, and a back wall corresponding to that of the luer lock connection port. The sidewall and the back wall of the outer body can have respective interior surfaces facing the luer lock connection port and opposite interior surfaces. According to one example, the exterior surface of the back wall of the luer lock connection port can have at least one locking member, and the interior surface of the back wall of the outer body can have corresponding arresting member, both constituting the coupling facilitating mechanism. When the luer lock connection port is in the first position, the locking member is distant from the arresting member, and the luer lock connection port can rotate at least in the clockwise direction. When the luer lock connection port is pushed further within the outer body, for example by the external port (upon being pushed an operator) at the initiation of the coupling, the locking member engages, and gets arrested with, the arresting member, thereby shifting the coupling facilitating mechanism into the coupling enabled state. The engagement of the locking member and the arresting member restricts the rotation of the luer lock connection port at least in the clockwise direction.

According to another example, the locking member can be formed on the external surface of the sidewall of the luer lock connection port. The arresting member can be formed in the form of a button, key, lever, etc. on the outer body or can be an external member to be operated through an opening in the sidewall of the outer body to engage the locking member to restrict the rotation of the luer lock connection port at least in the clockwise direction.

The connector can further comprise a decoupling facilitating mechanism configured to selectively assume a decoupling disabled state at which it allows rotation of the luer lock connection port about the longitudinal axis thereof at least in a counter-clockwise direction, and a decoupling enabled state at which it restricts the rotation of the luer lock connection port at least in the counter-clockwise direction so as to allow decoupling of the external port from the luer lock connection port.

The decoupling facilitating mechanism can include any structure as understood to a person having ordinary skill in the art as being capable of selectively preventing the rotation of the luer lock connection port within the outer body at least in the direction of unthreading, which in general applications can be counter-clockwise. If in a particular example, the direction of unthreading is clockwise, then the decoupling facilitating mechanism, in decoupling enabled state, can be configured to restrict the rotation of the luer lock connection port at least in the clockwise direction. In some examples, the decoupling facilitating mechanism can include a button, key, lever, or the like being external to the connector or being formed in the outer body which can be operated to prevent the rotation of the luer lock connection port within the outer body. In some examples, the decoupling facilitating mechanism can include at least one pair of a projection and a catcher, one formed on the luer lock connection port and the other one formed on or operable through the outer body, in that, the projection and the catcher can engage each other so as to prevent the rotation of the luer lock connection port within the outer body. The decoupling facilitating mechanism can be configured to be in decoupling disabled state, and can be actuated by an operator (e.g., by a pushing force) to attain the decoupling enabled state when the decoupling is to be done.

The decoupling facilitating mechanism can be configured to assume the decoupling enabled state at least during the time when decoupling of the luer lock connection port from the external port is under process.

The outer body can comprise a sidewall with at least one opening formed therein and configured to be used in conjunction with said decoupling facilitating mechanism so as to provide access to an external surface of the luer lock connection port at least at said decoupling enabled state. In some examples, the decoupling mechanism includes a button, actuator, key, lever, or the like being external to the connector and can be used to access the sidewall of the luer lock connection port via an opening formed in the sidewall of the outer body so as to get hold of the luer lock connection port to restrict the rotation thereof, thereby facilitating unthreading of the external port from the luer lock connection port.

The decoupling facilitating mechanism can comprise an actuator at least partially positioned in the opening, the actuator having an actuator internal surface facing the luer lock connection port and an opposite actuator external surface, the decoupling facilitating mechanism being configured to assume the decoupling enabled state upon application of a pressing force on the actuator, and the decoupling disabled state upon removal of said force. In some examples, the actuator can be a button at least partially positioned in the opening of the sidewall of the outer body. When it is intended to decouple the external port from the luer lock connection port, an operator can press the button and the internal surface of the button engages the exterior surface of the luer lock connection port thereby restricting the rotation of the luer lock connection port. In cases when the decoupling facilitating mechanism comprises an actuator, button, or lever or the like fixed with the outer body, the corresponding opening can be bigger than the other openings on the sidewall, however, the actuator, button, or lever or the like can be positioned in the opening so as to leave no enough space around the same to allow direct access by the fingertip to the luer lock connection port. In cases when the decoupling facilitating mechanism comprises an actuator, button, or lever or the like as external non-fixed elements, no opening can be big enough to allow to allow direct access by the fingertips to the luer lock connection port.

At the decoupling enabled state, a minimum distance between the longitudinal axis and the actuator external surface is lesser than a minimum distance between the longitudinal axis and an external surface of a rim of the opening. At the decoupling enabled state, at least a majority of the actuator external surface is positioned below an imaginary surface defined by a rim of the opening. In some examples, the actuator can be positioned in the opening such that the external surface of the actuator, i.e., the surface of the actuator facing away from the luer lock connection port, has at least some portion being sunk into the opening so as to be further inwardly towards the luer lock connection port than the rim of the opening. Accordingly, the actuator can be structured to be a hidden button which an operator would not normally assume to be a button for facilitating decoupling the external port from the luer lock connection port.

The actuator can have a first portion extending from the outer body, and a second portion extending from the first portion, wherein the first portion forms a part of the outer body. The first portion and the second portion can constitute a lever. In some examples, the actuator can be in the form of a lever. The actuator can have a first portion being an extension of the outer body, and a second portion being a continuation of the first portion.

The decoupling mechanism can comprise a first engaging portion constituting a part of an external surface of the luer lock connection port, and a second engaging portion constituting a part of the actuator internal surface, wherein at the decoupling enabled state, the first engaging portion can engage with the second engaging portion thereby restricting the rotation of the luer lock connection port at least in the counter-clockwise direction. At the decoupling disabled state, the first engaging portion can disengage from the second engaging portion. The first engaging portion can comprise at least one protrusion formed on the external surface of the luer lock connection port, and the second engaging portion can comprise at least one tooth projecting from the actuator internal surface, wherein at the decoupling enabled state, the at least one tooth can engage with the at least one protrusion thereby restricting the rotation of the luer lock connection port at least in the counter-clockwise direction. At the decoupling disabled state, the at least one tooth can disengage from the at least one protrusion.

In some examples, the protrusion and the tooth can switch positions, i.e., the tooth can be formed on the actuator internal surface and the projection can be formed on the external surface of the luer lock connection port.

The actuator can be configured to be pressed only when the at least one protrusion is radially displaced with respect to the at least one tooth. The at least one protrusion can have a protrusion side surface extending from the external surface of the luer lock connection port towards the actuator, and the at least one tooth can have a tooth side surface extending from the actuator internal surface towards the luer lock connection port, wherein at the decoupling enabled state, the tooth side surface engages the protrusion side surface.

The luer lock connection port can be configured to axially displace along the longitudinal axis into a third position. The third position can be any position between the first position and the second position, and in a particular example, can be the first position. In some examples, the first position can be a normal position of the luer lock connection port within the outer body and the luer lock connection port is the first extent within the outer body from the proximal end of the outer body. At the second position, the luer lock connection port can be second extent, greater than the first extent, within the outer body from the proximal end of the outer body.

The luer lock connection port can be configured to freely displace from the second position to the third position upon application of a pulling force during decoupling the external port from the luer lock connection port. In some examples, when decupling is to be done, the fluid transfer device can be pulled in a direction away from the connector, thereby pulling the luer lock connection port into the third position. The third position can be any position between the first position and the second position, and in a particular example, can be the first position.

The decoupling facilitating mechanism can be configured to assume the decoupling enabled state upon the luer lock connection port displacing into the third position. In some examples, the decoupling facilitating mechanism can be configured to assume the decoupling enabled state upon the luer lock connection port displacing into the second position. In some examples, the luer lock connection port, the outer body, and the decoupling facilitating mechanism and positioning thereof with respect to each other can be configured such that the decoupling facilitating mechanism displaces automatically or can be displaced by the operator into the decoupling enabled state only when the luer lock connection port is at the third position. The third position can be any position between the first position and the second position, and in a particular example, can be the first position.

Accordingly, in order to decouple the external port from the luer lock connection port, the luer lock connection port can be required to be brought into its third position, which as mentioned above can be the first and normal position, and the tooth be positioned with respect to the protrusion such that the tooth and the protrusion are not radially aligned, i.e., are not above/under each other, and then the decoupling facilitating mechanism be displaced into its decoupling enabled state thereby restricting the rotation of the luer lock connection port in counter-clockwise direction. In such a state, the external port can be rotated counter-clockwise and can be decoupled from the luer lock connection port.

In some examples, the coupling facilitating mechanism and the decoupling facilitating mechanism can be the same mechanism configured to facilitate coupling as well as decupling. For instance, the mechanism, when actuated, can be configured to restrict the rotation of the luer lock connection port in any and both of the clockwise and counter-clockwise directions.

The luer lock connection port can be a male luer lock connection port comprising an elongate central member and a collar surrounding the elongate central member, wherein the male luer lock connection port can be configured to be coupled to the external port by threadingly receiving the external port between the collar and the elongate central member, such that upon coupling, the collar is positioned between the external port and the outer body, and the outer body covers at least a majority of the collar from outside. In some examples, the luer lock connection port can be a male port having an elongate central member constituting the male member thereof, to be inserted into a corresponding female connector. The central member can be at least radially surrounded by a collar. The collar can include threads on its internal surface facing the elongate central member. The threads can be configured to receive corresponding threads formed on an external surface of the external port.

The collar can extend parallel to the elongate central member, and a length of the collar can range between 5.4 mm to 8 mm. The outer body can cover at least a majority of the collar. The skirt member and the elongate central member can be integrally formed.

The outer body can radially cover at least a majority of the luer lock connection port. The outer body can radially cover at least 90% of the luer lock connection port. The outer body radially can cover at least a majority of a sidewall of the luer lock connection port. The outer body can radially cover at least 90% of a sidewall of the luer lock connection port.

According to a second aspect of the presently disclosed subject matter, there is provided an adaptor configured for use in medical fluid transfer devices, the adaptor comprising the connector as described above according to the first aspect of the presently disclosed subject matter.

The adaptor can comprise a septum positioned at a distal end thereof configured to receive at least one needle of a syringe therethrough.

The connector can constitute a proximal portion of the adaptor.

According to a third aspect of the presently disclosed subject matter, there is provided a connector for connection with a fluid transfer device, said connector comprising:
 a luer lock connection port configured to be coupled with an external port of said fluid transfer device;
 an outer body covering at least a portion of the luer lock connection port; and
 a decoupling facilitating mechanism configured to selectively assume a decoupling disabled state at which it allows rotation of the luer lock connection port about a longitudinal axis thereof at least in a counter-clockwise direction, and a decoupling enabled state at which it restricts the rotation of the luer lock connection port at least in the counter-clockwise direction so as to allow decoupling of the external port from the luer lock connection port.

The fluid transfer device can be a generally known luer lock connection device to be used in medical systems, for example in drug mixing systems where safe transfer of hazardous drugs from one container to another is required. In some examples, the fluid transfer device can be any connection device facilitating transfer of fluids between containers.

The above mentioned connector can be integrated with an adaptor configured to facilitate connection between a container, either directly or via a corresponding adaptor, and the fluid transfer device. In some examples, the container can be a syringe, and the adaptor can facilitate connection between the syringe, directly or via a standard syringe adaptor, and a normal female luer lock connection device. In some examples, the adaptor facilitates conversion of a standard female luer lock port into a docking port for safe connection with female connector of a syringe adaptor.

The outer body can be a generally cylindrical hollow body having a proximal end to be positioned towards the fluid transfer device and a distal end to be positioned towards the container during use thereof. The luer lock connection port can be positioned within the outer body at the proximal end thereof to receive an external port of the fluid transfer device. In specific applications, the external port is the standard female luer lock port. The luer lock connection port can be positioned within the outer body so as to have a common longitudinal axis with the outer body, and such that the luer lock connection port can rotate about that axis. The luer lock connection port can include threads to receive corresponding threads formed on the external port to be coupled thereto.

The outer body can generally cover the luer lock connection port, when positioned therewithin and coupled to the external port, in such a way that there is no easy access to the luer lock connection port, or at least by fingertips. In some examples, sidewall of the outer body can have one or more openings, each smaller in size than that of fingertip of a child, so that, especially when in use in medical drug delivery systems, a child cannot access the luer lock connection port by fingertips. The inability of the child to access the luer lock connection port assures inability of the child to prevent rotation of the luer lock connection port thereby preventing unintentional decoupling of the luer lock connection port from the external port. The average diameter of the fingertips of a child of about 3-10 years of age is approximately 10-12 mm. Accordingly, in some examples, at least one dimension of each of the one or more openings can be smaller than 10 mm. Therefore, the connector can be configured as a tamper proof connector.

The luer lock connection port can rotate within the outer body after having been coupled to the external port, thus, in order to decouple the luer lock connection port from the external port, it is necessary to restrict the rotation of the luer lock connection in the direction of unthreading, which in general applications can be counter-clockwise. If in a particular example, the direction of unthreading is clockwise, then the decoupling facilitating mechanism, in decoupling enabled state, can be configured to restrict the rotation of the luer lock connection port at least in the clockwise direction. The coupling facilitating mechanism can include any structure as understood to a person having ordinary skill in the art as being capable of selectively preventing the rotation of the luer lock connection port within the outer body at least in the direction of unthreading. In some examples, the decoupling facilitating mechanism can include a button, key, lever, or the like being external to the connector or being formed in the outer body which can be operated to prevent the rotation of the luer lock connection port within the outer body. In some examples, the decoupling facilitating mechanism can include at least one pair of a projection and a catcher, one formed on the luer lock connection port and the other one formed on or operable through the outer body, in that, the projection and the catcher can engage each other so as to prevent the rotation of the luer lock connection port within the outer body. The decoupling facilitating mechanism can be configured to normally remain in decoupling disabled state, and can be actuated by an operator to attain the decoupling enabled state when the decoupling is to be done.

The decoupling facilitating mechanism can be configured to assume the decoupling enabled state at least during the time when decoupling of the luer lock connection port from the external port is under process. The decoupling is to be understood as being under process during the time after the decoupling has been initiated and before the external port has been completely separated from the luer lock connection port.

The outer body can comprise a sidewall with at least one opening formed therein and configured to be used in conjunction with said decoupling facilitating mechanism so as to provide access to an external surface of the luer lock connection port at least at said decoupling enabled state. In some examples, the decoupling mechanism can include a button, actuator, key, lever, or the like being external to the connector and can be used to access the sidewall of the luer lock connection port via an opening formed in the sidewall of the outer body so as to get hold of the luer lock connection port to restrict the rotation thereof, thereby facilitating unthreading of the external port from the luer lock connection port.

The decoupling facilitating mechanism can comprise an actuator at least partially positioned in the opening, the actuator having an actuator internal surface facing the luer lock connection port and an opposite actuator external surface, the decoupling facilitating mechanism being configured to assume the decoupling enabled state upon application of a pressing force on the actuator, and the decoupling disabled state upon removal of said force. In some examples, the actuator can be a button at least partially positioned in the opening of the sidewall of the outer body. When it is intended to decouple the external port from the luer lock connection port, an operator can press the button and the internal surface of the button engages the exterior surface of the luer lock connection port thereby restricting the rotation of the luer lock connection port. In cases when the decoupling facilitating mechanism comprises an actuator, button, or lever or the like fixed with the outer body, the corresponding opening can be bigger than the other openings on the sidewall, however, the actuator, button, or lever or the like can be positioned in the opening so as to leave no space around the same to allow direct access by the fingertips to the luer lock connection port. In cases when the decoupling facilitating mechanism comprises an actuator, button, or lever or the like as external non-fixed elements, no opening can be big enough to allow to allow direct access by the fingertips to the luer lock connection port.

At the decoupling enabled state, a minimum distance between the longitudinal axis and the actuator external surface can be lesser than a minimum distance between the longitudinal axis and an external surface of a rim of the opening. At the decoupling enabled state, at least a majority of the actuator external surface can be positioned below an imaginary surface defined by a rim of the opening. In some examples, the actuator can be positioned in the opening such that the external surface of the actuator, i.e., the surface of the actuator facing away from the luer lock connection port, can have at least some portion being sunk into the opening so as to be further inwardly towards the luer lock connection port than the rim of the opening. Accordingly, the actuator can be structured to be a hidden button which an operator would not normally assume to be a button for facilitating decoupling the external port from the luer lock connection port.

The actuator can have a first portion extending from the outer body, and a second portion extending from the first portion, wherein the first portion can form a part of the outer body. The first portion and the second portion can constitute a lever. In some examples, the actuator can be in the form of a lever. The actuator can have a first portion being an extension of the outer body, and a second portion being a continuation of the first portion.

The decoupling mechanism can comprise a first engaging portion constituting a part of an external surface of the luer lock connection port, and a second engaging portion constituting a part of the actuator internal surface, wherein at the decoupling enabled state, the first engaging portion can engage with the second engaging portion thereby restricting the rotation of the luer lock connection port at least in the counter-clockwise direction. At the decoupling disabled state, the first engaging portion can disengage from the second engaging portion. The first engaging portion can comprise at least one protrusion formed on the external surface of the luer lock connection port and the second engaging portion can comprise at least one tooth projecting from the actuator internal surface, wherein at the decoupling enabled state, the at least one tooth can engage with the at least one protrusion thereby restricting the rotation of the luer lock connection port at least in the counter-clockwise direction. At the decoupling disabled state, the at least one tooth can disengage from the at least one protrusion.

In some examples, the protrusion and the tooth can switch positions, i.e., the tooth can be formed on the actuator internal surface and the projection can be formed on the external surface of the luer lock connection port.

The actuator can be configured to be pressed only when the at least one protrusion is radially displaced with respect to the at least one tooth. The at least one protrusion can have a protrusion side surface extending from the external surface of the luer lock connection port towards the actuator, and the at least one tooth can have a tooth side surface extending from the actuator internal surface towards the luer lock connection port, wherein at the decoupling enabled state, the tooth side surface engages the protrusion side surface.

The luer lock connection port can be configured to axially displace along the longitudinal axis between a first position and a second position. In some examples, the luer lock connection port, the outer body, and the decoupling facilitating mechanism and positioning thereof with respect to each other can be configured such that the decoupling facilitating mechanism can be displaced into the decoupling enabled state only when the luer lock connection port and the outer body are at a particular position with respect to each other. The particular position can be defined by an extent to which the luer lock connection port is within the outer body along the longitudinal axis.

According to an example, the luer lock connection port can be configured to displace from the first position to the second position upon application of a pushing force applied by an operator on the fluid transfer device during coupling. The first position can be a normal position of the luer lock connection port within the outer body at which it can freely rotate in clockwise as well as counter-clockwise direction about the longitudinal axis. When in the first position, the luer lock connection port is a first extent within the outer body from the proximal end of the outer body. At the second position, the luer lock connection port can be a second extent, greater than the first extent, within the outer body from the proximal end of the outer body.

The luer lock connection port can be configured to axially displace along the longitudinal axis into a third position. The luer lock connection port can be configured to displace from the second position to the third position upon application of a pulling force applied by an operator on the fluid transfer device during decoupling. The third position can be any position between the first position and the second position, and in a particular example, can be the first position. In some examples, when decupling is to be done, the fluid transfer device can be pulled in a direction away from the connector, thereby pulling the luer lock connection port into the third position.

The decoupling facilitating mechanism can be configured to assume the decoupling enabled state upon the luer lock connection port displacing into the second position in some examples.

The decoupling facilitating mechanism can be configured to assume the decoupling enabled state upon the luer lock connection port displacing into the third position. The third position can be any position between the first position and the second position, and in a particular example, can be the first position.

In some examples, the luer lock connection port, the outer body, and the decoupling facilitating mechanism and positioning thereof with respect to each other can be configured such that the decoupling facilitating mechanism displaces automatically or can be displaced by the operator into the decoupling enabled state only when the luer lock connection port is at the third position.

Accordingly, in order to decouple the external port from the luer lock connection port, the luer lock connection port can be required to be brough into its third position, which as mentioned above can be the first and normal position, and the tooth be positioned with respect to the protrusion such that the tooth and the protrusion are not radially aligned, i.e., are not above/under each other, and then the decoupling facilitating mechanism be displaced into its decoupling enabled state thereby restricting the rotation of the luer lock connection port in counter-clockwise direction. In such a state, the external port can be rotated counter-clockwise and can be decoupled from the luer lock connection port.

The connector can further comprise a coupling facilitating mechanism configured to selectively assume a coupling enabled state at which it restricts the rotation of the luer lock connection port at least in a clockwise direction, and a coupling disabled state at which it allows the rotation of the luer lock connection port at least in the clockwise direction. The coupling facilitating mechanism can include any structure as understood to a person having ordinary skill in the art as being capable of selectively preventing the rotation of the luer lock connection port within the outer body at least in the direction of threading, which in general applications can be clockwise. If in a particular example, the direction of threading is counter-clockwise, then the coupling facilitating mechanism, in coupling enabled state, can be configured to restrict the rotation of the luer lock connection port at least in the counter-clockwise direction. In some examples, the coupling facilitating mechanism can include a button, key, lever, or the like being external to the connector or being formed in the outer body which can be operated to prevent the rotation of the luer lock connection port within the outer body. In some examples, the coupling facilitating mechanism can include at least one pair of a projection and a catcher, one formed on the luer lock connection port and the other one formed on or operable through the outer body, in that, the projection and the catcher can engage each other so as to prevent the rotation of the luer lock connection port within the outer body. The coupling facilitating mechanism can be configured to assume the coupling disabled state, and can be actuated by an operator to attain the coupling enabled state when the coupling is to be done.

When the external port is brought in contact with the luer lock connection port to be threaded therewith, the coupling is initiated. The coupling is under process when the external port is being rotated so as to be threaded with the luer lock connection port. At least prior to the initiation of the coupling, the luer lock connection port is rotatable within the outer body, thus, when the coupling is to be done, the rotation of the luer lock connection port at least in the direction of the threading, which in general applications can be clockwise, needs to be prevented at least until the coupling is under process. When the external port has been completely threaded with the luer lock connection port, the coupling is completed. The luer lock connection port can rotate about the longitudinal axis after the coupling is completed.

The coupling facilitating mechanism can be configured to assume the coupling enabled state at least during the time when coupling of the luer lock connection port with the external port is under process.

The coupling facilitating mechanism, in its coupling enabled state, can be configured to allow rotation of the luer lock connection port about the longitudinal axis in the counter-clockwise direction. The coupling facilitating mechanism, in its coupling disabled state, can be configured to allow rotation of the luer lock connection port about the longitudinal axis in a counter-clockwise direction.

In some examples, the luer lock connection port can be rotatable about the longitudinal axis in at least the counter-clockwise direction upon coupling thereof with the external port.

In some examples, the coupling disabled state can be associated with the first position and the coupling enabled state can be associated with the second position.

In some examples, the luer lock connection port, the outer body, and the coupling facilitating mechanism and positioning thereof with respect to each other can be configured such that the coupling facilitating mechanism can be displaced into the coupling enabled state only when the luer lock connection port and the outer body are at a particular position with respect to each other. The first position can be a normal position of the luer lock connection port within the outer body at which it can freely rotate in clockwise as well as counter-clockwise direction about the longitudinal axis. When in the first position, the luer lock connection port is a first extent within the outer body from the proximal end of the outer body. At the second position, the luer lock connection port can be a second extent, greater than the first extent, from the proximal end of the outer body. When the luer lock connection port is in the second position, the coupling facilitating mechanism either automatically attains or can be actuated to attain the coupling enabled state and in response thereto, the rotation of the luer lock connection port in the clockwise direction is restricted. Although, at the coupling enabled state, the rotation of the luer lock connection port in the counter-clockwise direction may or may not be restricted.

The coupling facilitating mechanism can comprise at least one locking member mounted on an external surface of the luer lock connection port and at least one arresting member mounted on an internal surface of the outer body, wherein at the second position, the locking member can engage with the arresting member thereby restricting the rotation of the luer lock connection port at least in the clockwise direction. At the normal position, the locking member can disengage from the arresting member.

In some examples, the luer lock connection port can have at least one sidewall extending generally parallel to the longitudinal axis and a back wall extending generally perpendicular to the longitudinal axis. The sidewall and the back wall of the luer lock connection port can have respective exterior surfaces facing the outer body and opposite interior surfaces. The outer body can have at least one sidewall corresponding to that of the luer lock connection port, and a back wall corresponding to that of the luer lock connection port. The sidewall and the back wall of the outer body can have respective interior surfaces facing the luer lock connection port and opposite interior surfaces. According to one example, the exterior surface of the back wall of the luer lock connection port can have at least one locking member, and the interior surface of the back wall of the outer body can have corresponding arresting member, both constituting the coupling facilitating mechanism. When the luer lock connection port is in the first position, the locking member is distant from the arresting member, and the luer lock lock connection port can rotate at least in the clockwise direction. When the luer lock connection port is pushed further within the outer body, for example by the external port at the initiation of the coupling, the locking member engages, and gets arrested with, the arresting member, thereby shifting the coupling facilitating mechanism into the coupling enabled state. The engagement of the locking member and the arresting member restricts the rotation of the luer lock connection port at least in the clockwise direction.

According to another example, the locking member can be formed on the exterior surface of the sidewall of the luer lock connection port. The arresting member can be formed in the form of a button, key, lever, etc. on the outer body or can be an external member to be operated through an opening in the sidewall of the outer body to engage the locking member to restrict the rotation of the luer lock connection port at least in the clockwise direction.

The luer lock connection port can be a male luer lock connection port comprising an elongate central member and a collar surrounding the elongate central member, wherein the male luer lock connection port can be configured to be coupled to the external port by threadingly receiving the external port between the collar and the elongate central member, such that upon coupling, the collar is positioned between the external port and the outer body, and the outer body covers at least a majority of the collar from outside. In some examples, the luer lock connection port can be a male port having an elongate central member constituting the male member thereof, to be inserted into a corresponding female connector. The central member can be at least radially surrounded by a collar. The collar can include threads on its internal surface facing the elongate central member. The threads can be configured to receive corresponding threads formed on an external surface of the external port.

The collar can extend parallel to the elongate central member, and a length of the collar can range between 5.4 mm to 8 mm. The outer body can cover at least a majority of the collar. The skirt member and the elongate central member can be integrally formed.

The outer body can radially cover at least a majority of the luer lock connection port. The outer body can radially cover at least 90% of the luer lock connection port. The outer body can radially cover at least a majority of a sidewall of the luer lock connection port. The outer body can radially cover at least 90% of a sidewall of the luer lock connection port.

According to a fourth aspect of the presently disclosed subject matter, there is provided an adaptor configured for use in medical fluid transfer devices, the adaptor comprising the connector as described above according the first aspect of the presently disclosed subject matter.

The adaptor can comprise a septum positioned at a distal end thereof configured to receive at least one needle of a syringe therethrough.

The connector can constitute a proximal portion of the adaptor.

According to a fifth aspect of the presently disclosed subject matter, there is provided a connector for connection with a fluid transfer device, said connector comprising:

an outer body having a longitudinal axis; and a luer lock connection port positioned within the outer body and configured to be coupled with an external port of said fluid transfer device, the luer lock connection port being rotatable about the longitudinal axis at least in one of a clockwise direction and a counter-clockwise direction at least prior to initiation of coupling thereof with the external port, wherein the outer body radially covers a majority of the luer lock connection port.

According to a sixth aspect of the presently disclosed subject matter, there is provided an adaptor configured for connection to a syringe having an air chamber and a liquid chamber, the adaptor comprising:

a liquid channel configured to be in communication with the liquid chamber;

an air channel configured to be in communication with the air chamber;

a first valve in fluid communication with the air channel, and having a first valve open state at which it allows air in the air channel to escape into ambiance, and a first valve normally closed state.

In some examples, the above mentioned adaptor can be configured to be used in drug delivery systems where safe transfer of drugs (e.g., hazardous drugs) is required.

The above mentioned adaptor can be configured to solve the problem of overpressure in the syringes comprising air chambers which are sealed from fluid communication with the ambiance other than through an air needle extending from the air chamber to an exterior of the syringe. This problem can occur because of misuse and/or improper use of the syringe. In fact, in some examples, the operation of the syringe can even depend upon intake and/or discharge of air into and/or from the air chamber. For instance, the syringe can be configured to be used to inject a liquid into an external container or human body as well as to extract a liquid from an external container. The overpressure can occur during extraction of liquid from an external container into the syringe when the air chamber of the syringe is not in fluid communication with a volume for the air in the air chamber to be discharged into, and then air is required to be discharged for continued operation of the syringe.

In some examples, the adaptor can be a luer lock adaptor configured to facilitate a connection between a syringe and an external container for transfer of liquids therebetween, either similar to the one described above or any generally known luer lock adaptor. In some examples, the adaptor can be a spike adaptor configured to facilitate a connection between a syringe and an IV bag for transfer of liquids therebetween. The spike adaptor can be connected between at least two other devices, at a time, in order to establish a fluid connection therebetween when the spike adaptor is the intermediate device. It is noted that spike adaptors and their basic functionality are generally known in the art and are described herein briefly for the sake of clarity and completeness.

More particularly, the spike adaptor can be used for transferring the liquid between the syringe and the IV bag in two directions, i.e., from the IV bag to the syringe and vice versa. For instance, in some medical procedures, it is required that a syringe is used to extract a volume of saline water from an IV bag, and then replacing the extracted volume of saline water with a drug from a syringe (generally a different one). For a single spike adaptor to be able to be used for both the operations between the syringe(s) and the IV bag, the spike adaptor needs to be configured to facilitate flow of air between the air chamber of the syringe and the ambiance in both directions, i.e., discharge of air from the air chamber as well as intake of air into the air chamber, especially when the syringes to be used are those having air chambers which are sealed from fluid communication with the ambiance other than through an air needle extending from the air chamber to an exterior of the syringe. The above mentioned adaptor can be configured to facilitate exchange of air pressure within the air chamber of the syringe, during transfer of the liquids, directly with the ambiance.

The first valve can be configured to automatically displace into the first valve open state in response to air pressure within the air channel exceeding a first pre-determined threshold. The first valve is configured to automatically displace into the first valve closed state in response to air pressure within the air channel falling below the first pre-determined threshold.

The first valve is particularly in operation in association with a syringe that is used to withdraw the saline water from the IV bag through the adaptor. In some medical procedures, it needs to be a part of a protocol that only a new/unused syringe is used to withdraw the saline water from the IV bag, because a syringe that has already been used to handle hazardous drugs might have some harmful hazardous fumes in its air chamber that should be prevented from being released into the ambiance. Thus, as the operation of the first valve is associated with the operation of the syringe that is used to withdraw the saline water from the IV bag, by controlling the operation of the first valve, the operation of the syringe can be controlled, as described later herein below.

The first valve can comprise a first valve seating member at least partially defining a first valve passage being in fluid communication with the air channel at said first valve open state, and a first valve sealing member engaging the first valve seating member at said first valve normally closed state thereby sealing said first valve passage.

At the first valve open state, the first valve sealing member can at least partially disengage from the first valve seating member thereby unsealing the first valve passage.

In some examples, at the first valve open state, the first valve sealing member can completely disengage from the first valve seating member thereby unsealing the first valve passage.

The first valve passage can define at least a portion of a first fluid path extending between the air channel and the ambiance, the first fluid path being selectively sealable by the first valve at the first valve normally closed state.

The first valve, at the first valve normally closed state, can seal the first fluid path, and at the first valve open state, can unseal the first fluid path to allow air in the air channel to escape into the ambiance.

The adaptor can further comprise a second valve in fluid communication with the air channel, and having a second valve open state at which it allows air to enter into the air channel from the ambiance, and a second valve normally closed state.

The second valve can be configured to automatically displace into the second valve open state in response to air pressure within the air channel falling below a second pre-determined threshold lesser than the first predetermined threshold. The second valve can be configured to automatically displace into the second valve closed state in response to air pressure within the air channel exceeding the second pre-determined threshold.

The second valve is particularly in operation in association with a syringe that is used to deliver the drug to the IV bag through the adaptor.

The second valve can comprise a second valve seating member having a second valve passage being in fluid communication with the air channel at said second valve open state, and a second valve sealing member engaging the second valve seating member at said second valve normally closed state thereby sealing said second valve passage.

At the second valve open state, the second valve sealing member can at least partially disengage from the second valve seating member thereby unsealing the second valve passage.

In some examples, at the second valve open state, the second valve sealing member can completely disengage from the second valve seating member thereby unsealing the second valve passage.

The second valve passage can define at least a portion of a second fluid path extending between the air channel and the ambiance, the second fluid path being selectively sealable by the second valve at the second valve normally closed state.

The second valve, at the second valve normally closed state, can seal the second fluid path, and at the second valve open state, can unseal the second fluid path to allow air to enter in the air channel from the ambiance.

The first valve and the second valve can be positioned within a single common valve housing. In some examples, the valve housing can be integrally formed within the adaptor. In other examples, the valve housing can be separately formed and mounted to the adaptor. The valve housing can constitute a portion of the adaptor, whereas, the valve housing can include one or more parts of the adaptor otherwise and additionally configured for different purposes. In other words, the first and the second valves can be positioned within the adaptor so as to coordinate with each other in such a way to operate as a common valve and the portion of the adaptor including such common valve constitutes the valve housing. In other examples, the valve housing can be distinct from the adaptor and can be mounted to the adaptor.

The first valve and the second valve can be integrated as a single valve arrangement. The valve arrangement can comprise the first and the second sealing members configured as a single integrated sealing member configured to displace the valve arrangement into a first valve open state at which it allows the air in the air channel to escape into the ambiance, a second valve open state at which it allows air to enter into the air channel from the ambiance, and a normal fully closed state.

The valve arrangement can be normally at the normal fully closed state, wherein the valve arrangement automatically displaces into the first valve open state in response to an air pressure within the valve arrangement rising above the first predetermined threshold, wherein the valve arrangement automatically displaces into the second valve open state in response to the air pressure within the valve arrangement falling below the second predetermined threshold. The first predetermined threshold can be greater than the second predetermined threshold. The valve arrangement can automatically displace into the normal fully closed state in response to the air pressure within the valve arrangement being within the first predetermined threshold and the second predetermined threshold.

The sealing member can be monolithic.

The valve arrangement can further comprise the first valve seating member and the second valve seating member, the single integrated sealing member having a sealing member first portion configured to selectively engage and at least partially disengage the first valve seating member thereby selectively sealing and unsealing the first valve passage, and a sealing member second portion configured to selectively engage and at least partially disengage the second valve seating member thereby selectively sealing and unsealing the second valve passage.

The coordination of the sealing member first portion and the first valve seating member operates as the first valve, and the coordination of the sealing member second portion and the second valve seating member operates as the second valve.

At the normal fully closed state, the sealing member first portion engages with the first valve seating member thereby sealing the first valve passage and the sealing member second portion engages with the second valve seating member thereby sealing the second valve passage;
  at the first valve open state, the sealing member first portion at least partially disengages from the first valve seating member thereby unsealing the first valve passage, wherein at the first valve open state, the sealing member second portion engages with the second valve seating member, thereby sealing the second valve passage; and
  at the second valve open state, the sealing member second portion at least partially disengages from the second valve seating member thereby unsealing the second valve passage, wherein at the second valve open state, the sealing member first portion engages with the first valve seating member, thereby sealing the first valve passage.

At the first valve open state, the valve arrangement can allow the air to escape from within the valve arrangement to outside the valve arrangement via the first valve passage, and at the second valve open state, the valve arrangement can allow the air to enter into the valve arrangement from outside the valve arrangement via the second valve passage.

In some examples, the valve arrangement can be configured to facilitate exchange of air between within the valve arrangement and the ambiance. The valve arrangement can be used with a fluid transfer system where pressure needs to be maintained within a range. In such a system, the air pressure needs to be allowed to flow inwards from the ambiance in case of the same falling below a first predetermined threshold, and be allowed to flow outwards to the ambiance in case of the same rising above a second predetermined threshold. The valve arrangement can be used with such a fluid transfer system so as to have the valve arrangement in fluid communication with the system to exchange the air pressure between therewithin and the ambiance.

According to a first specific example of the sixth aspect of the presently disclosed subject matter, at the first valve open state, the sealing member second portion engages with the second valve seating member further tighter as compared to that at the normally fully closed state; and at the second valve open state, the sealing member first portion engages with the first valve seating member further tightly as compared to that at the normally fully closed state.

The sealing member first portion and the sealing member second portion can be positioned at opposite ends of the sealing member.

The adaptor can further comprise a first outlet in fluid communication with the first valve and the ambiance, wherein the first outlet can be configured to receive therewithin a lever button operational to disconnect the adaptor from an external female connector. In some examples, the first valve can utilize an opening in the adaptor otherwise and additionally configured for another purpose, to facilitate exchange of air between the ambiance and the air channel.

The first fluid path can extend via the first outlet.

The adaptor can further comprise a second outlet in fluid communication with the second valve and the ambiance, wherein the second outlet can be an opening formed in a sidewall of an outer body of a luer lock connection port constituting a proximal end of the adaptor.

The second fluid path can extend via the second outlet.

In some examples, the sealing member can be monolithic. In other examples, the first and the second sealing member portions can be separately formed and connected to each other.

In some examples, the sealing member can include a central portion having a first end constituting the sealing member first portion and a second end, wherein a resilient skirt portion can extend from a periphery of the second end, the skirt portion being defined between a first rim proximal to the second end and a second rim distal from the second end. The skirt portion can have an external surface facing the second valve seating member and an opposite internal surface. At the normal fully closed state, the second rim can engage the second valve seating member around the second valve passage, whereas maintaining a gap between the first rim and the second valve seating member, and the first end of the central portion can engage the first valve seating member. In this state, the volume defined between the central portion, the internal surface of the skirt portion, internal walls of the valve arrangement, the first valve seating member, and the second valve seating member defines the volume within the valve arrangement. In response to an increase in air pressure beyond the first predetermined threshold within the valve arrangement, the pressure exerted on the internal surface of the skirt member can cause the second end of the central member to be compressed into the gap between the second end and the second valve seating member, thereby disengaging the first end from the first valve seating member, further thereby unsealing the first valve passage. The increased air pressure can thus get released from within the valve arrangement into the ambiance via the first valve passage.

In response to a decrease in air pressure below the second predetermined threshold within the valve arrangement, the second rim can disengage from the second valve seating member, thereby unsealing the second valve passage.

According to a second specific example of the sixth aspect of the presently disclosed subject matter, the second valve seating member can comprise a valve seat having a valve seat opening, and the first valve seating member can comprise a central member extending through the valve seat opening, the sealing member being positioned at least partially within the valve seat opening and radially between the valve seat and the central member. In some examples, the central member can extend axially through the valve seat opening.

The sealing member first portion can be configured to selectively engage and at least partially disengage the central member thereby selectively displacing the valve arrangement into its first valve open state allowing the air to pass through the first valve passage defined between the central member and the sealing member, and the sealing member second portion is configured to selectively engage and at least partially disengage the valve seat thereby selectively displacing the valve arrangement into its second valve open state allowing the air to pass through the second valve passage defined between the valve seat and the sealing member. In some examples, the sealing member can comprise a longitudinal member extending axially through the valve seat opening, the sealing member first portion can extend radially from the longitudinal member towards the central member, and the sealing member second portion can extend radially from the longitudinal member towards the valve seat.

The valve seat can have a valve seat internal surface facing the air channel, and an opposite valve seat external surface, wherein the sealing member second portion engages the valve seat internal surface, the sealing member further comprising a sealing member third portion having a fixing member configured to engage the external surface of the valve seat, thereby holding the sealing member in its position. In some examples, the fixing member can extend radially from the longitudinal member towards the valve seat and engages the external surface of the valve seat. The sealing member second portion and the fixing member engaging the valve seat holds the sealing member in its position relative to the valve seat. When the sealing member second portion disengages the valve seat, the fixing member engaging the valve seat external surface prevents axial displacement of the sealing member.

The adaptor can further comprise an actuator configured to selectively switch the adaptor between a fully operational state at which the adaptor is fully operable for transfer of liquid through the liquid channel, and an at least partial inoperational state at which the adaptor is at least partially inoperable for said transfer of liquid through the liquid channel. As also described above, the adaptor can be a dual function adaptor, i.e., the adaptor can be configured to facilitate the transfer of liquid in two directions. The adaptor can be configured to be used to withdraw a liquid from an external container into a syringe as well as to inject a liquid from within a syringe into an external container. The fully operational state of the adaptor has been herein referred to as a state in which the adaptor can be used in conjunction with a syringe to withdraw a liquid from as well as inject a liquid into an external container, the two syringes generally being different. The at least partial inoperational state of the adaptor has been herein referred to as a state in which the adaptor cannot be used in conjunction with a syringe for at least one of withdrawing a liquid from or delivering a liquid into an external container. In one specific example described herein, the at least partial inoperational state of the adaptor has been referred to as a state in which the adaptor can be used in conjunction with a syringe to deliver a liquid into an external container and cannot be used to withdraw a liquid from an external container into the syringe.

According to the specific example in which the adaptor is a spike adaptor, and can be used in conjunction with a syringe for withdrawing saline water from an IV bag as well as to deliver drug into the IV bag. As described above the protocol can require a medical practitioner to use a new/unused syringe for withdrawing the saline water from the IV bag. The adaptor can be configured to be selectively at its at least partial operational state so as to act as a reminder for the practitioner that a new syringe needs to be used for withdrawing the saline water from the IV bag. For instance, the adaptor can be configured to be normally at its at least partial inoperational state at which the flow of the liquid through the adaptor in the direction from the IV bag to the syringe is blocked. Thus, when the practitioner would want to use the adaptor for the purpose of withdrawing the saline water from the IV bag into the syringe, the adaptor would be required to be manually switched into its fully operational state by the practitioner using the actuator, thereby preventing the practitioner to accidentally and carelessly use an already used syringe for the purpose, and reminding the practitioner that as the adaptor is switched to its fully operational state, a new syringe is to be used.

In some examples, at the at least partial inoperational state, the actuator can be configured to at least partially block the transfer of liquid through the liquid channel indirectly. The adaptor can be configured to prevent the transfer of liquid through the liquid channel in one direction indirectly by controlling the passage of air between the ambiance and the air channel. The flow of liquid depends upon the discharge and intake of air from and into the air chamber of the syringe via the air channel. Thus, by controlling the passage of air through the air channel, the transfer of liquid can be indirectly controlled.

The transfer of fluid through the liquid channel at least partially depends upon passage of air through the first valve, and the actuator is configured to selectively prevent said passage of air thereby displacing the adaptor into its at least partial inoperational state and thereby indirectly at least partially blocking the transfer of liquid through the liquid channel.

At the fully operational state, the adaptor is operable for the transfer of liquid through the liquid channel in a first direction and an opposite second direction, and at the at least partial inoperational state, the adaptor is inoperable for transfer of liquid through the liquid channel in at least one of first and the second direction.

The transfer of liquid through the liquid channel in the first direction depends upon discharge of air from within the adaptor through the first valve, and at the at least partial inoperational state, the actuator prevents said discharge of air thereby rendering the adaptor inoperable for the transfer of liquid through the liquid channel in the first direction. In some examples, the first direction can be from the IV bag towards the syringe and the second direction can be from the syringe towards the IV bag.

The transfer of liquid through the liquid channel in the second direction can depend upon intake of air into the adaptor through the first valve, and at the at least partial inoperational state, the actuator prevents said intake of air thereby rendering the adaptor inoperable for the transfer of liquid through the liquid channel in the second direction.

In some examples, at the at least partial inoperational state, the actuator can be configured to at least partially block the transfer of liquid through the liquid channel directly.

The actuator can have a first actuator state associated with the fully operational state of the adaptor, and a second actuator state associated with the at least partial inoperational state of the adaptor. For instance, when the actuator is at its first actuator state, the adaptor can be at its fully operational state and when the actuator is at its second actuator state, the adaptor can be at its at least partial inoperational state.

The actuator can be displaceable between the first actuator state and the second actuator state upon application of an external force. The external force can be a pushing force, a pulling force, a rotational force, or a combination of a push/pull and rotational force.

In some examples, the actuator can be configured to remain in each of the first and the second actuator states upon removal of the external force. For instance, the actuator can be a switch configured to be selectively switched into the first or the second actuator state and retain that state until switched again.

In some examples, the actuator can be configured to be normally at one of the first and the second actuator state and is configured to be displaced into other one of the first and the second actuator state upon application of the external force, and to automatically return to said one of the first and the second actuator state upon removal of the external force. For instance, the actuator can be a biased button configured to be biased to stay normally in one of the first and the second actuator states. Upon application of an external force, the button can be configured to be displaced into other one of the first and the second actuator states and then return, due to the biasing force, into the normal one of the first and the second actuator state upon removal of said external force.

The actuator can be configured to be normally at the second actuator state, and is configured to be displaced into the first actuator state upon application of the external force, and to automatically return to the second actuator state upon removal of the external force. In a specific example, the actuator configured as a biased button can be configured to be normally at the second actuator state, i.e., so as to maintain the adaptor in its at least partial inoperational state, thereby preventing the discharge of the air from within the air channel into the ambiance. Upon application of the external force, the button displaces into its first actuator state thereby displacing the adaptor into its fully operational state and allowing the air to discharge from the air channel into the ambiance. Upon removal of said external force, the button returns to its second actuator state thereby displacing the adaptor into its at least partial inoperational state.

At the second actuator state, the actuator can be configured to engage the sealing member third portion and to prevent the passage of air from between the central member and the sealing member, thereby disabling the discharge of air from the valve arrangement irrespective of the state of the valve arrangement. In a specific example, the actuator configured as a switch can be configured to engage the fixing member constituting the sealing member third portion thereby blocking the passage of air from between the central member and the sealing member, thereby disabling the discharge of air from the adaptor irrespective of the valve arrangement being at the first valve open state.

According to a seventh aspect of the presently disclosed subject matter, there is provided a valve arrangement comprising:

a sealing member configured to displace the valve arrangement into a first valve open state at which it allows air to escape from within the valve arrangement into ambiance, a second valve open state at which it allows air to enter into the valve arrangement from the ambiance, and a normal fully closed state.

The valve arrangement can be normally at the normal fully closed state, wherein the sealing member automatically displaces the valve arrangement into the first valve open state in response to an air pressure within the valve arrangement rising above a first predetermined threshold, into the second valve open state in response to the air pressure within the valve arrangement falling below a second predetermined threshold. The sealing member automatically displaces the valve arrangement into the normal fully closed state in response to the air pressure within the valve arrangement being within the first predetermined threshold and the second predetermined threshold. The first predetermined threshold is greater than the second predetermined threshold.

The valve arrangement can further comprise a first valve seating member at least partially defining a first valve passage and a second valve seating member at least partially defining a second valve passage, the sealing member having a sealing member first portion configured to selectively engage and at least partially disengage the first valve seating member thereby selectively sealing and unsealing the first valve passage, and a sealing member second portion configured to selectively engage and at least partially disengage the second valve seating member thereby selectively sealing and unsealing the second valve passage.

At the normal fully closed state, the sealing member first portion engages with the first valve seating member thereby sealing the first valve passage and the sealing member second portion engages with the second valve seating member thereby sealing the second valve passage;

at the first valve open state, the sealing member first portion at least partially disengages from the first valve seating member thereby unsealing the first valve passage, wherein at the first valve open state, the sealing member second portion engages with the second valve seating member, thereby sealing the second valve passage; and at the second valve open state, the sealing member second portion at least partially disengages from the second valve seating member thereby unsealing the second valve passage, wherein at the second valve open state, the sealing member first portion engages with the first valve seating member, thereby sealing the first valve passage.

At the first valve open state, the valve arrangement can allow the air to escape from within the valve arrangement to outside the valve arrangement via the first valve passage, and at the second valve open state, the valve arrangement can allow the air to enter into the valve arrangement from outside the valve arrangement via the second valve passage.

In some examples, the valve arrangement can be configured to facilitate exchange of air between within the valve arrangement and the ambiance. The valve arrangement can be used with a fluid transfer system where pressure needs to be maintained within a range. In such a system, the air pressure needs to be allowed to flow inwards from the ambiance in case of the same falling below a first predetermined threshold, and be allowed to flow outwards to the ambiance in case of the same rising above a second predetermined threshold. The valve arrangement can be used with such a fluid transfer system so as to have the valve arrangement in fluid communication with the system to exchange the air pressure between therewithin and the ambiance.

According to a first specific example of the seventh aspect of the presently disclosed subject matter, at the first valve open state, the sealing member second portion engages with the second valve seating member further tighter as compared to that at the normally fully closed state; and at the second valve open state, the sealing member first portion engages with the first valve seating member further tightly as compared to that at the normally fully closed state.

The sealing member first portion and the sealing member second portion can be positioned at opposite ends of the sealing member.

In some examples, the sealing member can be monolithic. In other examples, the first and the second sealing member portions can be separately formed and connected to each other.

In some examples, the sealing member can include a central portion having a first end constituting the sealing member first portion and a second end, wherein a resilient skirt portion can extend from a periphery of the second end, the skirt portion being defined between a first rim proximal to the second end and a second rim distal from the second end. The skirt portion can have an external surface facing the second valve seating member and an opposite internal surface. At the normal fully closed state, the second rim can engage the second valve seating member around the second valve passage, whereas maintaining a gap between the first rim and the second valve seating member, and the first end of the central portion can engage the first valve seating member. In this state, the volume defined between the central portion, the internal surface of the skirt portion, internal walls of the valve arrangement, the first valve seating member, and the second valve seating member defines the volume within the valve arrangement. In response to an increase in air pressure beyond the first predetermined threshold within the valve arrangement, the pressure exerted on the internal surface of the skirt member can cause the second end of the central member to be compressed into the gap between the second end and the second valve seating member, thereby disengaging the first end from the first valve seating member, further thereby unsealing the first valve passage. The increased air pressure can thus get released from within the valve arrangement into the ambiance via the first valve passage.

In response to a decrease in air pressure below the second predetermined threshold within the valve arrangement, the second rim can disengage from the second valve seating member, thereby unsealing the second valve passage.

According to a second specific example of the seventh aspect of the presently disclosed subject matter, the second valve seating member can comprise a valve seat having a valve seat opening, and the first valve seating member can comprise a central member extending through the valve seat opening, the sealing member being positioned at least partially within the valve seat opening and radially between the valve seat and the central member. In some examples, the central member can extend axially through the valve seat opening.

The sealing member first portion can be configured to selectively engage and at least partially disengage the central member thereby selectively displacing the valve arrangement into its first valve open state allowing the air to pass through the first valve passage defined between the central member and the sealing member, and the sealing member second portion is configured to selectively engage and at least partially disengage the valve seat thereby selectively displacing the valve arrangement into its second valve open state allowing the air to pass through the second valve passage defined between the valve seat and the sealing member. In some examples, the sealing member can comprise a longitudinal member extending axially through the valve seat opening, the sealing member first portion can extend radially from the longitudinal member towards the central member, and the sealing member second portion can extend radially from the longitudinal member towards the valve seat.

The valve seat can have a valve seat internal surface facing the air channel, and an opposite valve seat external surface, wherein the sealing member second portion engages the valve seat internal surface, the sealing member further comprising a sealing member third portion having a fixing member configured to engage the external surface of the valve seat, thereby holding the sealing member in its position. In some examples, the fixing member can extend radially from the longitudinal member towards the valve seat and engages the external surface of the valve seat. The sealing member second portion and the fixing member engaging the valve seat holds the sealing member in its position relative to the valve seat. When the sealing member second portion disengages the valve seat, the fixing member engaging the valve seat external surface prevents axial displacement of the sealing member.

In some examples, the first predetermined threshold and/or the second predetermined threshold is obtained based on the geometry, design, or material of the valves and their surrounding parts. In some examples, the first predetermined threshold can have a single value of 0.3 bar and the second predetermined threshold can have a single value of 0.03 bar.

The valve arrangement can further comprise an actuator configured to control the flow of the air through the valve arrangement. The actuator can be configured to switch the valve arrangement into at least one of the first valve open state and the second valve open state from the normal fully closed state upon application of an external force. The actuator can be configured to selectively prevent the flow of air through the valve arrangement irrespective of the state of the valve arrangement. The adaptor according to the seventh aspect can include some or all the features of the adaptor as described above according to the sixth aspect of the presently disclosed subject matter.

It is to be understood herein that the valve arrangement, as described above with respect to the seventh aspect, can be used with any fluid transfer apparatus that requires an air pressure to be maintained within a range. Also, the valve arrangement as described above with respect to the seventh aspect can be a dual function valve and can be used with the adaptor as described above with respect to the sixth aspect of the presently disclosed subject matter, wherein the first valve and the second valve (of the sixth aspect) can be combined to be realized as the dual function valve arrangement of the seventh aspect of the presently disclosed subject matter, in which the coordination between the sealing member first portion and the first valve seating member acts as the first valve and the coordination between the sealing member second portion and the second valve seating member acts as the second valve.

It should be understood herein that the application of the dual function valve is advantageous over application of two valves, in that, a single sealing member needs to be manufactured and assembled instead of two separate sealing members. Further, the single valve arrangement occupies lesser space than the two separate valves within the housing of the adaptor.

According to an eighth aspect of the presently disclosed subject matter, there is provided an adaptor comprising:
- a liquid channel configured for facilitating transfer of liquid therethrough;
- an actuator configured to selectively switch the adaptor between a fully operational state at which the adaptor is fully operable for said transfer of liquid, and an at least partial inoperational state at which the adaptor is at least partially inoperable for said transfer of liquid.

In some examples, at the at least partial inoperational state, the adaptor can be configured to indirectly block the transfer of liquid through the liquid channel by blocking another passage through the adaptor, for example, an air channel of the adaptor in communication with an air chamber of a syringe which is not in fluid communication with the ambiance other than via an air needle that can be in fluid communication with the ambiance through the air channel of the adaptor. The adaptor can be a dual function spike adaptor similar to the one described above, and can be configured to facilitate the transfer of liquid in two directions. The adaptor can be configured to be used to withdraw a liquid from an external container into a syringe as well as to inject a liquid from within a syringe into an external container. The fully operational state of the adaptor has been herein referred to as a state in which the adaptor can be used in conjunction with a syringe to withdraw a liquid from as well as inject a liquid into an external container. The at least partial inoperational state of the adaptor has been herein referred to as a state in which the adaptor cannot be used in conjunction with a syringe to at least one of withdrawing a liquid from or injecting/delivering a liquid into an external container.

In those examples when, at the at least partial inoperational state, the actuator is configured to at least partially block the transfer of liquid through the liquid channel indirectly, the adaptor can further comprise an air channel configured for facilitating passage of air therethrough, wherein the transfer of liquid through the liquid channel at least partially depends upon the passage of air through the air channel, and the actuator is configured to selectively prevent said passage of air thereby displacing the adaptor into its at least partial inoperational state and at least partially blocking the transfer of liquid through the liquid channel. The adaptor can be configured to prevent the transfer of liquid through the liquid channel in one direction indirectly by controlling the passage of air between the ambiance and the air channel of the adaptor. The flow of liquid depends upon the discharge and intake of air from and into the air chamber of the syringe via the air channel. Thus, by controlling the passage of air through the air channel, the transfer of liquid can be indirectly controlled.

At the fully operational state, the adaptor is operable for the transfer of liquid through the liquid channel in a first direction and a second direction, and at the at least partial inoperational state, the adaptor is inoperable for transfer of liquid through the liquid channel in at least one of first and the second direction.

The transfer of liquid through the liquid channel in the first direction can depend upon discharge of air from within the adaptor through the air channel, and at the at least partial inoperational state, the actuator prevents said discharge of air thereby rendering the adaptor inoperable for the transfer of liquid through the liquid channel in the first direction.

The transfer of liquid through the liquid channel in the second direction can depend upon intake of air into the adaptor, and at the at least partial inoperational state, the actuator prevents said intake of air thereby rendering the adaptor inoperable for the transfer of liquid through the liquid channel in the second direction.

In some examples, the first direction can be from the IV bag towards the syringe and the second direction can be from the syringe towards the IV bag.

As described above, for using a single spike adaptor for both the operations, viz a viz, withdrawal of saline water from the IV bag into a syringe and delivery of a drug from a syringe into the IV bag, a new and unused syringe can be required to be used for withdrawal of the saline water from the IV bag through the adaptor, as a part of a protocol. The adaptor can be configured to be at its at least partial operational state so as to act as a reminder for the practitioner that a new syringe needs to be used for withdrawing the saline water from the IV bag. For instance, as also described above, the adaptor can be configured to be normally at its at least partial inoperational state at which the flow of the liquid through the adaptor in the direction from the IV bag to the syringe is blocked. Thus, when the practitioner would want to use the adaptor for the purpose of withdrawing the saline water from the IV bag into the syringe, the adaptor would be required to be manually switched into its fully operational state by the practitioner using the actuator, thereby preventing the practitioner to accidentally and carelessly use an already used syringe for the purpose, and reminding the practitioner that as the adaptor is switched to its fully operational state, a new syringe is to be used.

In some examples, at the at least partial inoperational state, the actuator can be configured to at least partially block the transfer of liquid through the liquid channel directly. The actuator can be directly positioned at least partially within the liquid channel and can selectively block the flow of liquid therethrough. The adaptor can be a luer lock adaptor and the actuator can be configured to block the flow of the liquid in both of the first and the second direction. The actuator can include a flow path which can be configured to be selectively align with the liquid channel. When the flow path is aligned with the liquid channel, the adaptor is in its fully operational state and when the flow path is not aligned with the liquid channel, the adaptor is in its at least partial inoperational state.

The actuator can have a first actuator state associated with the fully operational state of the adaptor, and a second actuator state associated with the at least partial inoperational state of the adaptor. For instance, when the actuator is at its first actuator state, the adaptor can be at its fully operational state and when the actuator is at its second actuator state, the adaptor can be at its at least partial inoperational state.

The actuator can be displaceable between the first actuator state and the second actuator state upon application of an external force. The external force can be a pushing force, a pulling force, a rotational force, or a combination of a push/pull and rotational force.

In some examples, the actuator can be configured to remain in each of the first and the second actuator states upon removal of the external force. For instance, the actuator can be a switch configured to be selectively switched into the first or the second actuator state and retain that state until switched again.

In some examples, the actuator can be configured to be normally at one of the first and the second actuator state and is configured to be displaced into other one of the first and the second actuator state upon application of the external force, and to automatically return to said one of the first and the second actuator state upon removal of the external force. For instance, the actuator can be a biased button configured to be biased to stay normally in one of the first and the second actuator states. Upon application of an external force, the button can be configured to be displaced into other one of the first and the second actuator states and then return, due to the biasing force, into the normal one of the first and the second actuator state upon removal of said external force.

The actuator can be configured to be normally at the second actuator state, and is configured to be displaced into the first actuator state upon application of the external force, and to automatically return to the second actuator state upon removal of the external force. In a specific example, the actuator configured as a biased button can be configured to be normally at the second actuator state, i.e., so as to maintain the adaptor in its at least partial inoperational state, thereby preventing the discharge of the air from within the air channel into the ambiance. Upon application of the external force, the button displaces into its first actuator state thereby displacing the adaptor into its fully operational state and allowing the air to discharge from the air channel into the ambiance. Upon removal of said external force, the button returns to its second actuator state thereby displacing the adaptor into its at least partial inoperational state.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 3I is an enlarged view of section A5 of FIG. 3H;

FIG. 7E is cross-sectional view along line J-J in FIG. 7D;

DETAILED DESCRIPTION OF EMBODIMENTS

Figure 1A:
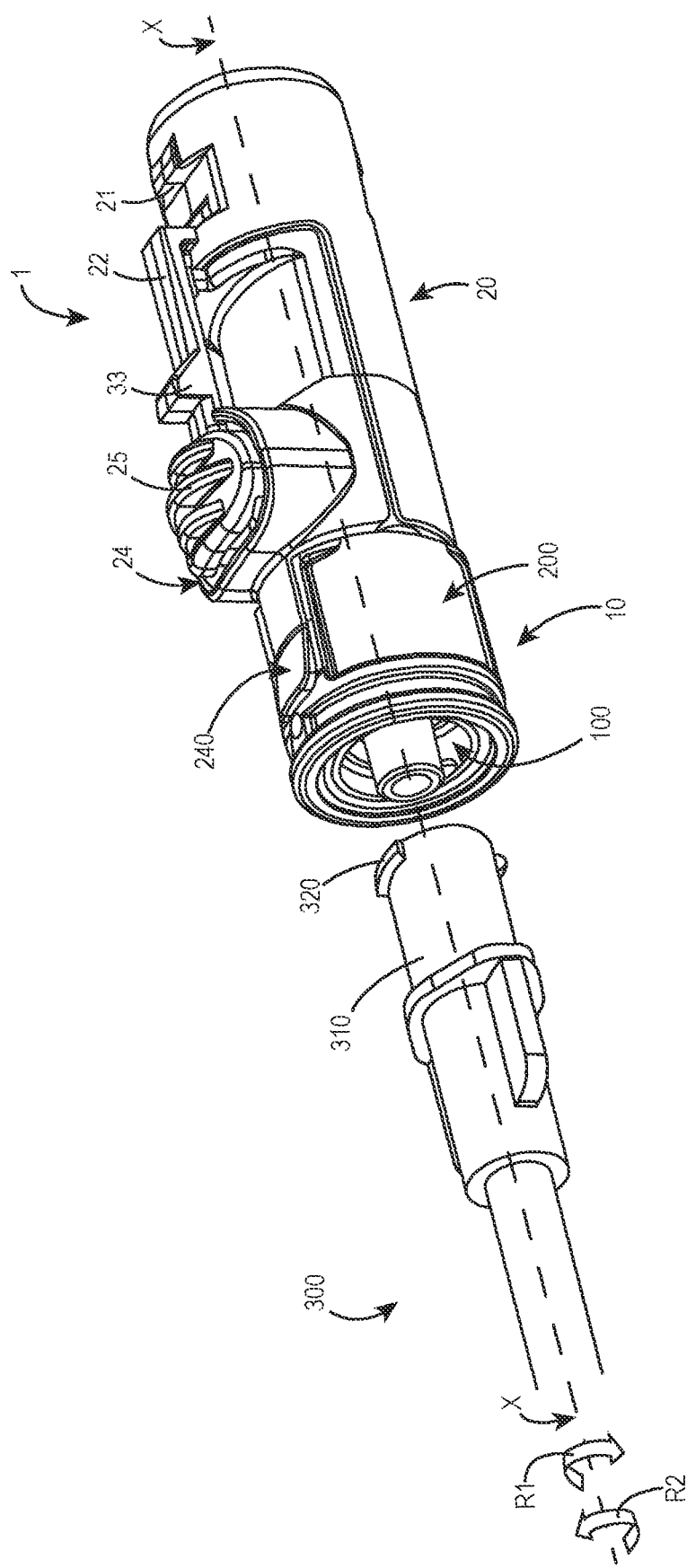
FIG. 1A is a front perspective view of an adaptor according to a first example of the presently disclosed subject matter along with a fluid transfer device disconnected from each other.
Figure 1B:
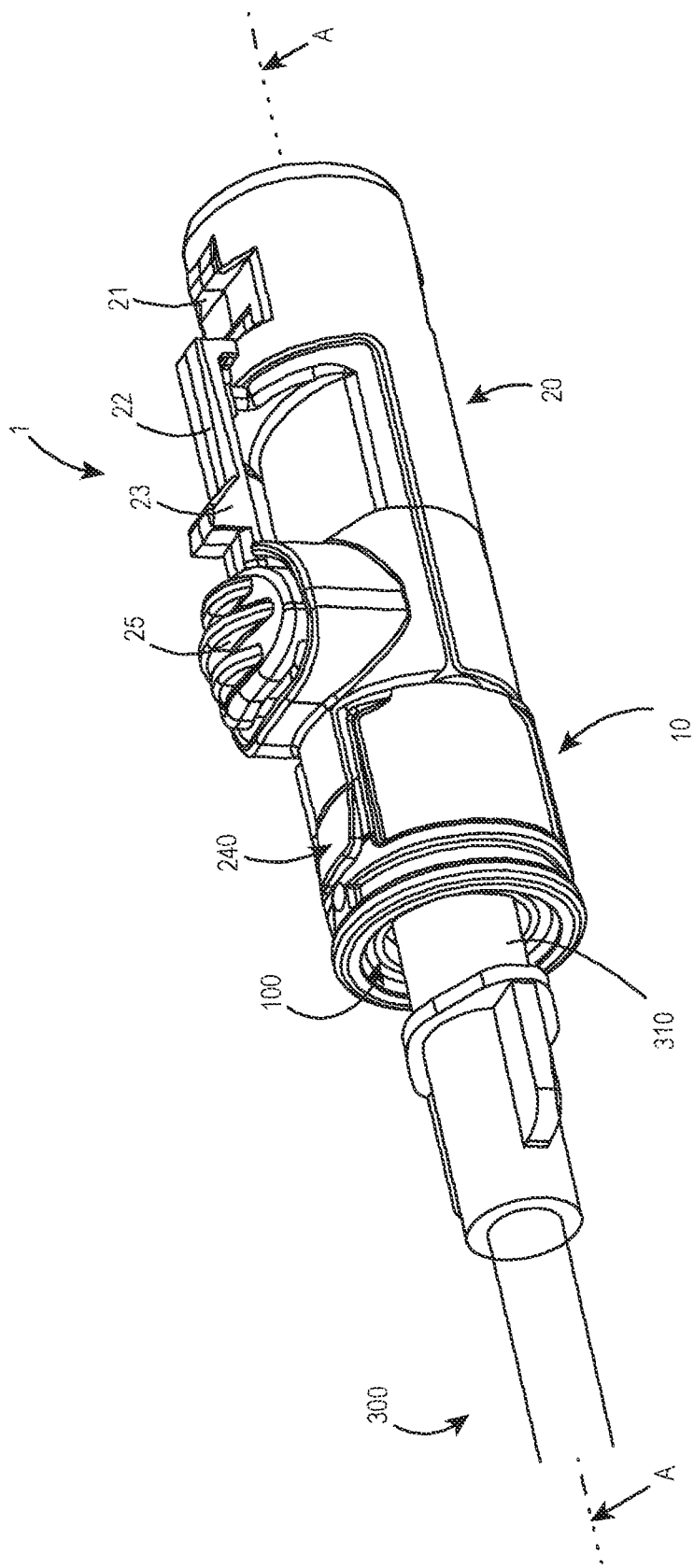
FIG. 1B is a front perspective view of the adaptor and the fluid transfer device of FIG. 1A connected to each other.
Figure 1C:
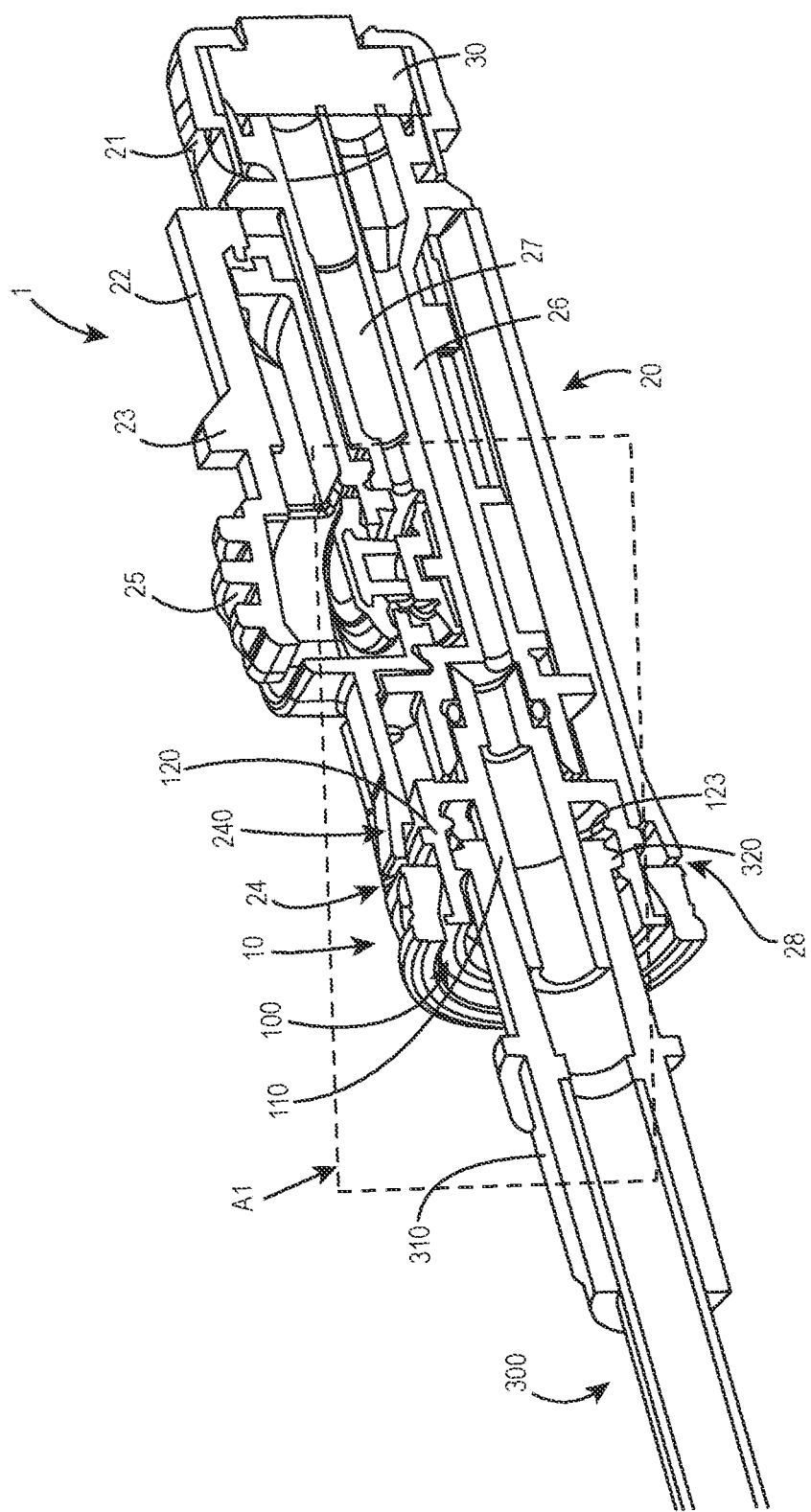
FIG. 1C is a cross-sectional view along line A-A in FIG. 1B, illustrating the adaptor in its decoupling disabled state.

Attention is first directed to FIGS. 1A-1C of the drawings illustrating an adaptor 1 according to one example of the presently disclosed subject matter, configured for connection with a fluid transfer device 300. The fluid transfer device 300 is a known in the art luer lock connection device comprising an external port 310 which is a female luer lock connection port. The external port 310 comprises threads 320 configured to be threaded to corresponding threads of another luer lock connection port. The adaptor 1 comprises a connector 10 having a luer lock connection port 100 and an outer body 200. The adaptor further comprises a housing 20 extending along a longitudinal axis X. In the illustrated example, the outer body 200 and the housing 20 are integrally formed, and eventually, the outer body 200 constitutes part of the housing 20. However, in some other examples (not shown), the outer body 200 and the housing 20 can be separately manufactured and then connected to each other. In some examples, the housing 20 can be manufactured in more than two parts and then assembled together.

As shown in FIGS. 1B and 1C, the connector 10 and the external port 310 are connected to each other, thereby connecting the adaptor 1 and the fluid transfer device 300 together. The connector 10 is a male luer lock connector configured to receive the corresponding external port 310, i.e, the female luer lock connector of the fluid transfer device 300. The luer lock connection port 100 of the connector 10 is positioned within the outer body 200 and has a longitudinal axis X, which is also the longitudinal axis of the adaptor 1. The luer lock connection port 100 is rotatable about the longitudinal axis X in either or both of a clockwise direction, represented by arrow R1 in FIG. 1A, and a counter-clockwise direction, represented by arrow R2 in FIG. 1A, prior to initiation of coupling with the fluid transfer device 300, as shown in FIG. 1A. The luer lock connection port 100 is so placed in the outer body 200, and the outer body 200 is so structured as shown in FIGS. 1A-1C that an operator cannot access the luer lock connection port 100 through the outer body 200 directly by fingertips after the luer lock connection port 100 has been coupled to the external port 310. The luer lock connection port 100 is rotatable in the clockwise direction and the counter-clockwise direction upon coupling thereof with the fluid transfer device 300.

As the luer lock connection port 100 is configured to rotate within the outer body 200, thus, in order to couple and decouple the connector with or from the fluid transfer device 300, the rotation of the luer lock connection port 100 needs to be restricted to enable the coupling and decoupling. The connector 10 comprises a coupling facilitating mechanism configured to assume a coupling enabled state to restrict the rotation of the luer lock connection port 100 in the clockwise direction to enable coupling of the connector 10 with the fluid transfer device 300, and a coupling disabled state in which it allows the rotation of the luer lock connection port in the clockwise direction, explained in detail later herein below with reference to FIGS. 3A to 3I. The connector 10 further comprises a decoupling facilitating mechanism configured to assume a decoupling enabled state to restrict the rotation of the luer lock connection port 100 in the counter-clockwise direction to enable decoupling of the connector 10 from the fluid transfer device 300, and a decoupling disabled state in which it allows the rotation of the luer lock connection port in the counter-clockwise direction, explained in detail later herein below with reference to FIGS. 4A to 4F.

It is to be understood herein that the directions clockwise and counter-clockwise have been referred to for the purposes of this description as being seen from the direction of the fluid transfer device 300 into the connector 10 along the longitudinal axis X.

Figure 2A:
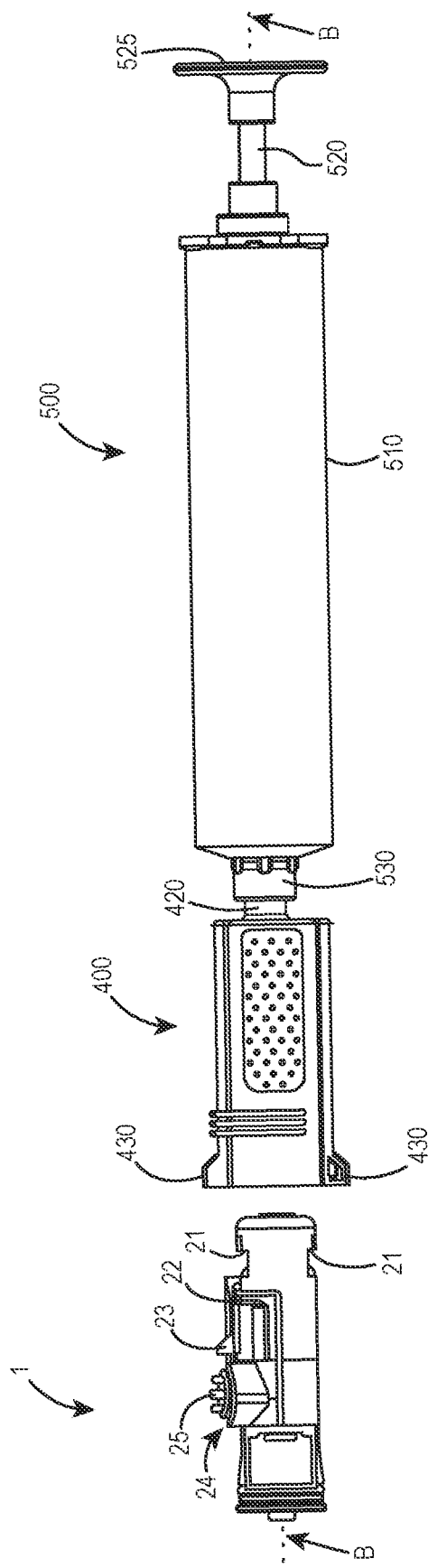
FIG. 2A is a side view of the adaptor of FIG. 1A along with a syringe and a syringe adaptor connected to each other, but disconnected from the adaptor.

Attention is now directed to FIGS. 2A-2E of the drawings illustrating the adaptor 1 along with a syringe adaptor 400 and a syringe 500. FIG. 2A illustrates the syringe adaptor 400 and the syringe 500 connected to each other, and the adaptor 1 not connected to the syringe adaptor 400. The syringe 500 is a known in the art syringe used for drug mixing, and adapted to draw a desired volume of a drug from one container and to subsequently transfer the drug to a second container. The syringe 500 comprises a cylinder 510, a piston rod 520 having a cap 525, and a throat 530. The piston rod 520 extends from the cap 525 to a piston 540, which sealingly engages the inner wall of, and is displaceable with respect to, the cylinder 510. The piston 540 divides an internal volume of the cylinder 510 into two chambers having variable volumes defined by position of the piston 540 within the cylinder 510—an air chamber 550 and a liquid chamber 560. The piston rod 520 has an internal volume 570, which is in fluid communication with the air chamber 550 through a hole 580 formed in the piston rod 510, thereby rendering the internal volume 570 a part of the air chamber 550. The syringe 500 further comprises an air needle 590 extending from the air chamber 550 to an exterior of the syringe via the throat 530.

Figure 2B:
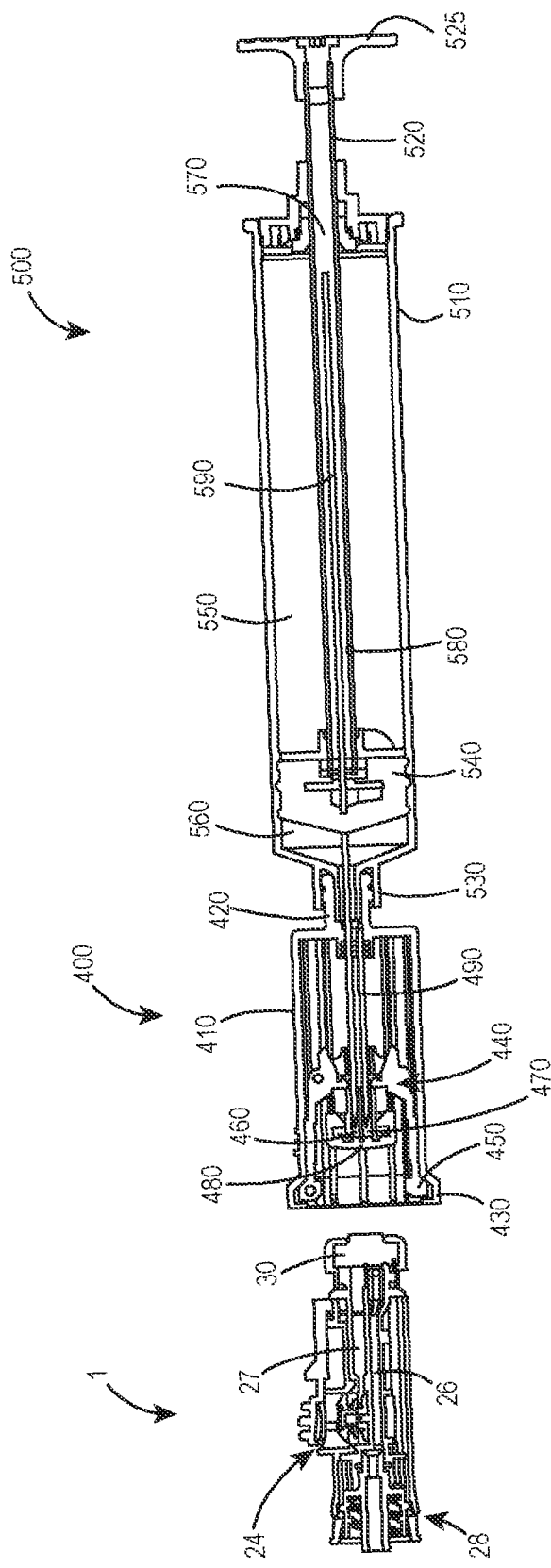
FIG. 2B is a cross-sectional view along line B-B in FIG. 2A.

The syringe adaptor 400 comprises a syringe adaptor body 410 having a neck 420 configured to be connected to the throat 530 of the syringe. In the illustrated example, the throat 530 is a male luer lock connector and the neck 420 is a female luer lock connector, and they are heat-welded to each other. The syringe adaptor body 410 further comprises flanges 430 configured to get locked with a corresponding element of the adaptor 1 when the syringe adaptor 400 is connected to the adaptor 1. The syringe adaptor 400 further comprises an internal locking arrangement 440 comprising leaves 450 configured to get locked with a corresponding element of the adaptor 1 when the syringe adaptor 400 is connected to the adaptor 1. The internal locking arrangement 440 defines an air duct 460 and a liquid duct 470, both the air duct 460 and the liquid duct 470 extending into a septum 480. The air duct 460 is configured to receive the tip of the air needle 590 when the syringe adaptor 400 is connected to the syringe 500 and is not connected to the adaptor 1, as shown in FIG. 2B. The syringe adaptor 400 further comprises a liquid needle 490 in fluid communication with the liquid chamber 560 via the neck 420 and the throat 530 when the syringe adaptor 400 is connected to the syringe 500, and extending from the neck 420 to the liquid duct 470 when the syringe adaptor 400 is not connected to the adaptor 1, as shown in FIG. 2B. In some examples (not shown), the liquid needle 490 can be a part of the syringe 500 extending therefrom.

The adaptor 1 comprises the housing 20 having on an external surface thereof, a notch 21 configured to receive and lock thereto the leaves 450 when the syringe adaptor 400 is connected to the adaptor 1. The housing 20 further comprises a lever 22 having a lever notch 23 configured to receive and lock thereto the flange 430 when the syringe adaptor 400 is connected to the adaptor 1. The housing 20 further comprises a first outlet 24 and the lever 22 comprises a lever button 25 positioned in the first outlet 24. The housing 20 further comprises a liquid channel 26 in fluid communication with the connector 10, and configured to receive therewithin the liquid needle 490 when the syringe adaptor 400 is connected to the adaptor 1. The housing 20 further comprises an air channel 27 configured to receive therewithin the air needle 590 when the syringe adaptor 400, having the syringe 500 connected thereto, is connected to the adaptor 1. The housing 20 further comprises a second outlet 28. The adaptor 1 further comprises a septum 30 configured to engage with the septum 480 and configured to be punctured by the air needle 590 and the liquid needle 490 when the syringe adaptor 400, having the syringe 500 connected thereto, is connected to the adaptor 1. The adaptor 1 further comprises a first valve 40 in fluid communication with the air channel 27, and having a first valve open state at which it allows air in the air channel to escape into ambiance, and a first valve normally closed state, explained in detail later herein below with reference to FIGS. 6A to 6E. The adaptor 1 further comprises a second valve 50 in fluid communication with the air channel 27, and having a second valve open state at which it allows air to enter into the air channel 27 from the ambiance, and a second valve normally closed state, explained in detail later herein below with reference to FIGS. 6A to 6E.

Figure 2C:
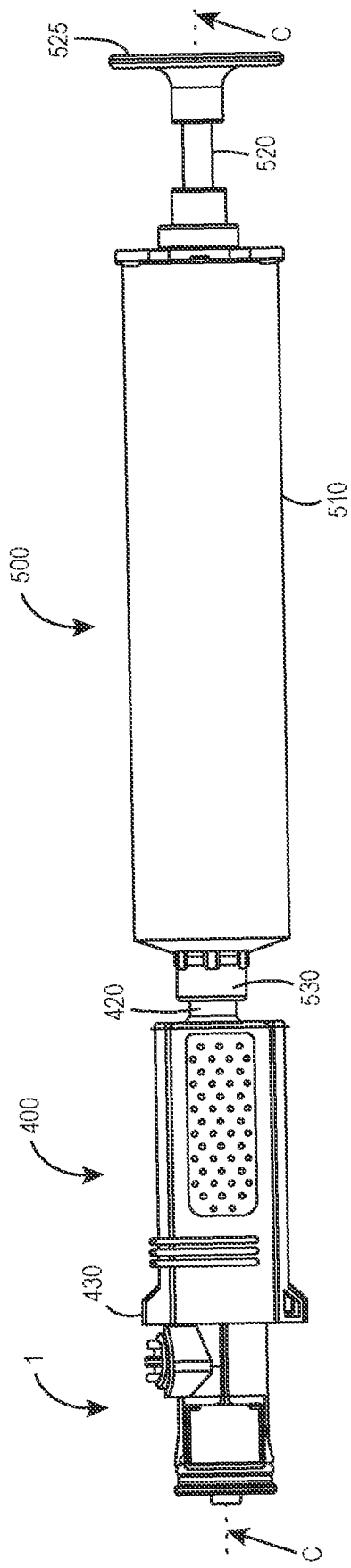
FIG. 2C is a side view of the adaptor, and the syringe and the syringe adaptor of FIG. 2A connected to each other as well as to the adaptor.
Figure 2D:
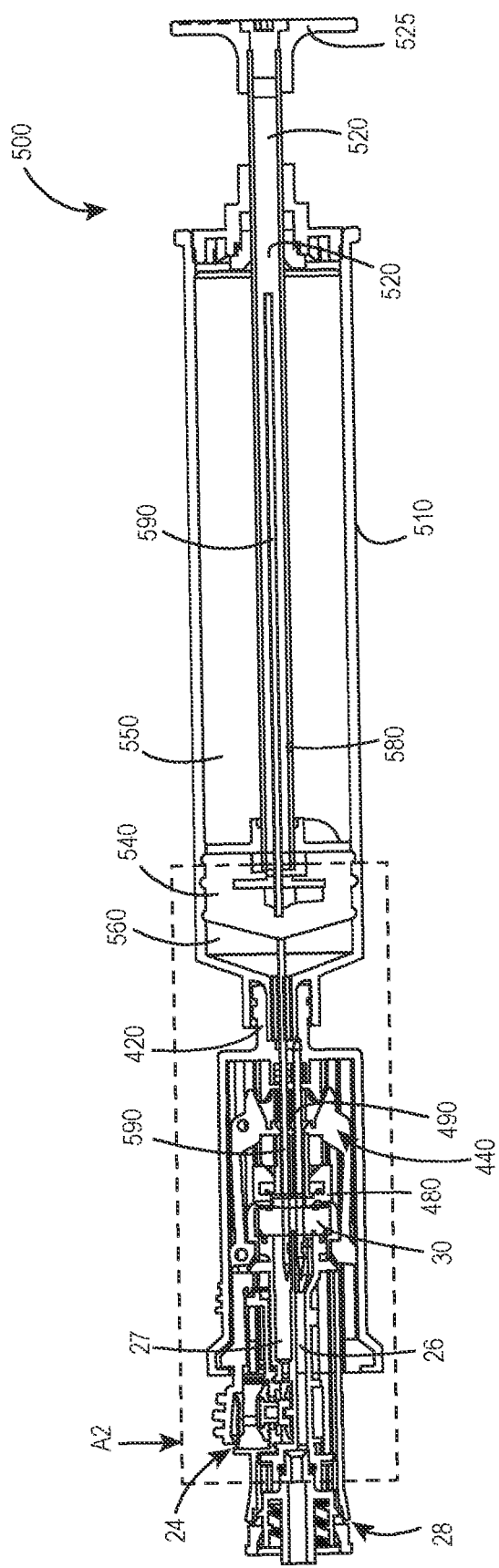
FIG. 2D is a cross-sectional view along line C-C in FIG. 2C.
Figure 2E:
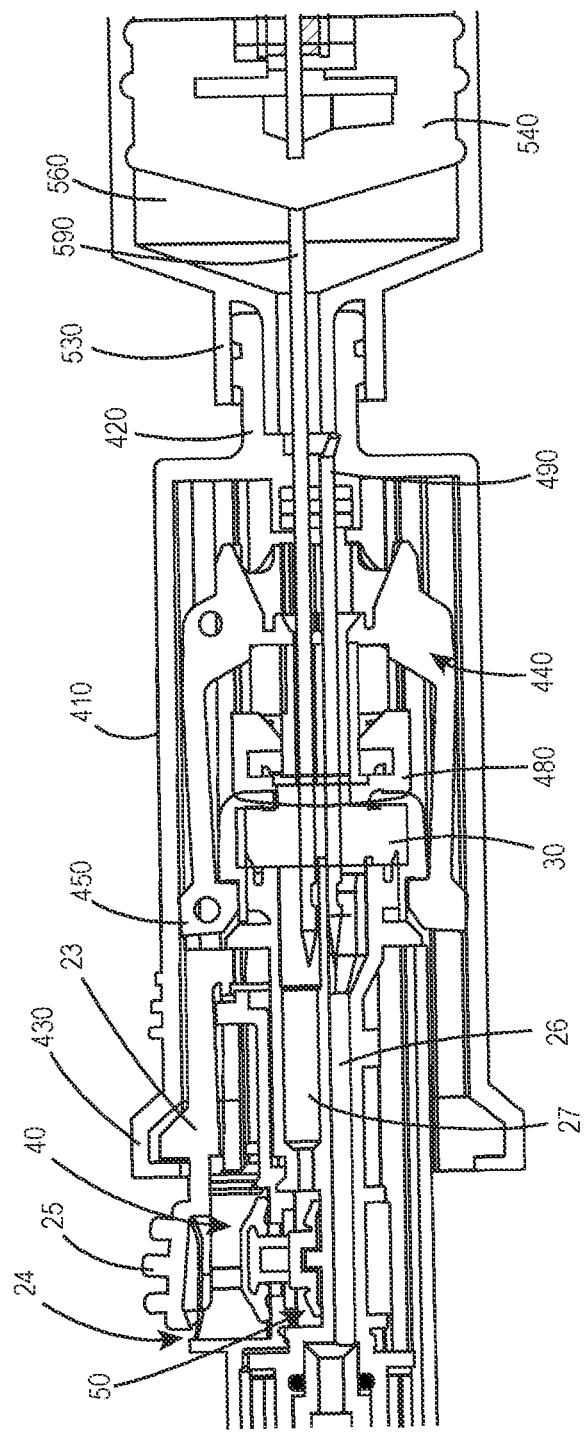
FIG. 2E is an enlarged view of section A2 of FIG. 2D.

When the adaptor 1 is connected to the syringe adaptor 400 having the syringe 500 connected thereto, as shown in FIGS. 2C to 2E, the septum 30 engages with the septum 480 and pushes the septum 480 and the internal locking arrangement 440 towards the syringe 500, thereby causing the air needle 590 and the liquid needle 490 to puncture first the septum 480 and then the septum 30 so that the tips thereof enters into the air channel 27 and the liquid channel 26, respectively. Further, the leaves 450 engage and get locked with the notch 21, and the flange 430 engages and gets locked with the lever notch 23. When the adaptor 1 is to be disconnected from the syringe adaptor 400, the lever button 25 is pressed further into the first outlet 24, thereby releasing the flange 430 from the lever notch 23.

Thus, the adaptor 1 can facilitate connection between the female connector of the syringe adaptor 400 and the female external port 310 of the fluid transfer device 300, thereby facilitating the conversion of a standard female luer lock port of the fluid transfer device 300 into a docking port for safe connection with female connector of the syringe adaptor 400.

When an overpressure is generated in the syringe 500, it is then released into the ambiance through the first valve 40, as described in detail further below with reference to FIG. 6A to 6E. When an underpressure is generated in the syringe 500, it causes the operation of the second valve 50 to allow the air to enter from the ambiance into the air channel 27, as described in detail further below with reference to FIG. 6A to 6E. The syringe adaptor can be separated from the adaptor 1 by pressing the lever button 25 into the first outlet 24 thereby causing the lever notch 23 to disengage from the flange 430.

Reference is now made to FIGS. 3A to 3I and 4A to 4F of the drawings in order to explain in detail the connector 10. FIGS. 3A-3D depict various views of the adaptor 1 with the connector 10 having the luer lock connection port 100 extracted from the outer body 200 along longitudinal axis X of the adaptor 1 for illustration purposes. The luer lock connection port 100 is a male luer lock connection port comprising an elongate central member 110, extending generally parallel to the longitudinal axis X. The elongate central member 110 has a front portion 110A, a middle portion 110B, and a rear portion 110C. The luer lock connection port 100 further comprises a collar 120 surrounding the middle portion 110B of the elongate central member 110. The collar 120 has a sidewall 121 constituting the sidewall of the luer lock connection port 100 and extending generally parallel to the elongate central member 110, and a back wall 122 constituting the back wall of the luer lock connection port 100 extending from and generally perpendicular to the elongate central member 110. The length of the collar 120 in a direction along the longitudinal axis X, i.e., the length of the sidewall 121 of the collar 120, designated as L1 (shown in FIG. 3A), ranges between 5.4 mm to 8 mm. In the illustrated example, the elongate central member 110 and the collar 120 are integrally formed. However, in other examples (not shown), the elongate central member 110 and the collar 120 can be separately manufactured and then assembled together. The sidewall 121 has an internal surface 121A facing the elongate central member 110, and an opposite external surface 121B. The internal surface 121A comprises threads 123 configured to be threaded to the corresponding threads 320 of the fluid transfer device 300 when the fluid transfer device 300 is coupled with the luer lock connection port 100. As can be best seen in FIG. 1C, the threads 123 are in threaded engagement with the threads 320, thereby coupling the fluid transfer device 300 with the luer lock connection port 100, and the external port 310 of the fluid transfer device 300 is received between the elongate central member 110 and the collar 120 such that the collar 120 is positioned between the external port 310 and the outer body 200. The external surface 121B comprises a plurality of protrusions 124 protruding outwardly from the external surface 121B. Each of the protrusions 124 has a first protrusion side surface 124A and a second protrusion side surface 124B defining therebetween a thickness of the protrusion 124 in a direction parallel to circumference of the sidewall 121. The protrusions 124 comprise a connecting member 124C connecting the protrusions 124 with each other along the external surface 121B. In other examples, the external surface 121B can comprise a single protrusion 124.

Figure 3A:
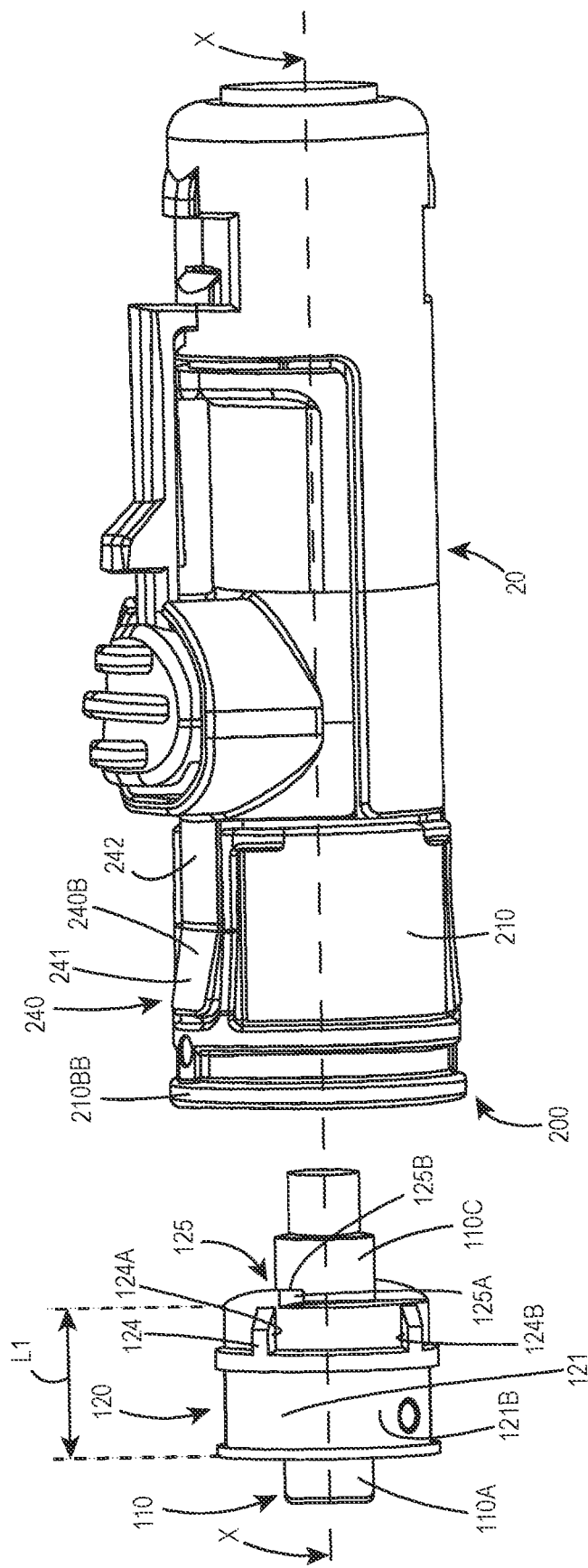
FIG. 3A is a side view of the adaptor of FIG. 1A with its luer lock connection port extracted outside the adaptor for illustration purposes.
Figure 3B:
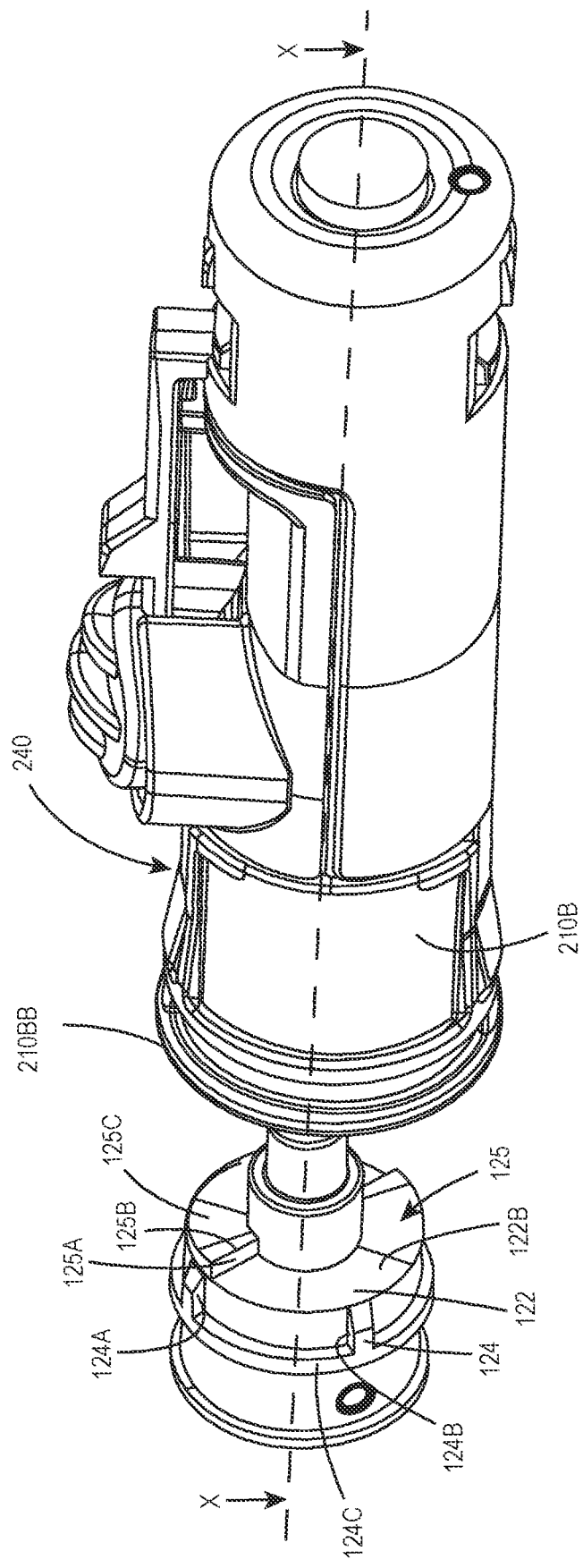
FIG. 3B is a rear perspective view of the adaptor of FIG. 3A.
Figure 3C:
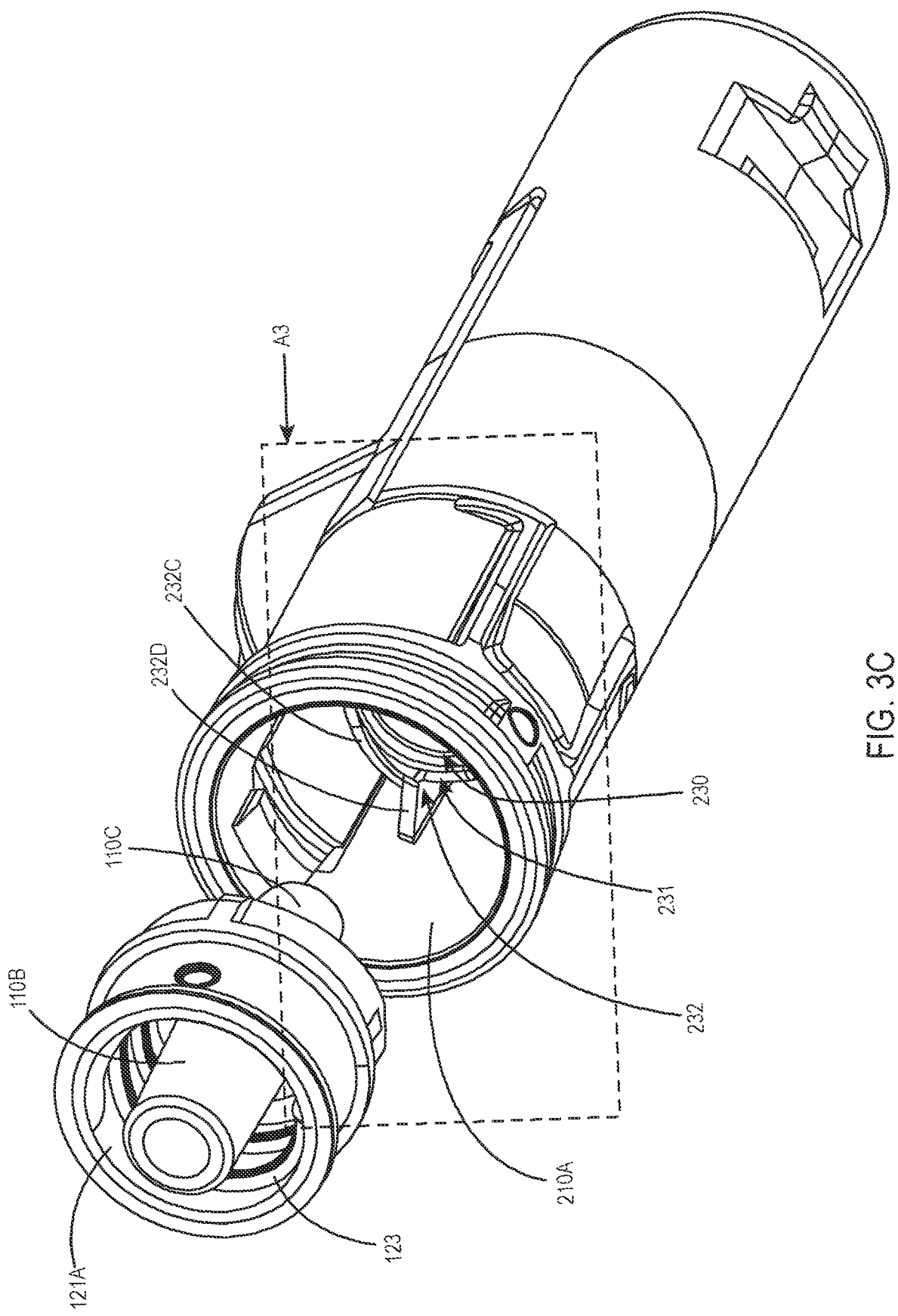
FIG. 3C is a front perspective view of the adaptor of FIG. 3A.
Figure 3D:
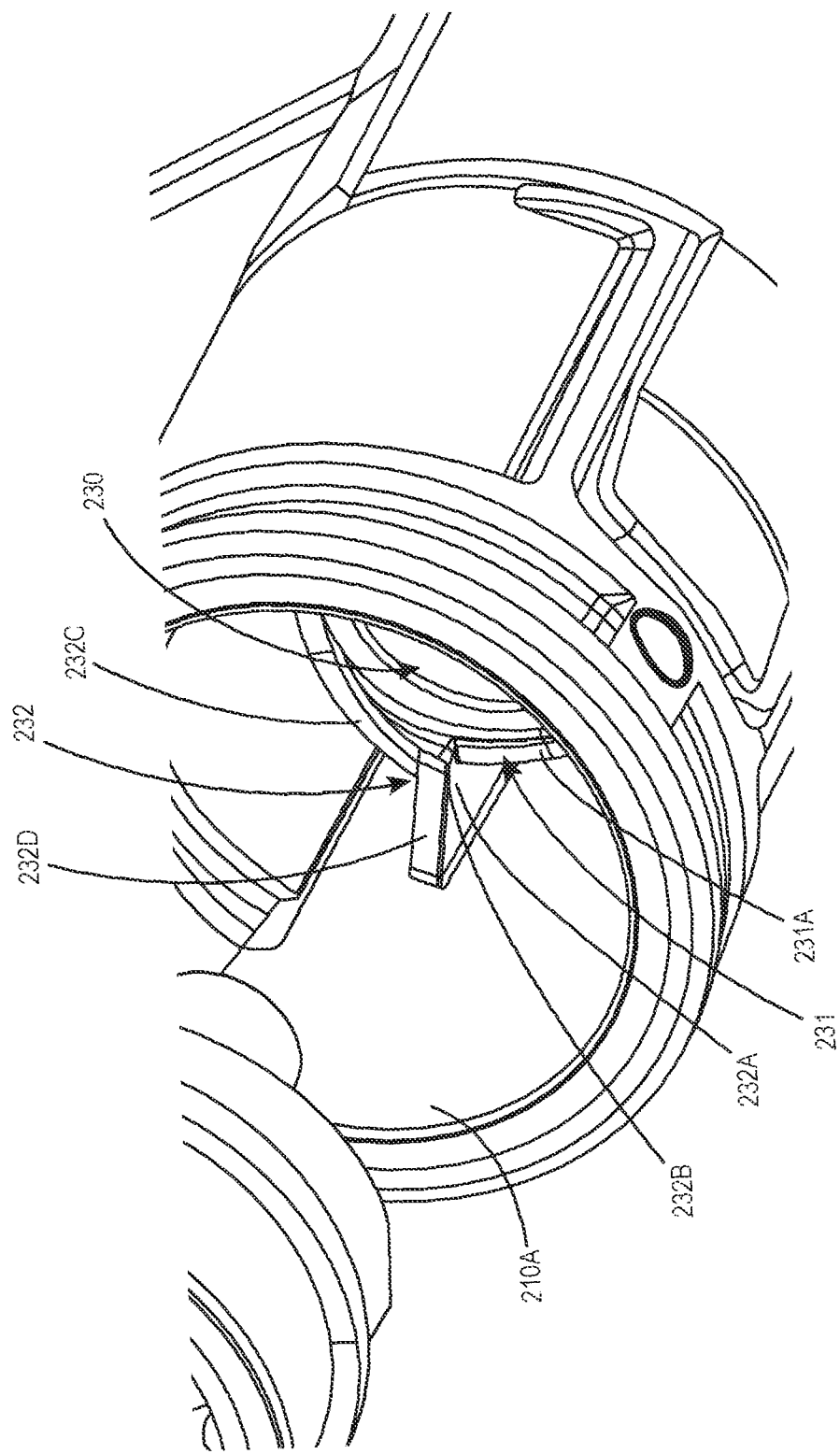
FIG. 3D is an enlarged view of section A3 of FIG. 3C.
Figure 3E:
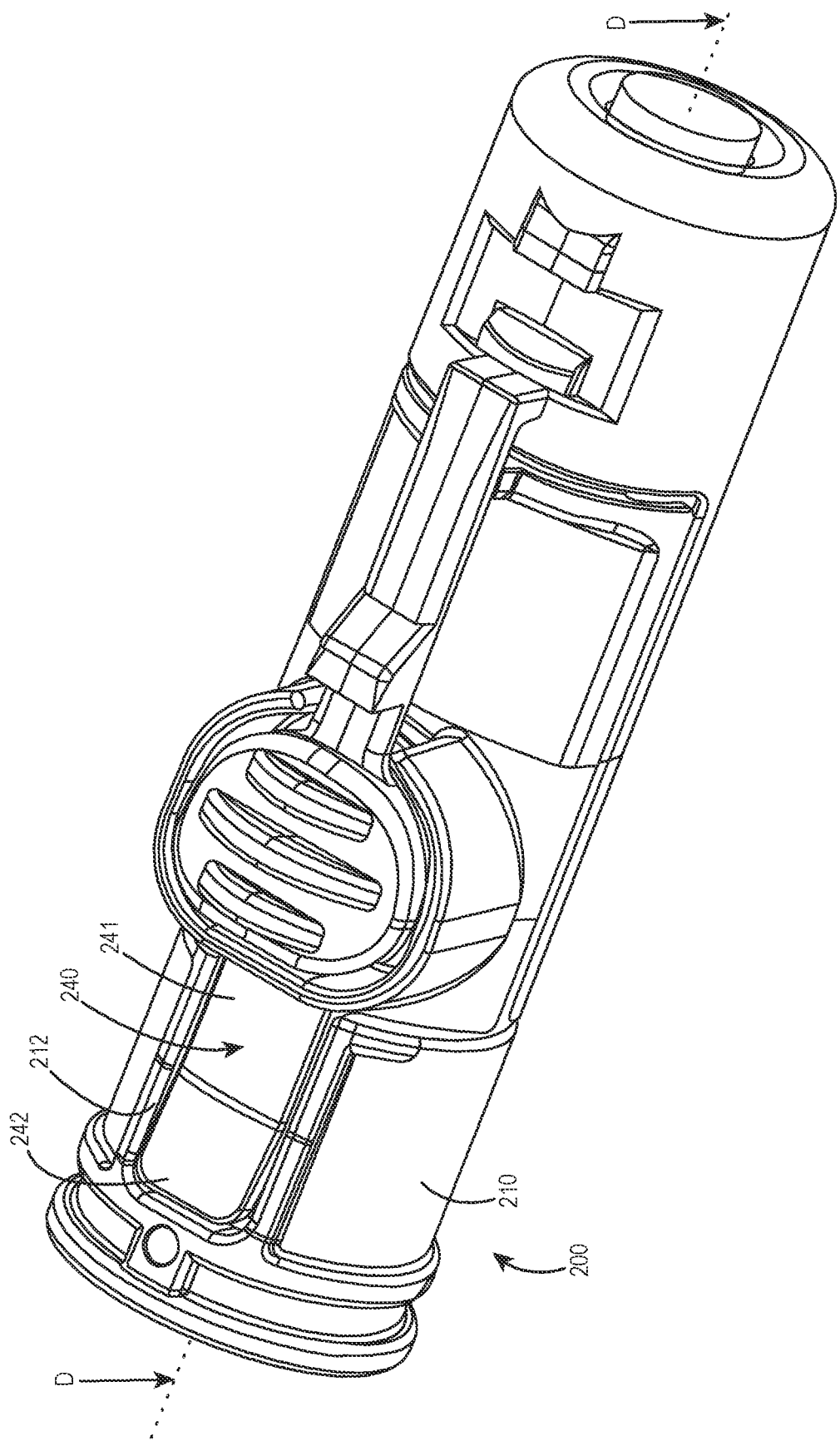
FIG. 3E is a top perspective view of the adaptor of FIG. 1A.
Figure 3F:
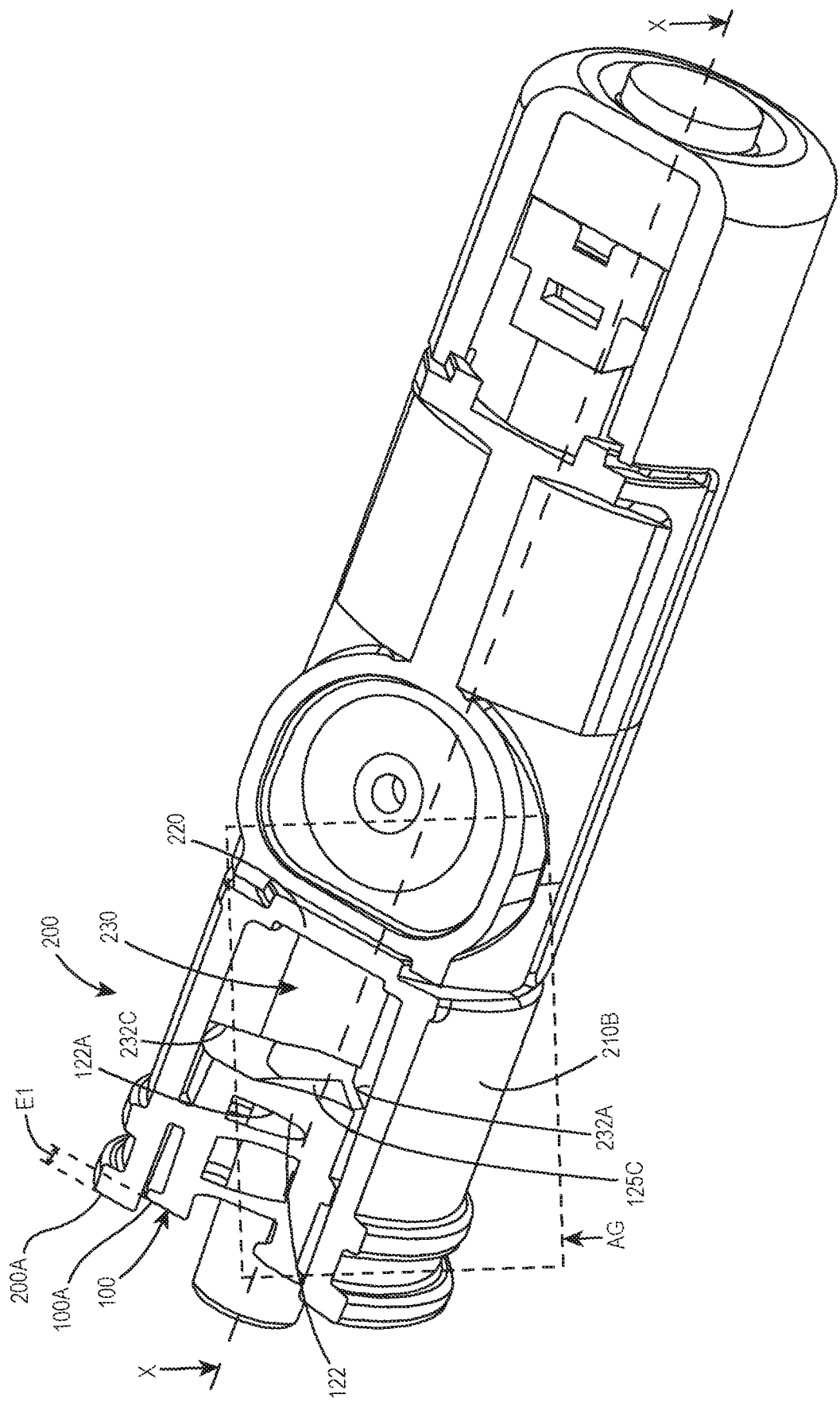
FIG. 3F is a cross-sectional view along line D-D in FIG. 3E, illustrating the adaptor in its coupling disabled state.
Figure 3G:
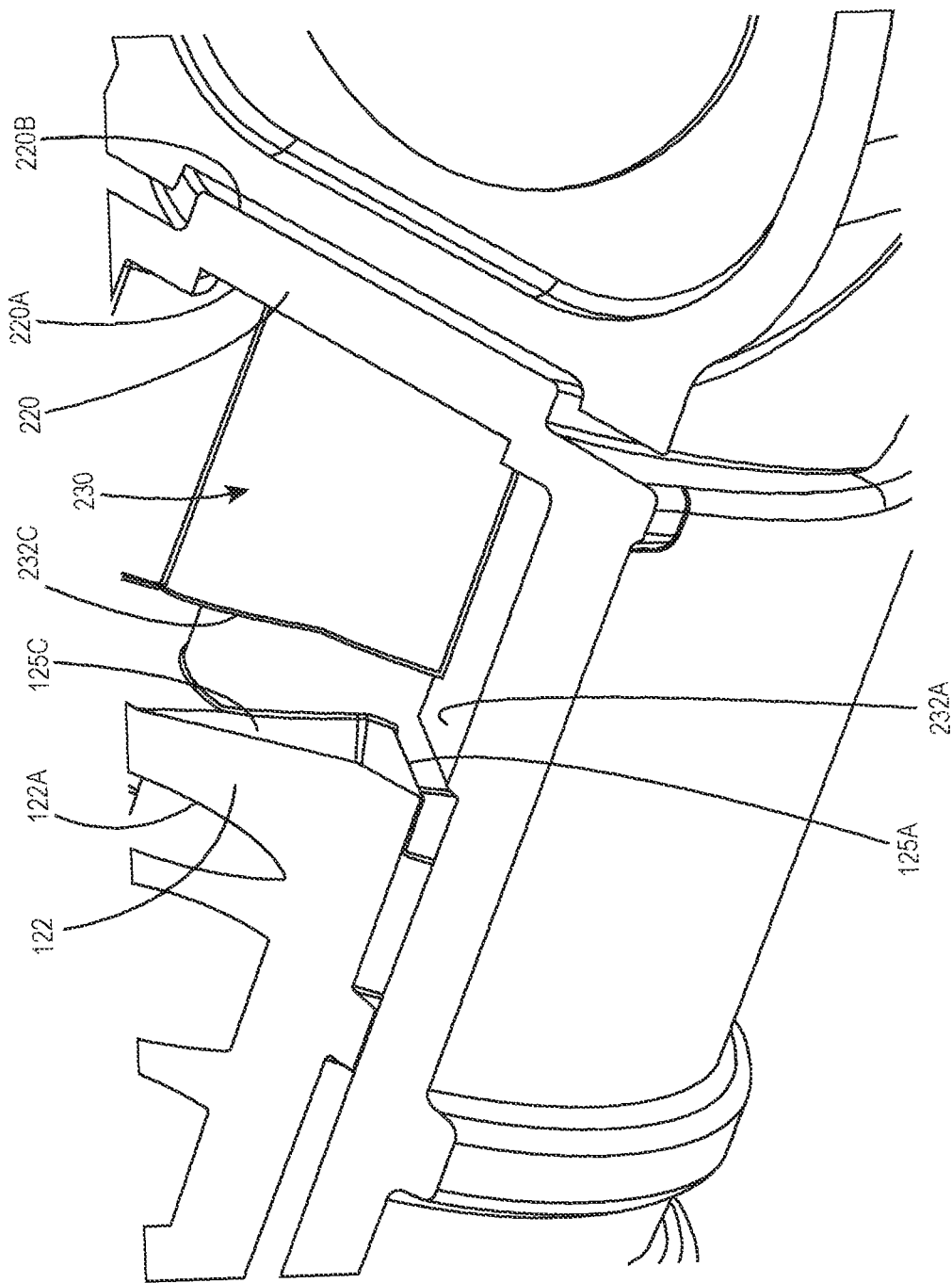
FIG. 3G is an enlarged view of section A4 of FIG. 3F.

The back wall 122 has an internal surface 122A (as best seen in FIGS. 3F and 3G) facing in a direction from which the fluid transfer device 300 is coupled to the connector 10, and an opposite external surface 122B. The external surface 122B comprises a plurality of locking members 125 protruding therefrom. In other examples, the external surface 122B can comprise only one locking member 125. Each of the locking members 125 has a locking surface 125A extending generally perpendicular to the external surface 122B as well as to the elongate central member 110, and having an edge 125B distal to the external surface 122B. In other examples, the locking surface 125A can extend at an angle, other than being perpendicular, with respect to either or both of the external surface 122B and to the elongate central member 110. The locking surface 125A faces towards the clockwise direction of rotation of the luer lock connection port 100. The locking member 125 further comprises a slope 125C extending from the edge 125B to the external surface 122B in the counter-clockwise direction of rotation of the luer lock connection port 100. The slope 125C, in the illustrated example, has a gradient slope, however, in other examples, the slope 125C can be a plain slope.

The outer body 200 comprises a sidewall 210 corresponding to, and extending generally parallel to, the sidewall 121 of the luer lock connection port 100, and a back wall 220 (as best seen in FIG. 3G) corresponding to, and extending generally parallel to, the back wall 122 of the luer lock connection port 100. The back wall 220 has an internal surface 220A (seen in FIG. 3G) facing the luer lock connection port 100 and an opposite external surface 220B. As shown in FIG. 4B, the back wall 220 further comprises a through-hole 221 in fluid communication with the liquid channel 26. The outer body 200 comprises a central member 230 extending from the internal surface 220A in a direction generally parallel to the sidewall 210. The central member 230 receives therewithin the rear portion 110C of the elongate central member 110 of the luer lock connection port 100, such that the elongate central member 110 is in fluid communication with the liquid channel 26 via the through-hole 221. The central member 230 has a rim 231 (seen in FIGS. 3C and 3D) generally facing the back wall 122 of the luer lock connection port 100. As shown in FIG. 3D, the rim 231 comprises a rim surface 231A extending parallel to the external surface 122B of the back wall 122 of the luer lock connection port 100, and has a plurality of arresting members 232 protruding therefrom. In other examples, the rim 231 can comprise only one arresting member 232. Each of the arresting members 232 has an arresting surface 232A extending generally parallel to the locking surface 125A, and having an edge 232B distal to the rim surface 231A. The arresting surface 232A faces towards the counter-clockwise direction of rotation of the luer lock connection port 100. The arresting member 232 further comprises a ramp 232C extending from the edge 232B to the rim surface 231A in the clockwise direction of rotation of the luer lock connection port 100. In the illustrated example, the arresting member 232 is connected to the internal surface 210A of the sidewall 210 of the outer body 200 via a bridge 232D. In other examples, the adaptor 1 may not comprise the bridge 232D.

The ramp 232C, in the illustrated example, has a gradient slope, however, in other examples, the ramp 232C can have a plain slope The locking members 125 and the arresting members 232 constitute a coupling facilitating mechanism according to the illustrated example of the presently disclosed subject matter. The coupling facilitating mechanism is configured to selectively assume a coupling enabled state at which it restricts the rotation of the luer lock connection port 100 at least in the clockwise direction R1, and a coupling disabled state at which it allows the rotation of the luer lock connection port at least in the clockwise direction R1. When the coupling facilitating mechanism is at the coupling disabled state, as shown in FIG. 1A, upon actuation by an operator that applies a pushing force on the luer lock connection port 100, the coupling facilitating mechanism is configured to assume a coupling enabled state.

The sidewall 210 of the outer body 200 has an internal surface 210A facing the central member 230, and an opposite external surface 210B. The sidewall 210 further comprises an opening 211 extending between the internal surface 210A and the external surface 210B. The opening 211 has a rim 212 (seen in FIG. 4B) having an internal surface 212A facing the luer lock connection port 100 and coinciding with the internal surface 210A, and an opposite external surface 212B coinciding with the external surface 210B. The connector 10 further comprises an actuator 240 positioned at least partially in the opening 211. In the illustrated example, the actuator 240 has been shown as being formed with the housing 20. However, in other examples, the actuator 240 can be formed with or connected to the outer body 200, for example at the sidewall 210, the back wall 220, or the rim of the opening 211. The actuator 240 has an internal surface 240A facing and extending parallel to the luer lock connection port 100, and an opposite external surface 240B. The actuator 240 is formed in two portions, a first portion 241 extending from the housing 20, and a second portion 242 extending from the first portion 241. The first portion 241 and the second portion 242 constitute a lever configured to be pivoted in and out of the opening 211 along a connection between either the first portion 241 and the housing 20 or the first portion 241 and the second portion 242. The internal surface 240A comprises a tooth 243 having a first tooth side surface 243A extending from (in the illustrated example, but not necessarily perpendicular to) the luer lock connection port 100 and parallel to the first and the second protrusion side surfaces 124A and 124B of the protrusions 124, and an opposite second side surface (not shown). The actuator 240 and the protrusions 124 constitute a decoupling facilitating mechanism according to the illustrated example of the presently disclosed subject matter. The decoupling facilitating mechanism is configured to selectively assume a decoupling disabled state at which it allows rotation of the luer lock connection port 100 about the longitudinal axis X at least in the counter-clockwise direction R2, and a decoupling enabled state at which it restricts the rotation of the luer lock connection port 100 at least in the counter-clockwise direction R2 so as to allow decoupling of the external port from the luer lock connection port. The decoupling facilitating mechanism is configured to be at the decoupling disabled state, as shown in FIG. 4C, assume, upon actuation by an operator, a decoupling enabled state when the decoupling is to be done, as shown in FIG. 4B. Thus, the decoupling facilitating mechanism needs to be kept in the decoupling enabled state only during the decoupling is under process.

In the illustrated example, the adaptor 1 further comprises an O-ring 250 positioned between the rear portion 110C of the elongate central member 110 and the luer lock connection port 100 and the central member 230 facilitating an efficient fitting of the rear portion 110C of the elongate central member 110 within the central member 230. In other examples, the adaptor 1 may not comprise the O-ring 250.

Figure 3H:
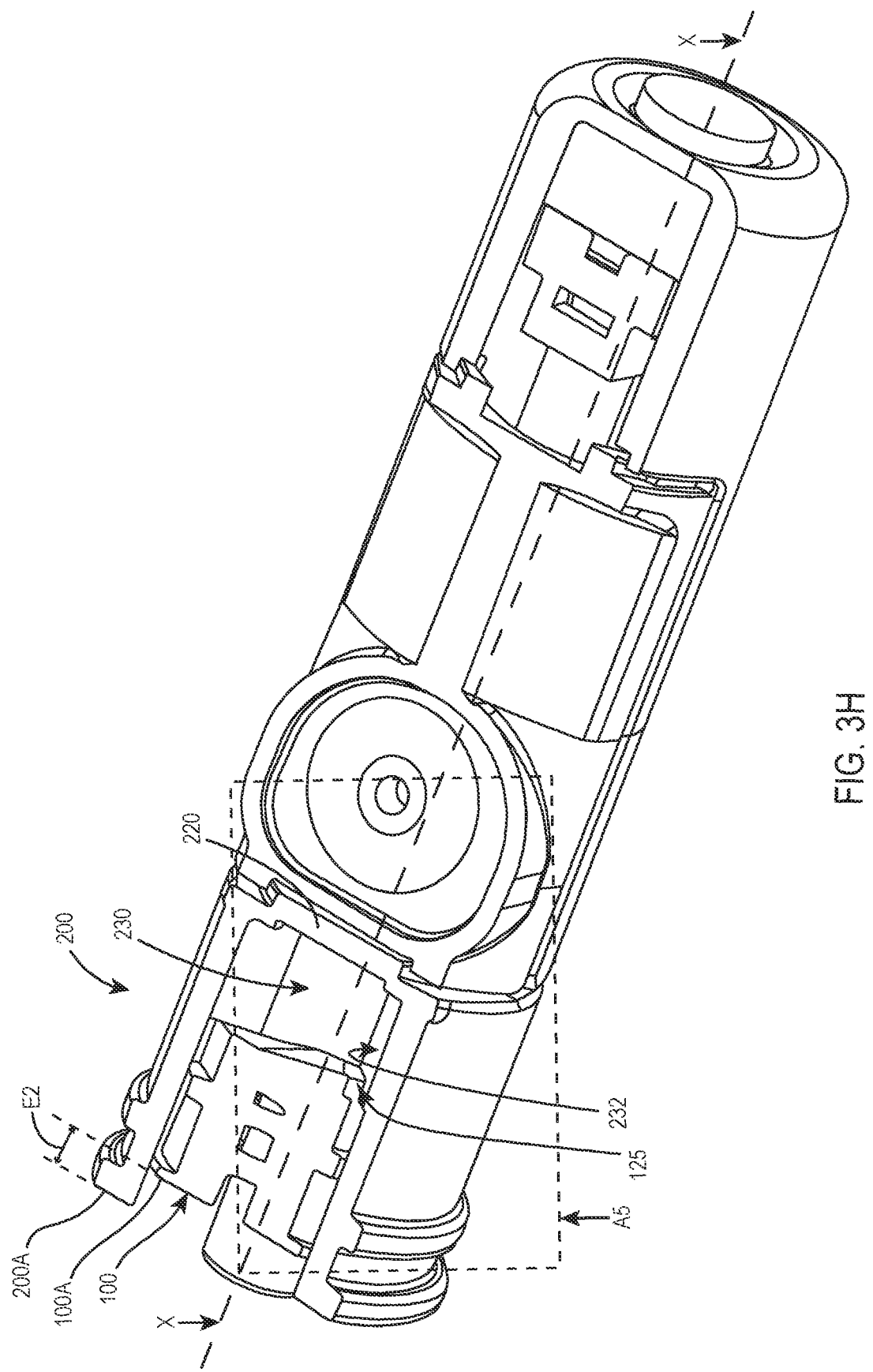
FIG. 3H is a cross-sectional view along line D-D in FIG. 3E illustrating the adaptor in its coupling enabled state.
Figure 31:
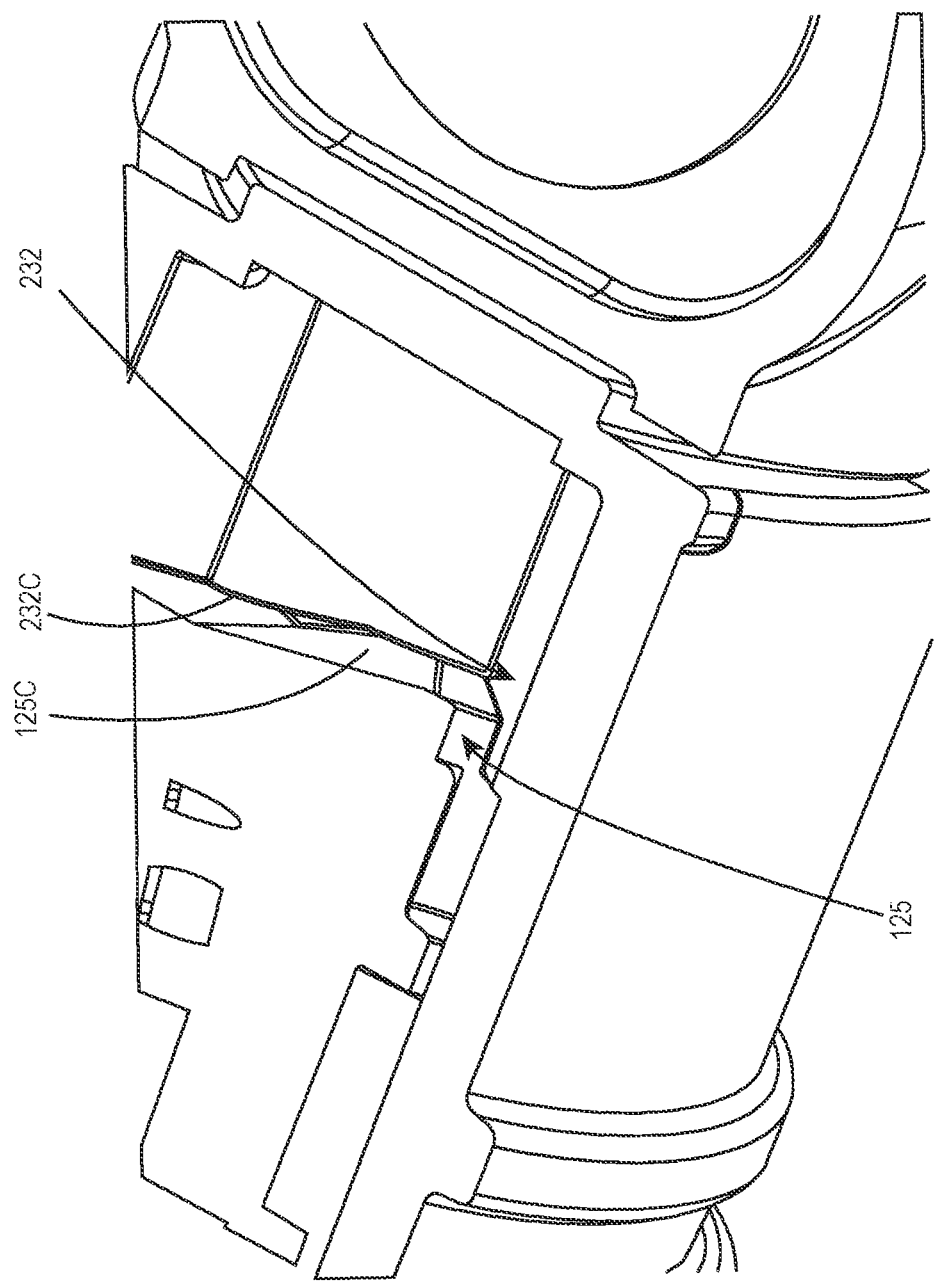

Reference is now made again to FIGS. 3A to 3I in order to explain coupling of the connector 10 to the fluid transfer device 300. As can be best seen in FIGS. 3F and 3G, the luer lock connection port 100 is within the outer body 200 such that the locking member 125 does not engage with the arresting member 232 and the coupling facilitating mechanism is in its coupling disabled state. At this state, the luer lock connection port 100 is at its first (normal) position along the longitudinal axis X, within the outer body 200, and can freely rotate about the longitudinal axis in both the clockwise as well as counterclockwise direction. At the first normal position of the luer lock connection port 100, a proximal end 100A is a first extent E1 within the outer body 200 from a proximal end 200A of the outer body 200, as can be best seen in FIG. 3F. As the luer lock connection port 100 can rotate freely at this position, no external element can thus be threaded to the threads 123 of the luer lock connection port 100 unless the rotation of the luer lock connection port 100 is restricted at least in the direction of the threading, which in the illustrated example is clockwise. When the fluid transfer device 300 is to be coupled to the connector 10, the coupling facilitating mechanism needs to be displaced into its coupling enabled state. The luer lock connection port 100 is pushed further inside the outer body 200 along the longitudinal axis X, as can be best seen in FIGS. 3H and 3I, for example by force applied by the fluid transfer device 300, when an operator pushes the same for coupling it with the connector 10, along the longitudinal axis X during coupling. As shown in FIGS. 3H and 3I, the luer lock connection port 100 is in its second pushed position along the longitudinal axis X, within the outer body 200, and the locking member 125 engages with the arresting member 232 such that the rotation of the luer lock connection port is restricted in the clockwise direction, and thus the coupling facilitating mechanism is in its coupling enabled state, thereby enabling the coupling of the connector 10 with the fluid transfer device 300, for example. At the second pushed position of the luer lock connection port 100, the proximal end 100A is a second extent E2, greater than the first extent E1, within the outer body 200 from a proximal end 200A of the outer body 200, as can be best seen in FIG. 3H. At this state, as the luer lock connection port 100 cannot rotate in the clockwise direction, thus threads of an external port, for example that of the fluid transfer device 300, can be threaded onto the threads 123 of the luer lock connection port thereby coupling the same with the connector 10. As can be seen in FIG. 3I, at the coupling enabled state, the locking surface 125A engages with the arresting surface 232A thereby restricting the rotation of the luer lock connection port 100 in the clockwise direction. The slope 125C engages with the ramp 232C, and the inclination of the slope 125C and the ramp 232C allows the rotation of the luer lock connection port 100 in the counter-clockwise direction. In other examples, the coupling facilitating mechanism can have any other structure capable of achieving the similar purpose of restricting the rotation of the luer lock connection port 100 with respect to the outer body 200 at least in the direction of threading.

Reference is now made again to FIGS. 1C and 4A to 4F in order to explain decoupling of the connector 10 from the fluid transfer device 300. As can be seen in FIGS. 1C and 4C the fluid transfer device 300 is coupled to the connector 10 and the actuator 240 is not pressed, and thus the decoupling facilitating mechanism is in its decoupling disabled state. At the decoupling disabled state of the decoupling facilitating mechanism, the luer lock connection port 100 can rotate freely at least in the direction of unthreading, which in the illustrated example is counter-clockwise. When the fluid transfer device 300, while it is coupled to the connector 10, is rotated in the counter-clockwise direction, the luer lock connection port 100 rotate therewith thereby preventing the decoupling of the fluid transfer device 300 from the connector 10. For decoupling to take place, the rotation of the luer lock connection port 100 needs to be restricted in the counter-clockwise direction. However, as can be seen in FIGS. 1A to 1C and 4A to 4F, there is no enough space in the opening 211 around the actuator 240 for an average (or even smaller than the average) sized fingertip of an operator (or even a child) to be inserted, thus, the outer body 200 prevents an operator from directly accessing by fingertips the luer lock connection port 100, thus, the operator needs to indirectly access the luer lock connection port 100 facilitated by the actuator 240 in conjunction with the opening 211. Thus, when the fluid transfer device 300 is to be decoupled from the connector 10, the actuator 240 is pressed into the opening 211. As can be best seen in FIGS. 4A and 4D to 4F, when the actuator 240 is pressed (by the operator) with a pressing force, the tooth 243 engages with the protrusion 124 thereby shifting the decoupling facilitating mechanism into its decoupling enabled state. As shown in FIG. 4F, the first tooth side surface 243A of the tooth 243 engages with the second tooth side surface 124B of the protrusion 124, thereby restricting the rotation of the luer lock connection port 100 in the counter-clockwise direction. As is clear from FIG. 4F, for the first tooth side surface 243A of the tooth 243 engages with the second side surface 124B of the protrusion 124, the actuator 240 has to be, can only be, pressed when no portion of the tooth 243 is not directly above the protrusion 124. In other words, for the decoupling to be performed, the luer lock connection port 100 needs to be rotated so as the tooth 243 and the protrusion 124 are not radially aligned, and then the actuator 240 can be pressed. In fact, if the tooth 243 would be directly above the protrusion 124, the protrusion would prevent the actuator from being pressed effectively thereby not allowing the decoupling facilitating mechanism to effectively restrict the rotation of the luer lock connection port 100. In the examples where there are more than one protrusions (one example shown in FIG. 3B), the tooth has to be aligned between two such protrusions and then the actuator be pressed to displace the decoupling facilitating mechanism into its decoupling enabled state. At this state of the decoupling facilitating mechanism, when the fluid transfer device 300 is rotated counter-clockwise, the luer lock connection port 100 does not rotate therewith, thereby enabling decoupling of the fluid transfer device 300 from the connector 10 by rotation of the fluid transfer device 300 in the counter-clockwise direction by the operator. The actuator 240 returns to its original not-pressed state upon removal of the pressing force by the operator. In other examples, the decoupling facilitating mechanism can have any other structure capable of achieving the similar purpose of restricting the rotation of the luer lock connection port 100 with respect to the outer body 200 at least in the direction of unthreading.

Figure 4A:
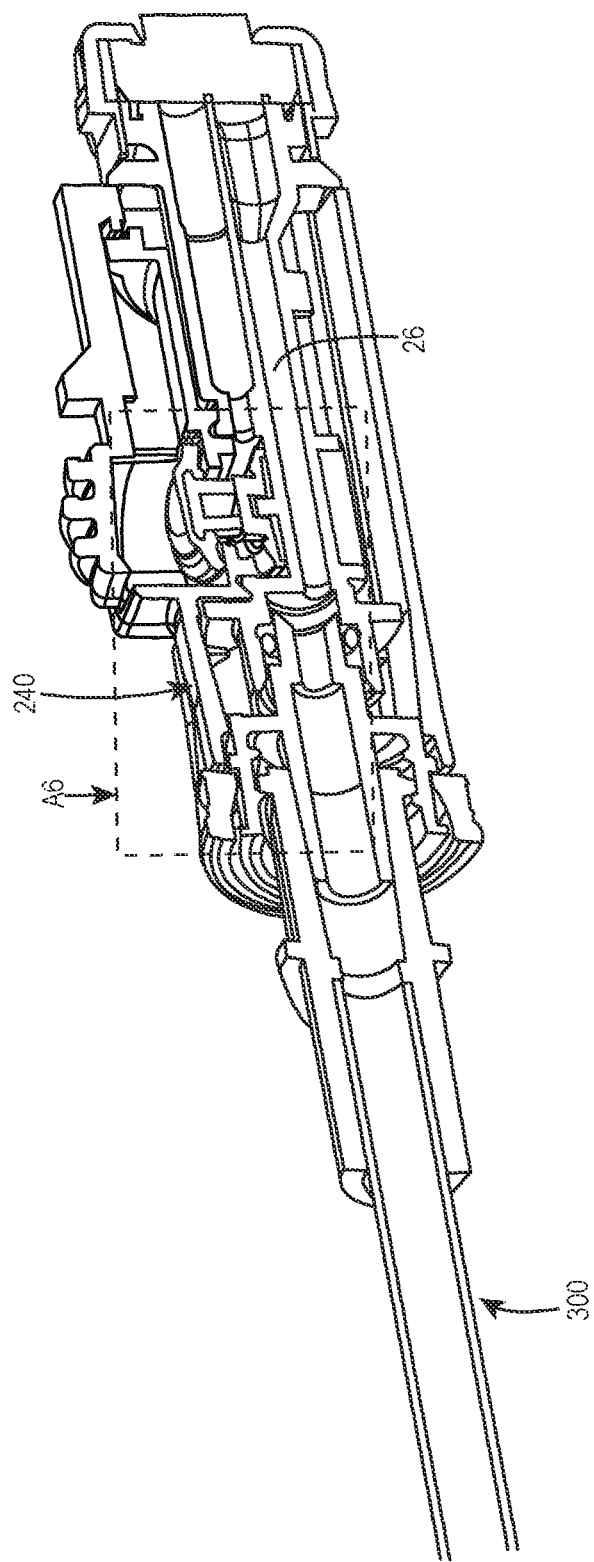
FIG. 4A is the same view as FIG. 1C illustrating the adaptor in its decoupling enabled state.
Figure 4B:
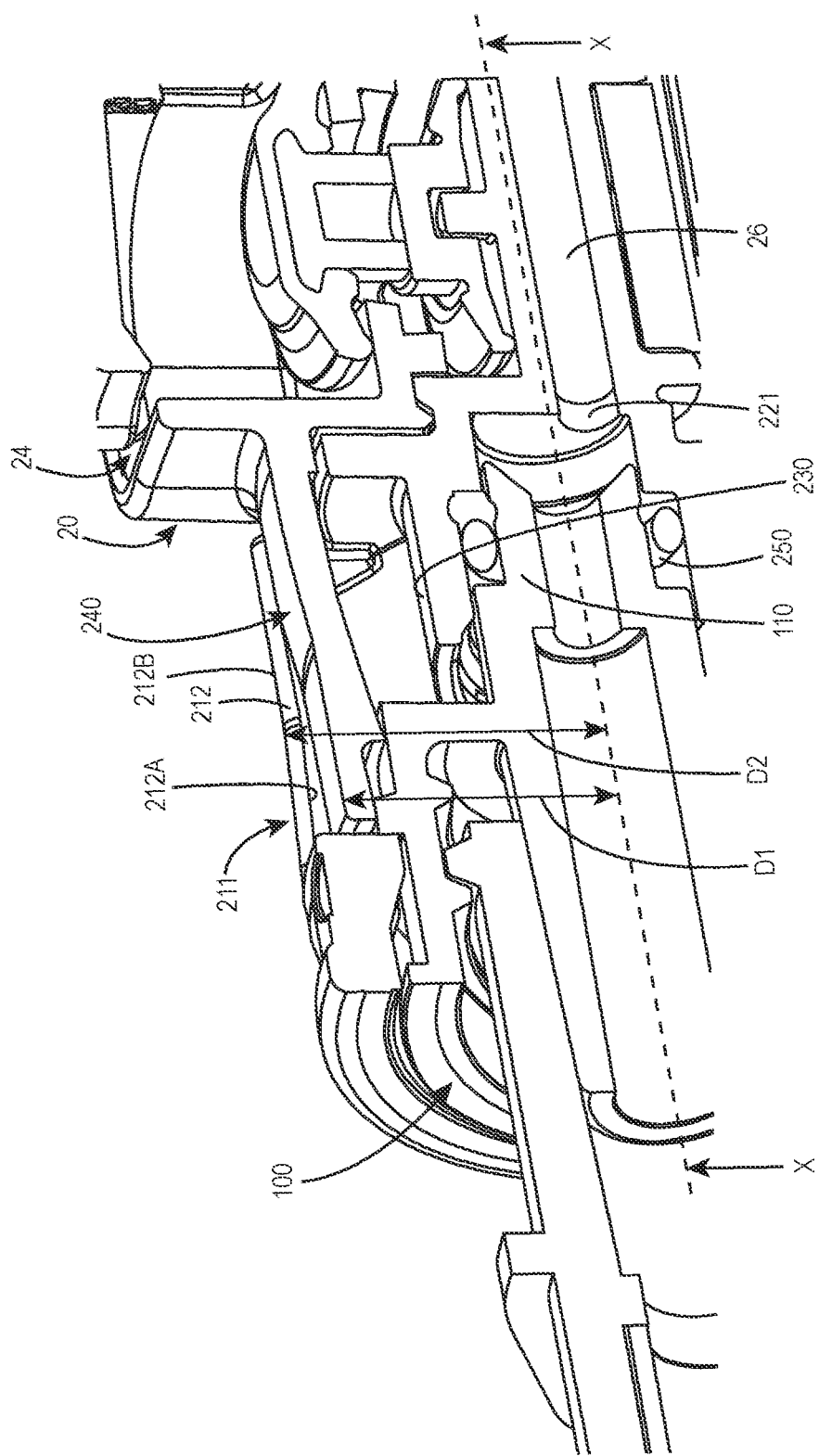
FIG. 4B is an enlarged view of section A6 of FIG. 4A.
Figure 4C:
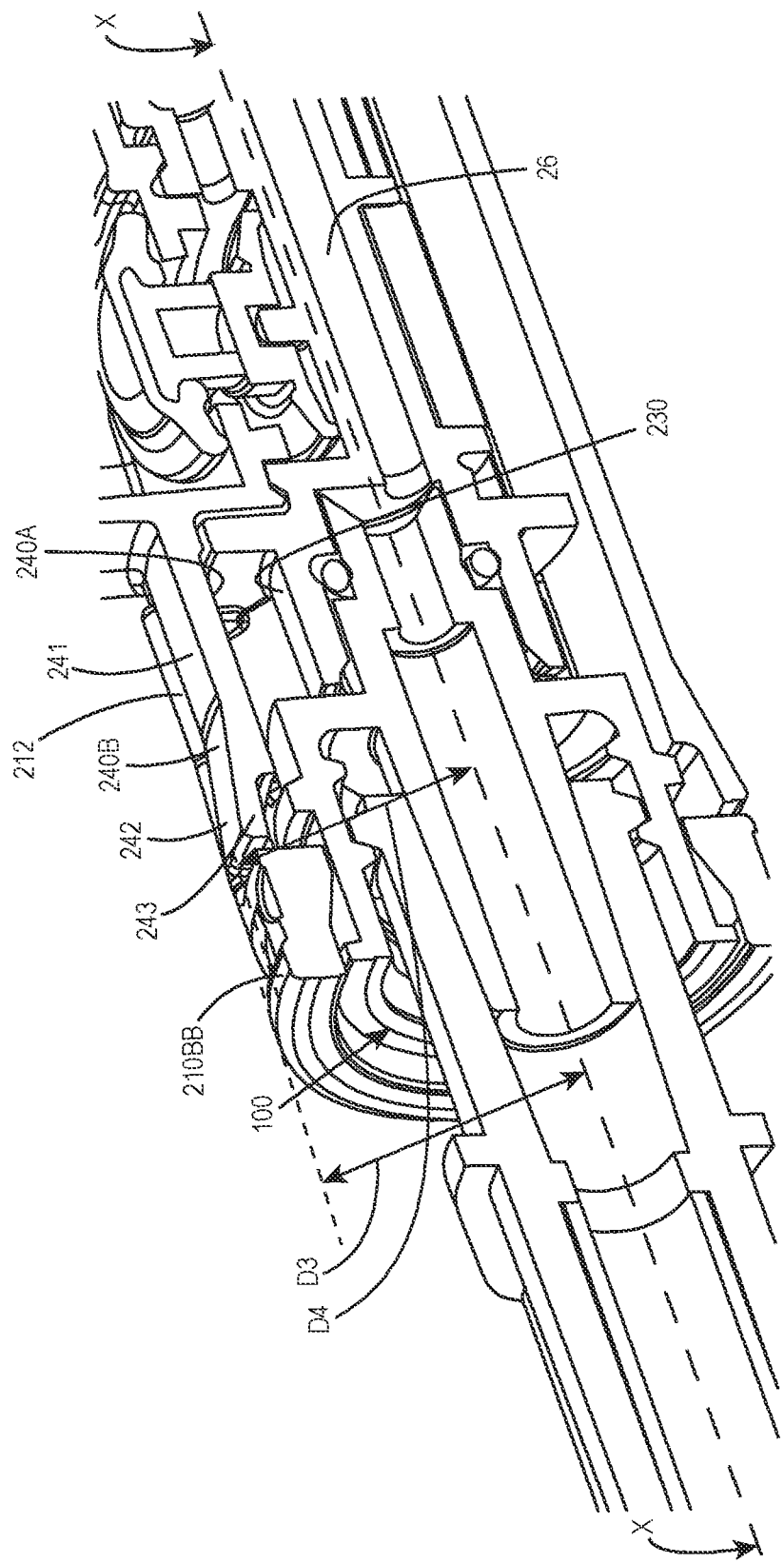
FIG. 4C is an enlarged view of section A1 of FIG. 1C.
Figure 4D:
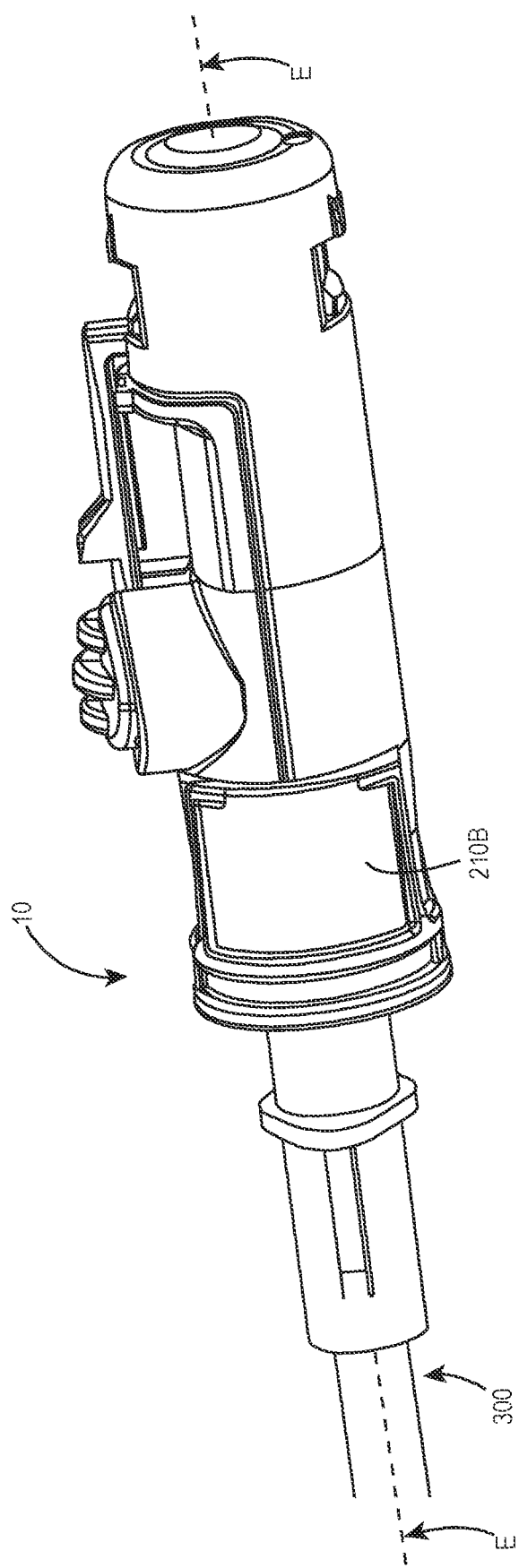
FIG. 4D is a rear perspective view of the adaptor and the external device of FIG. 1B, illustrating the adaptor in its decoupling enabled state.
Figure 4E:
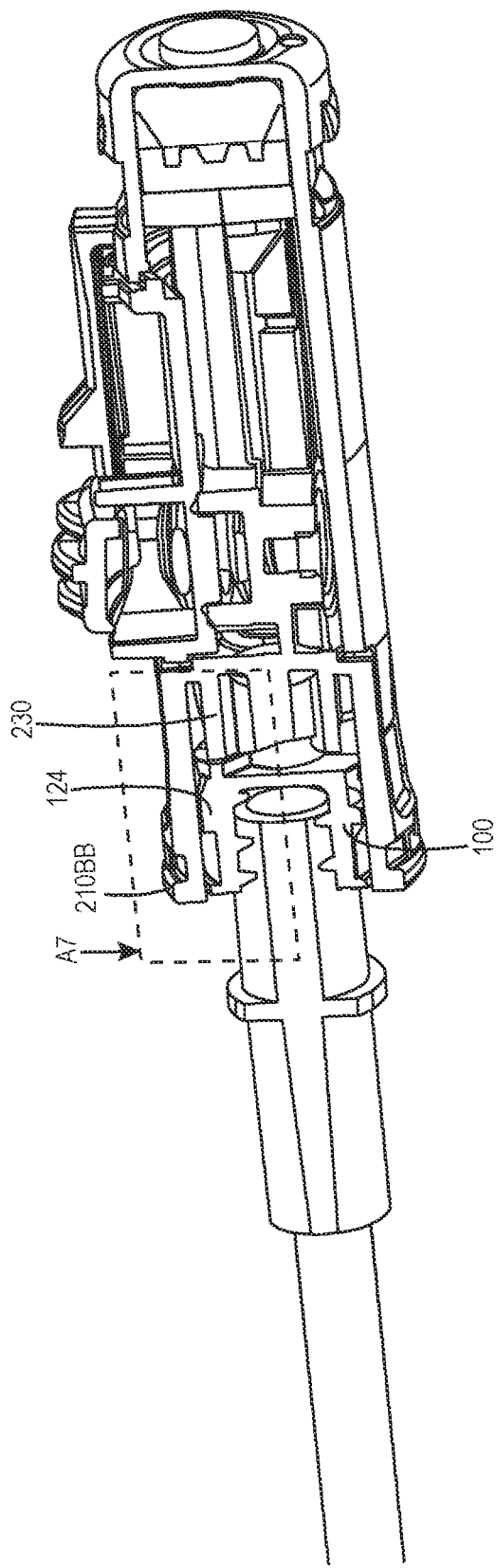
FIG. 4E is a cross-sectional view along line E-E in FIG. 4D.
Figure 4F:
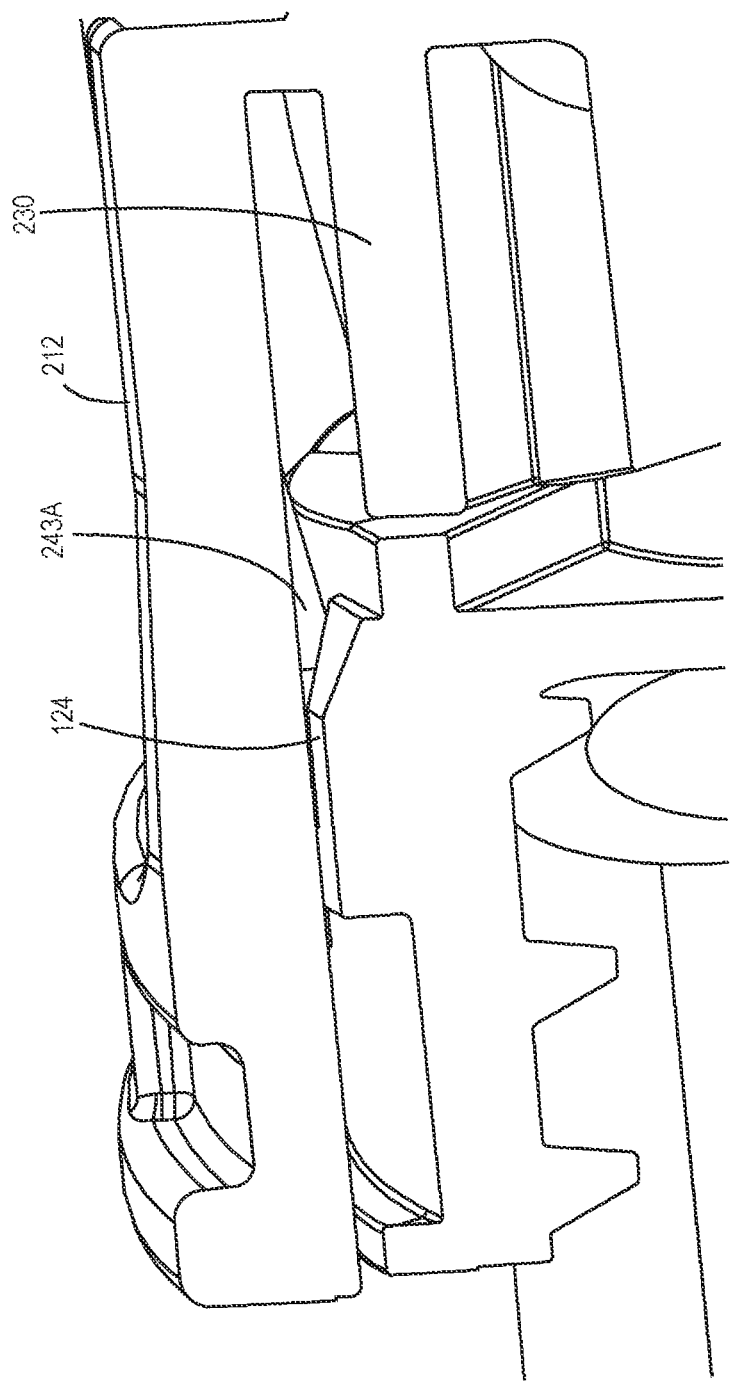
FIG. 4F is an enlarged view of section A7 of FIG. 4E.

As can be seen in FIGS. 4A and 4B, at the decoupling enabled state, the actuator 240 is sunk into the opening 211 such that a minimal distance D1 between the external surface 240B of the actuator 240 and the longitudinal axis X is less than a minimum distance D2 between the external surface 212B of the rim 212 of the opening 211 and the longitudinal axis X. In other words, at the decoupling enabled state, the external surface 240B of the actuator 240 lies below an imaginary plane extending over the opening 211, and defined by, and/or comprising, the external surface 212B of the rim 212.

As can be seen in FIG. 4C, at the decoupling disabled state, i.e., when the actuator 240 is not pressed, the external surface 240B, or at least a majority thereof, of the actuator 240 lies below an imaginary plane parallel to the outer body 200 and comprising a portion of the external surface 210B farthest from the longitudinal axis, for example, the portion 210BB as shown in FIG. 4C. In other words, a maximum distance D3 between the external surface 210B and the longitudinal axis X is greater than a maximum distance D4 between the external surface 240B and the longitudinal axis X. Such a configuration of the actuator with the outer body 200 renders the actuator as a hidden button, inasmuch as an operator would not even presume the actuator 240 to be an element equipped to facilitate the decoupling of the fluid transfer device 300 from the connector 10.

It is to be understood herein that though drawings illustrate two openings 211 and two corresponding actuators 240, only one opening 211 and one actuator 240 have been described herein for the ease of understanding, and the other ones operate in the same manner as to the ones described herein. In fact, both the actuators 240 can be used together, from opposite sides of the connector 10, to improve the efficiency of the decoupling facilitating mechanism by more effectively restricting the rotation of the luer lock connection port 100.

Further, as can be in FIGS. 1A to 1C, 2A to 2E, 3A to 3I, and 4A to 4F, the outer body 200 radially covers the majority of the luer lock connection port 100, or at least the sidewall 121 thereof. An operator can not access, without the use of the decoupling facilitating mechanism, or directly by fingertips, the luer lock connection port 100 so as to restrict its rotation in any direction to facilitate coupling or decoupling of the connector 10 to or from the fluid transfer device 300. In other examples, the outer body 200 can have a plurality of openings or through holes on the sidewall 210 thereof, to radially cover at least 90 percent, or at least 80 percent, or at least 70 percent, or at least 60 percent, or at least 50 percent of the luer lock connection port 100, or at least the sidewall 121 thereof. However, each one of such openings would have at least one dimension smaller than an average diameter of a fingertip of a child. For instance, the average diameter of the fingertips of a child of about 3-10 years of age is approximately 10-12 mm. Thus, in some examples, every opening would have at least one dimension smaller than 10 mm. Such a configuration of the outer body 200 with the luer lock connection port 100 renders the connector 10 to be a tamper proof connection, i.e., direct access to the luer lock connection port 100 through the outer body 200 by fingertips is prevented, at least after the connector 10 has been coupled to the fluid transfer device 300.

Figure 5A:
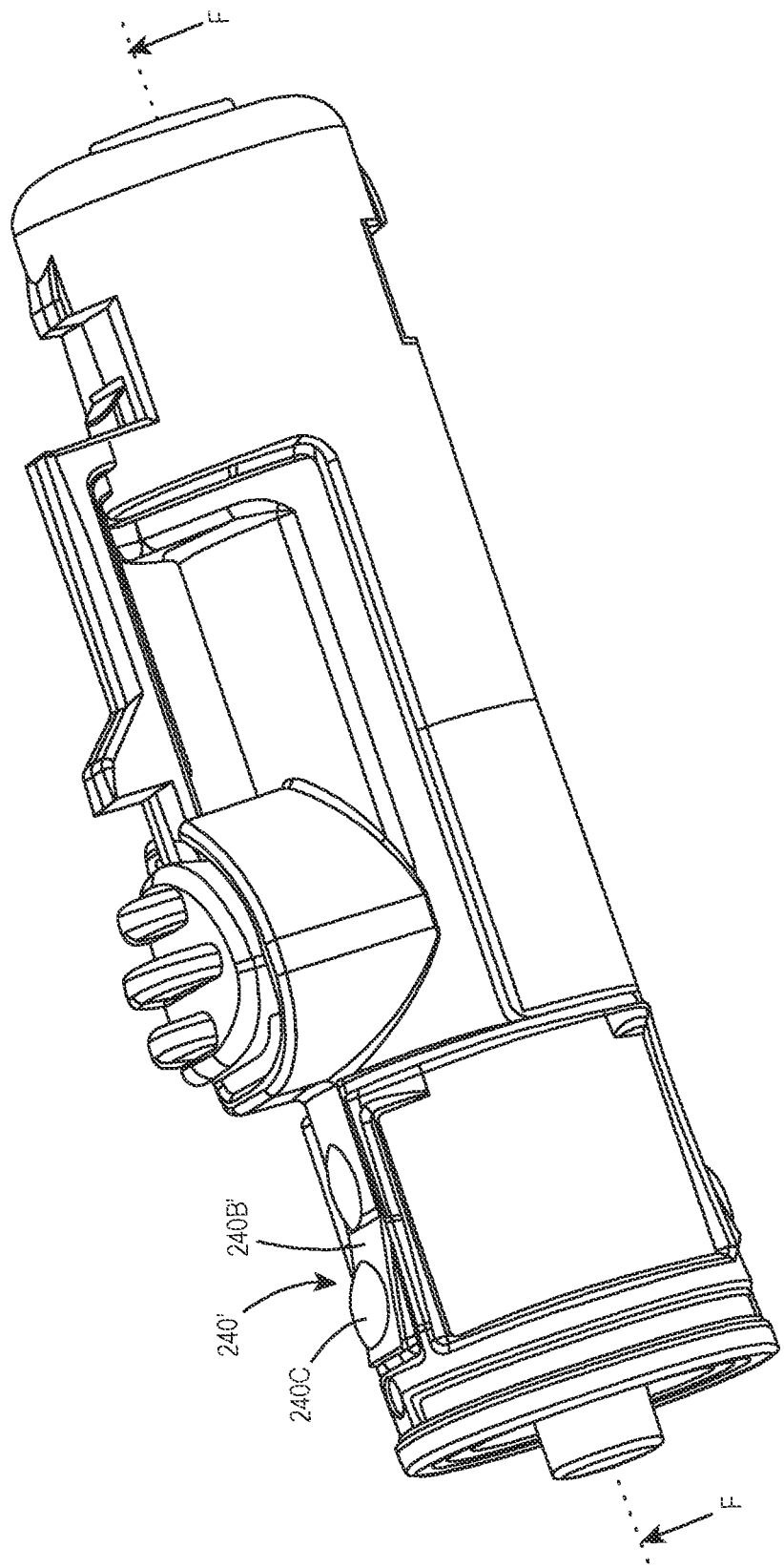
FIG. 5A is a side perspective view of an adaptor according to a second example of the presently disclosed subject matter, in its decoupling disabled state.
Figure 5B:
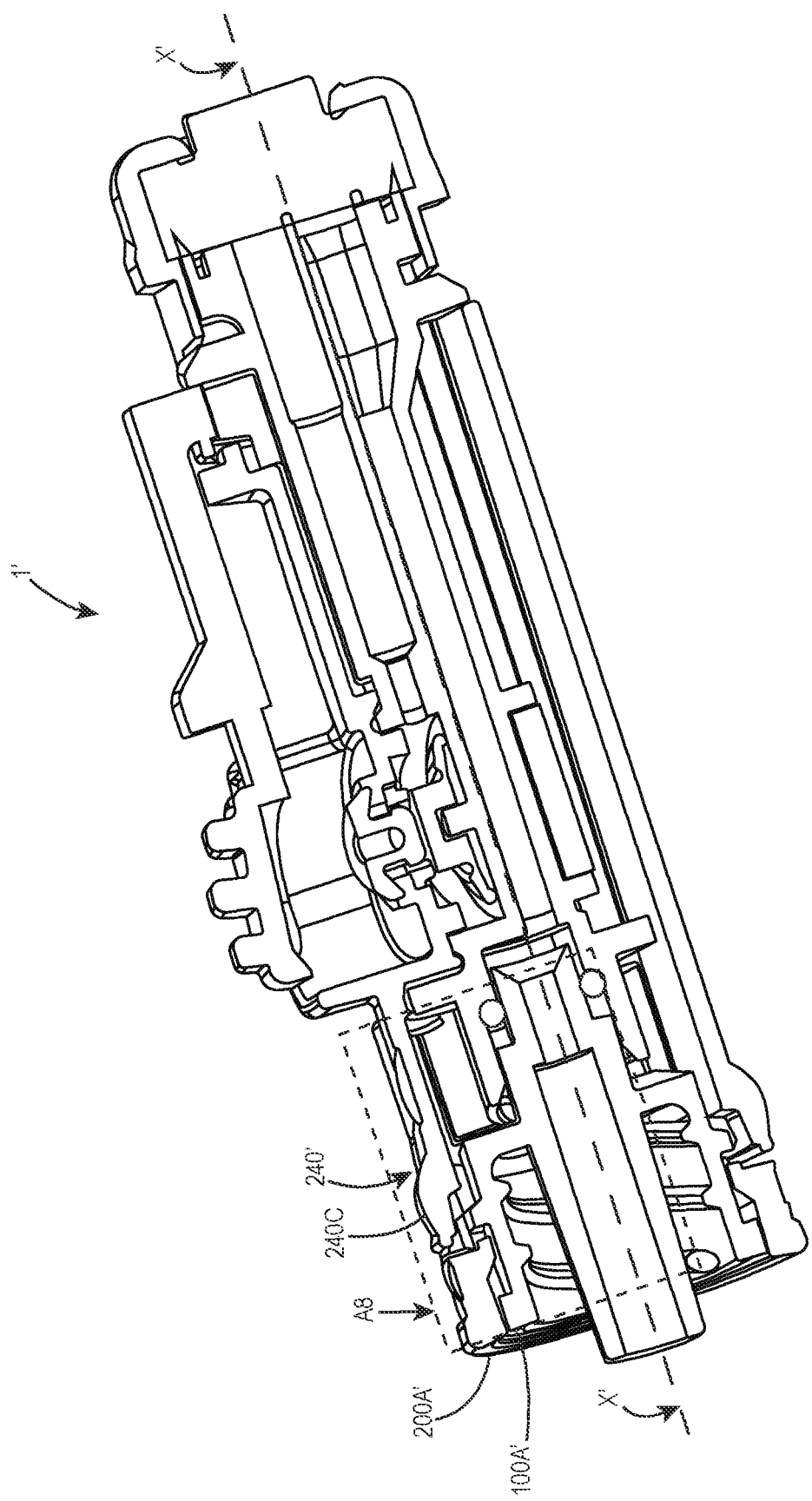
FIG. 5B is a cross-sectional view along line F-F in FIG. 5A, illustrating the adaptor with its luer lock connection port in its normal position.
Figure 5C:
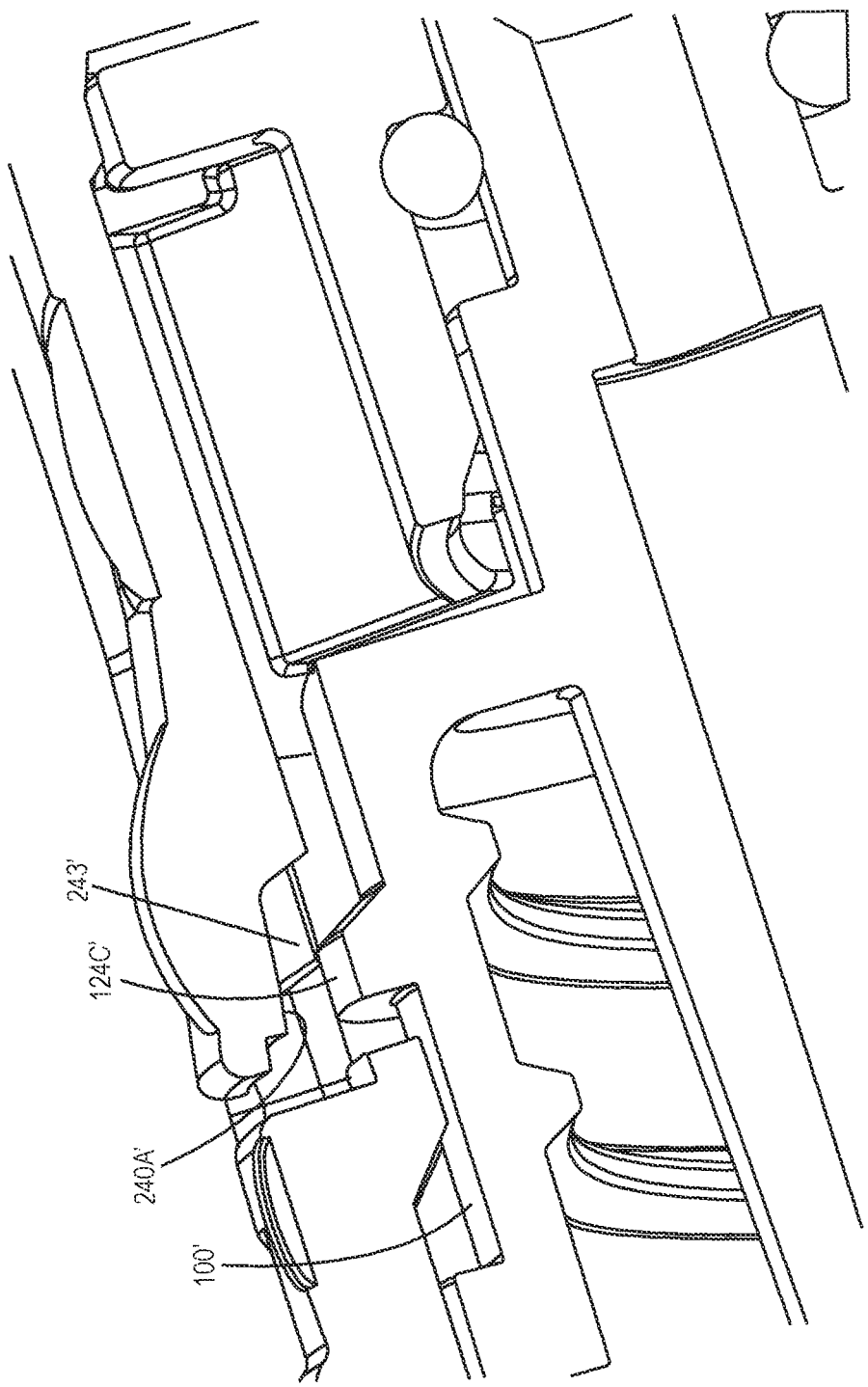
FIG. 5C is an enlarged view of section A8 of FIG. 5B.
Figure 5D:
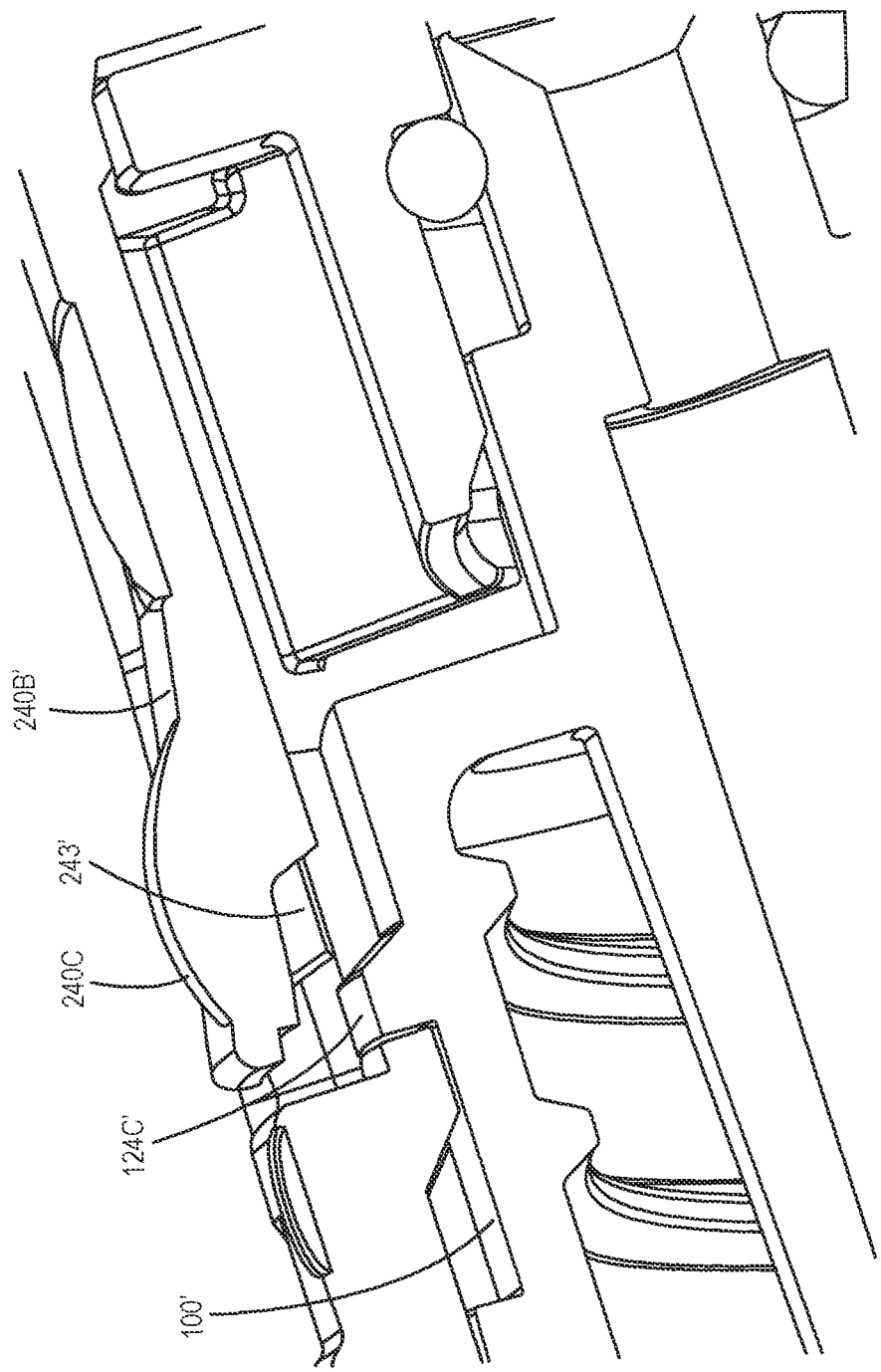
FIG. 5D is the same view as FIG. 5C, illustrating the adaptor with its luer lock connection port in its first position.

Attention is now directed to FIGS. 5A-5D of the drawings illustrating an adaptor 1' according to another example of the presently disclosed subject matter. The adaptor 1' has at least some of the elements corresponding to those of the adaptor 1 as described above, and have been depicted by corresponding reference numerals for ease of understanding. Additionally, the adaptor 1' comprises a bump 240C formed on the external surface 240B' of the actuator 240'. The bump 240C gives the actuator 240' a look and feel of an actual button, unlike the hidden button as that of actuator 240 as described above. In some examples (not shown), instead of the bump, there can be any other shape, structure or the like for the actuator to have a desired look and feel. Further, as shown in FIG. 5C, the tooth 243' is so formed and positioned on the internal surface 240A' of the actuator 240' that when the luer lock connection port 100' is in its second position along the longitudinal axis X' (which for example could have been attained during coupling and been left in that position thereafter), the tooth 243' is vertically aligned above the connecting member 124C'. At this position of the luer lock connection port 100', the connecting member 124C' prevents the actuator 240' from being pressed and thereby preventing the decoupling facilitating mechanism to attain its decoupling enabled state. In order to displace the decoupling facilitating mechanism to attain its decoupling enabled state, i.e., to press the actuator 240', it is necessary to pull the luer lock connection port 100' into a third position position along the longitudinal axis X', as shown in FIG. 5D (which in the illustrated example is the first position). In some examples, the third position can be any position between the first position and the second position. In some examples, the third position can be such as the first position may lie between the third and the second positions. In this position of the luer lock connection port 100', the connecting member 124C' displaces from under the tooth 243' and thus, the actuator 240' can be pressed for the decoupling facilitating mechanism to attain its decoupling enabled state. The luer lock connection port 100' can be pulled along the longitudinal axis X' into its third position by a pulling force applied by an operator pulling the fluid transfer device 300, when coupled to the adaptor 1'.

Attention is now directed to FIGS. 6A-6E of the drawings illustrating the adaptor 1 which has been briefly described in connection with FIGS. 1A to 1C, 2A to 2E, 3A to 3I, and 4A to 4F, configured for connection to the syringe 500 via the syringe adaptor 400, as described in connection with FIGS. 2A to 2E. The adaptor 1 is configured to solve the problem of overpressure and underpressure in the syringe 500, which may arise in the syringe 500. The adaptor 1 comprises the first valve 40 positioned within the housing 20 and in fluid communication with the first outlet 24. The first valve 40 comprises a first valve seating member 41, which in the illustrated example is a valve seat, defining a first valve passage 42 formed therein. The first valve seating member 41 has a first surface 41A facing the first outlet 24 and an opposite second surface 41B, and the first valve passage 42 extends between the first surface 41A and the second surface 41B. The adaptor 1 comprises a first fluid path extending between the air channel 27 and the first outlet 24. The first fluid path passes through the first valve passage 42 and is selectively sealable by the first valve 40 at the first valve passage 42. The first valve 40 further comprises a first valve sealing member 43 having a central portion 44 and a skirt portion 45 extending radially outwards therefrom. The first valve sealing member 43 has a first surface 43A facing the first outlet 24, and an opposite second surface 43B facing the first valve seating member 41. The portion of the second surface 43B corresponding to the central portion 44 comprises flanges 46. The first valve 40 further comprises a rigid central member 47 positioned in the first valve passage 42, having a first end 47A and a second end 47B. The portion of the second surface 43B of the first valve sealing member 43 corresponding to the central portion 44 is attached to the first end 47A of the rigid central member 47 via flanges 46. The rigid central member 47 comprises bridges 47C (seen in FIG. 6E) connecting the rigid central member 47 to the first valve seating member 41.

The adaptor 1 further comprises the second valve 50 positioned within the housing 20 and in fluid communication with the second outlet 28. The second outlet 28 is defined by the opening 211 formed in the sidewall 210 of the outer body 200. The second valve 50 comprises a second valve seating member 51, which in the illustrated example is a valve seat, defining a second valve passage 52. The second valve seating member 51 has a first surface 51A facing the first valve seating member 41, and an opposite second surface 51B, and the second valve passage 52 extends between the first surface 51A and the second surface 51B. In the illustrated embodiment, the second surface 51B of the second valve seating member 51 forms a portion of an internal surface 26A of the liquid channel 26. The adaptor 1 comprises a second fluid path extending between the air channel 27 and the second outlet 28. The first fluid path passes through the second valve passage 52 and is selectively sealable by the second valve 50 at the second valve passage 52. The second valve 50 further comprises a second valve sealing member 53 having a central portion 54 and a skirt portion 55 extending radially outwards therefrom. The second valve sealing member 53 has a first surface 53A facing the first valve seating member 41, and an opposite second surface 53B facing the second valve seating member 51. The second end 47B of the of the rigid central member 47 rests on the central portion 54 of the second valve sealing member 53.

It is to be understood herein that the first and the second valves have been described above having the structures as shown in FIGS. 6A-6E and as described herein for the purpose of illustration only, and that the valves can have another structure serving the same purpose, an example of which (especially the first valve) can be seen in FIGS. 5A-5D. In other words, it is to be understood herein that the valves (especially the first valve) that can be seen in FIGS. 5A-5D can be used in the examples illustrated in FIGS. 6A-6E.

Figure 6A:
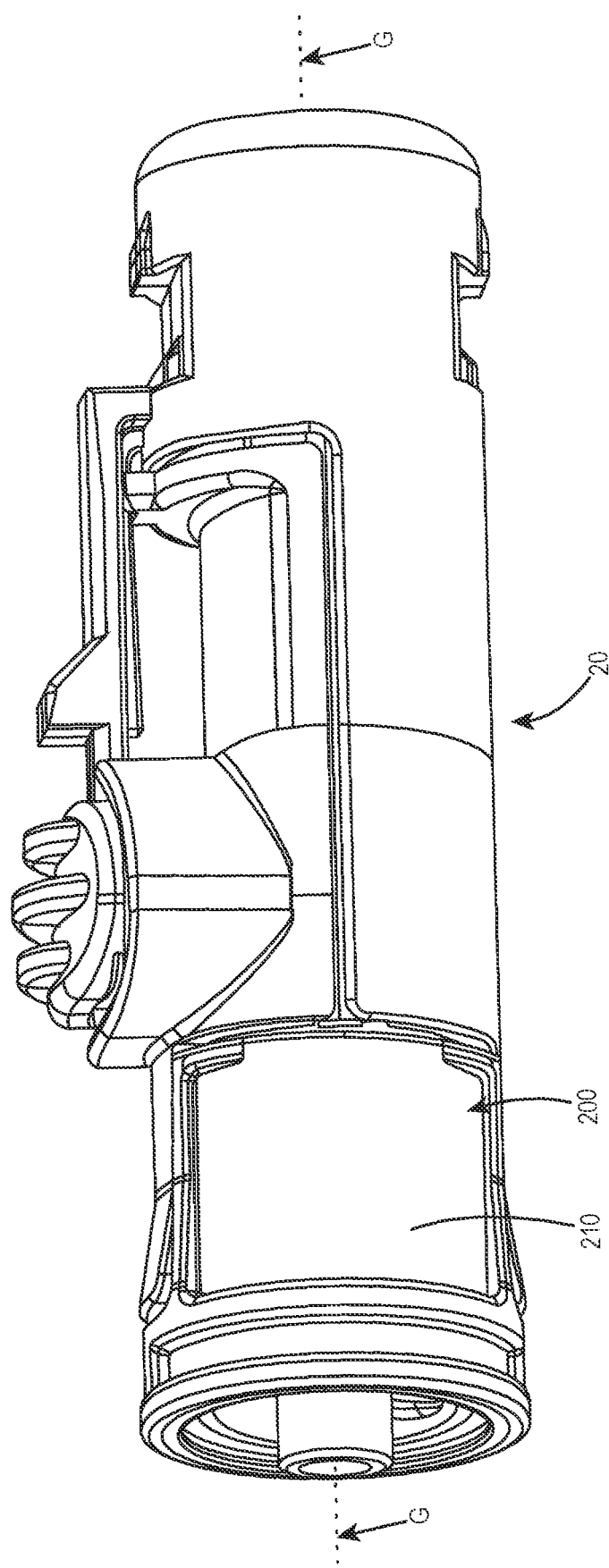
FIG. 6A is a side perspective view of the adaptor of FIG. 1A.
Figure 6B:
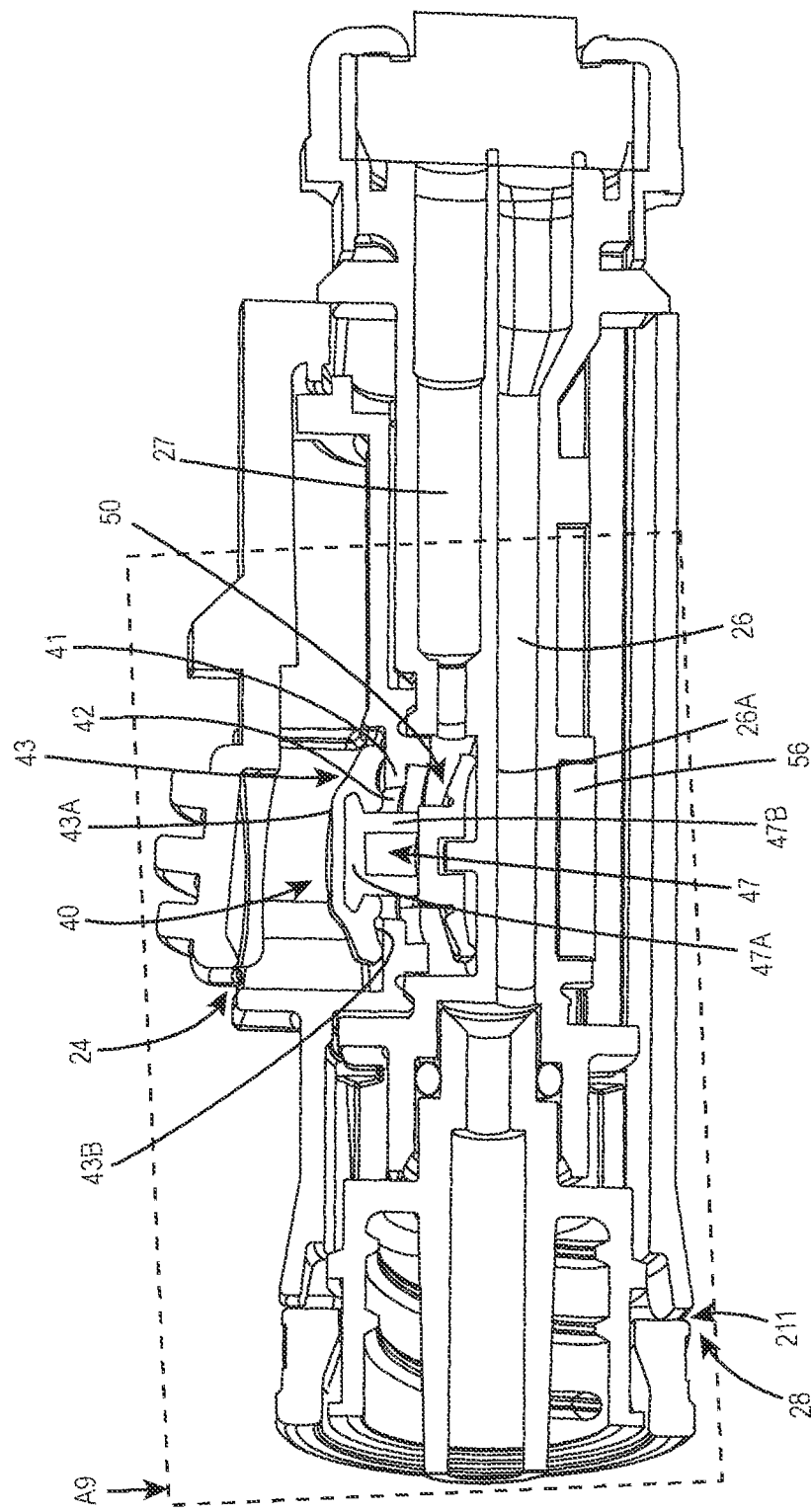
FIG. 6B is a cross-sectional view along line G-G in FIG. 6A.
Figure 6C:
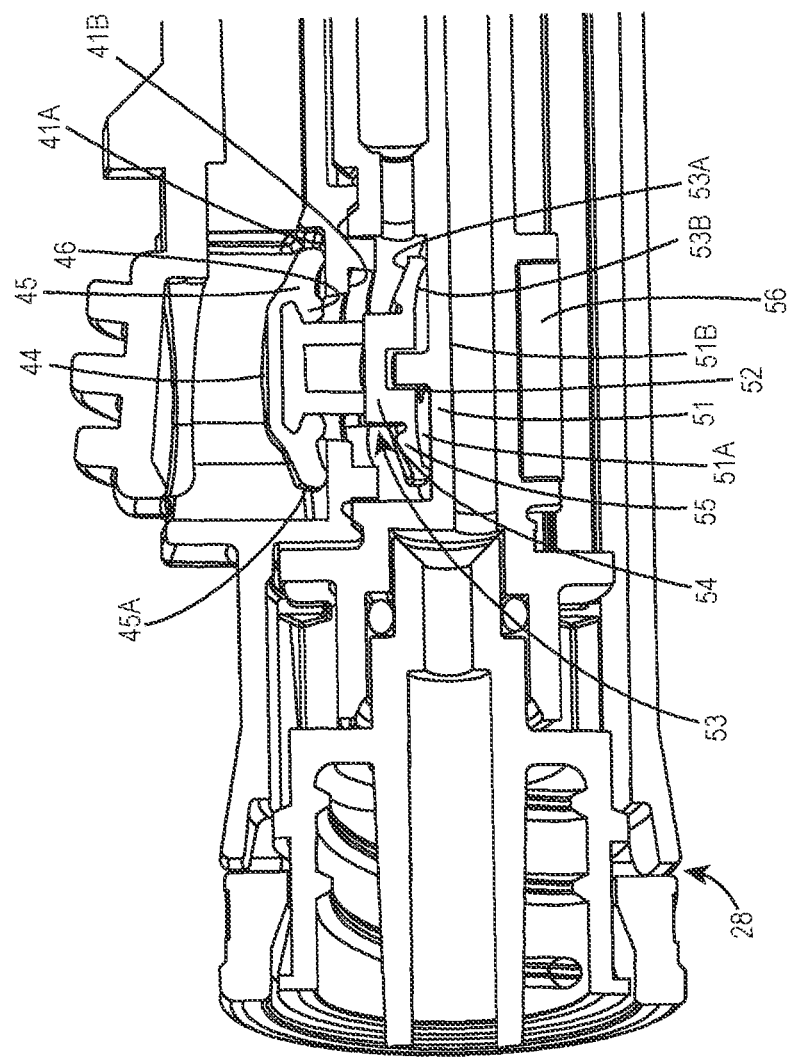
FIG. 6C is an enlarged view of section A9 of FIG. 6B.
Figure 6D:
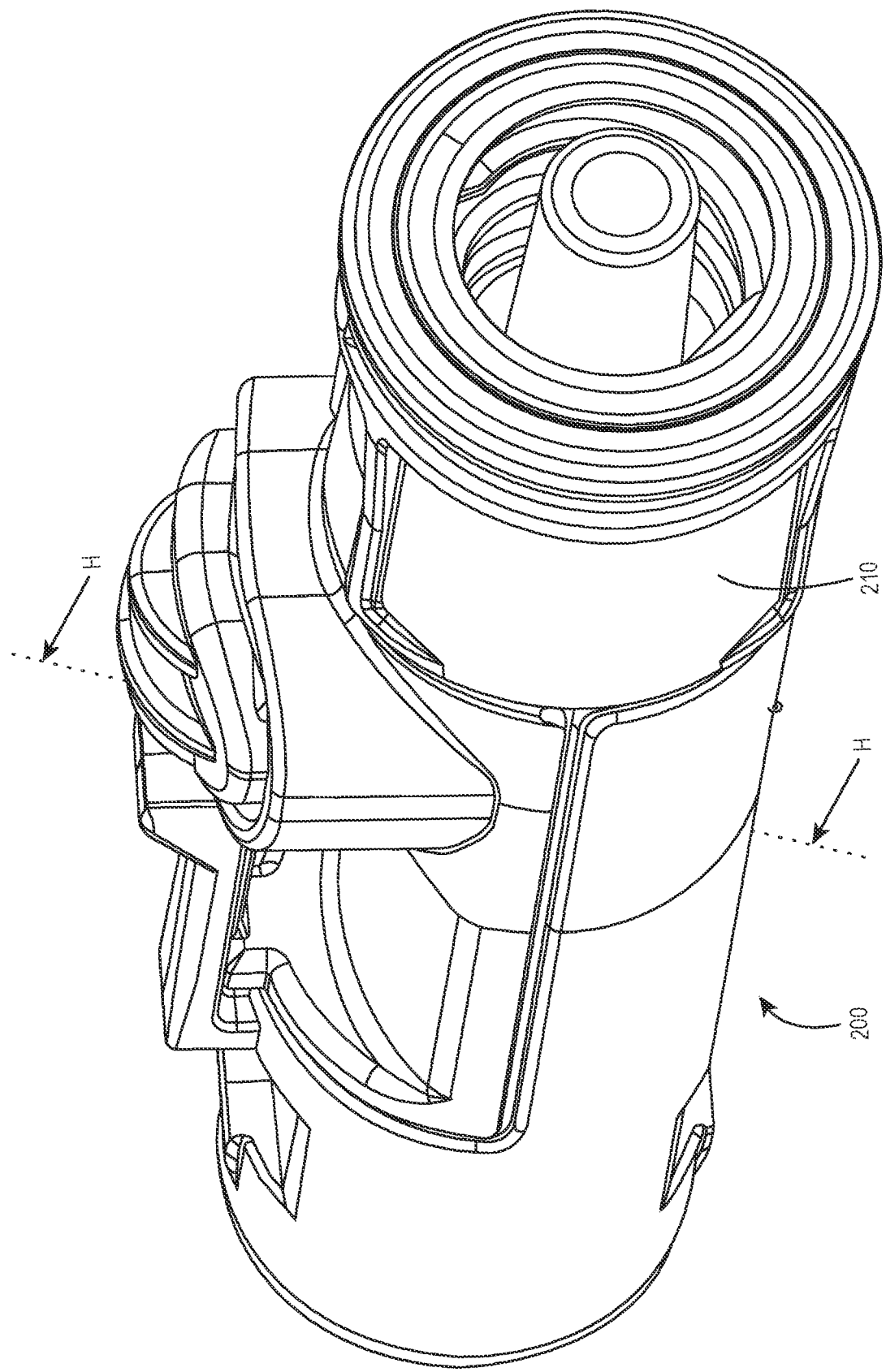
FIG. 6D is a front perspective view of the adaptor of FIG. 6A.

As can be seen in FIGS. 6B and 6C, the first valve 40 is normally at its first valve normally closed state, and a rim 45A of the skirt portion 45 rests on the first surface 41A of the first valve seating member 41, thereby sealing the first valve passage 42, i.e., not allowing air flow between the air channel 27 and the first outlet 24. When an overpressure is created in the air channel 27, as described above with reference to FIGS. 2A-2E, the air pressure within the air channel 27 exerts force on the second surface 43B of the first valve sealing member 43 via the first valve passage 42. When the air pressure within the air channel 27 exceeds a first predetermined threshold (e.g., having a value of 0.5 bar), the force applied thereby on the second surface 43B causes the rim 45A of the skirt portion 45 to automatically lift up from the first surface 41A of the first valve seating member 41 thereby displacing the first valve 40 into its first valve open state and unsealing the first valve passage 42. At this first valve open state of the first valve 40, the air flows from the air channel 27 through the first valve passage 42 and escapes in the ambiance via the first outlet 24, thereby releasing the overpressure from the air channel 27. When the air pressure being released from the air channel 27 falls below the first predetermined threshold, the rim 45A again returns to its original position thereby automatically displacing the first valve 40 into its first valve normally closed state. It is to be understood herein that the first predetermined threshold is greater than the ambient pressure for the air to flow from the air channel 27 into the ambiance. Further, the skirt portion 45 of the first valve sealing member 43 is a resilient member, whose resilience, along with its geometry and the parts surrounding it, is selected on the basis of the first predetermined threshold, which further depends on how much pressure is intended to be a maximum pressure that can be built within the air channel 27 before being released into the ambiance.

Figure 6E:
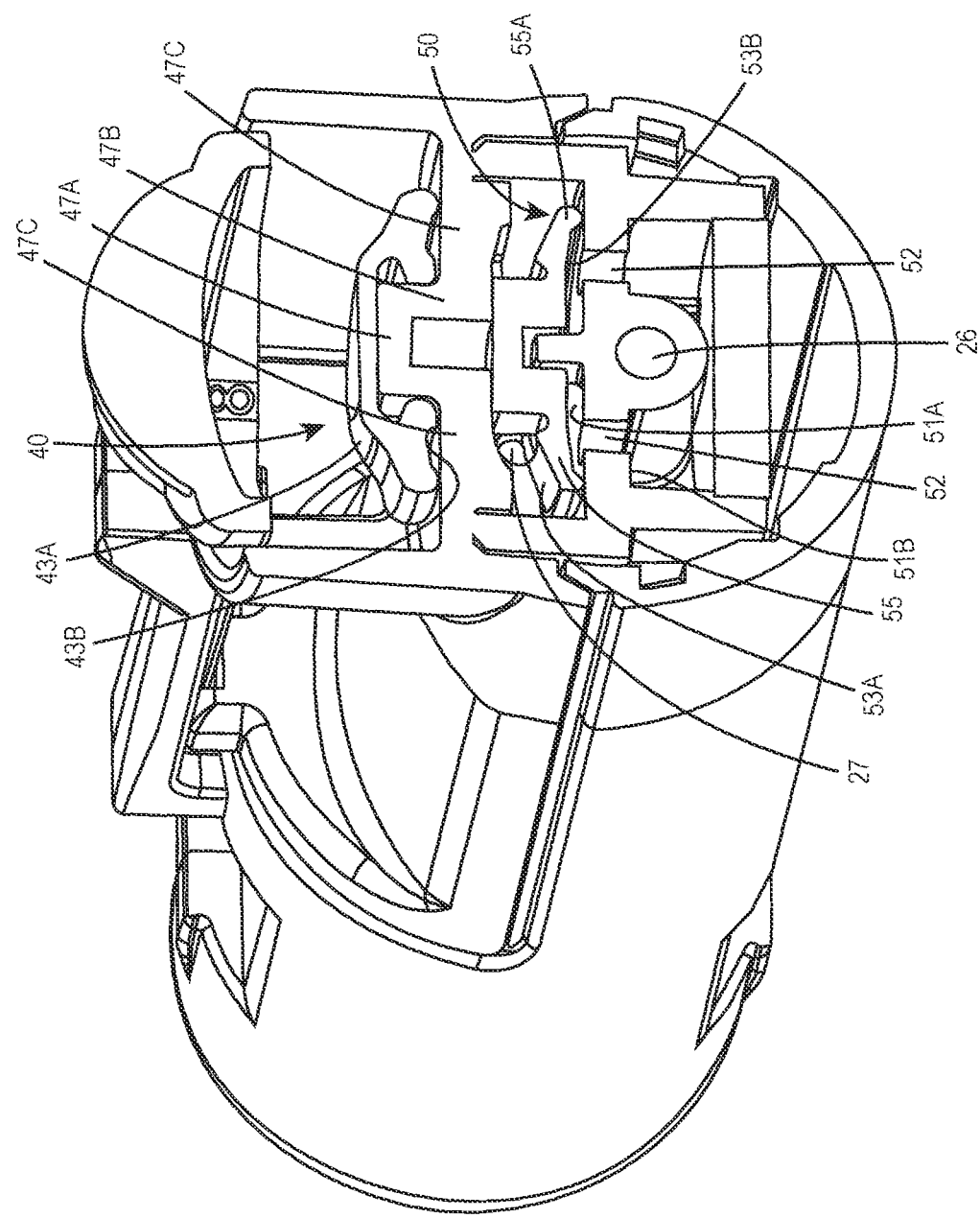
FIG. 6E is cross-sectional view along line H-H in FIG. 6D.

As further shown in FIGS. 6C and 6E, the second valve 50 is normally at its second valve normally closed state, and a rim 55A of the skirt portion 55 rests on the first surface 51A of the second valve seating member 51, thereby sealing the second valve passage 52, i.e., not allowing air flow between the air channel 27 and the second outlet 28. The air pressure within the air channel 27 exerts force on the first surface 53A of the second valve sealing member 53 against the force applied by the ambient pressure on the second surface 53B of the second valve sealing member 53 via the second outlet 28, an air filter 56, and the second valve passage 52, thereby keeping the rim 55A engaged with the first surface 51A of the second valve seating member 51. When an underpressure is created in the air channel 27 and the air pressure within the air channel 27 falls below a second predetermined threshold (e.g., having a value of 0.2 bar), the force applied by the ambient pressure on the second surface 53B of the second valve sealing member 53 activates the second valve 50, thereby causing the rim 55A of the skirt portion 55 to automatically lift up from the first surface 51A of the second valve seating member 51 thereby displacing the second valve 50 into its second valve open state and unsealing the second valve passage 52. At this second valve open state of the second valve 50, the air flows from the ambiance into the air channel 27 through the second outlet 28, the filter 56 and the second valve passage 52, thereby balancing the underpressure created in the air channel 27. When the air pressure in the air channel 27 rises above the second predetermined threshold, the rim 55A returns to its original position thereby automatically displacing the second valve 50 into its second valve normally closed state. It is to be understood herein that the second predetermined threshold is lesser than the ambient pressure for the air to flow from the ambiance into the air channel 27. Further, the skirt portion 55 of the second valve sealing member 53 is a resilient member, whose resilience, along with its geometry and the parts surrounding it, is selected on the basis of the second predetermined threshold, which further depends on how much pressure is intended to be a minimum pressure that can be allowed within the air channel 27 before being balanced from the ambiance.

It is to be understood herein that when the pressure within the air channel 27 is between the first predetermined threshold and the second threshold pressure, both the first valve 40 and the second valve 50 are in their respective closed states. In particular, when the pressure within the air channel 27 is equal to the ambient pressure, both the first valve 40 and the second valve 50 are in their respective closed states.

It is to be further understood herein that at the first valve open state, the second valve 50 remains in its second valve normally closed state, and at the second valve open state, the first valve 40 remains at its first valve normally closed state.

Attention is now directed to FIGS. 7A-7E of the drawings illustrating an adaptor 1" according to another example of the presently disclosed subject matter, configured for connection to the syringe 500 via the syringe adaptor 400. The adaptor 1" has at least some of the elements corresponding to those of the adaptor 1 as described above, and have been depicted by corresponding reference numerals for ease of understanding. Alternative to the first valve 40 and the second valve 50 as of the adaptor 1, the adaptor 1" comprises a valve arrangement 60 in fluid communication with the ambiance via the first outlet 24" as well as the second outlet 28". The valve arrangement 60 is a dual function valve configured to perform the functioning of both of the first valve 40 and the second valve 50. For instance, the adaptor 1" is configured to solve the problem of overpressure and underpressure in the syringe 500, which may arise in the syringe 500, in that, the valve arrangement 60 is configured to facilitate escape of air from within the valve arrangement 60 to the ambiance in case of overpressure, and to facilitate entry of air from the ambiance into the valve arrangement 60 in case of underpressure.

The valve arrangement 60 comprises a first valve seating member 61, which in the illustrated example is a valve seat, defining a first valve passage 62. The first valve seating member 61 has a first surface 61A facing the outlet 24" and an opposite second surface 61B, and the first valve passage 62 extends between the first surface 61A and the second surface 61B. The valve arrangement further comprises a second valve seating member 71, which in the illustrated example is a valve seat, defining a second valve passage 72. The second valve seating member 71 has a first surface 71A facing the first valve seating member 61 and an opposite second surface 71B, and the second valve passage 72 extends between the first surface 71A and the second surface 71B. The valve arrangement 60 further comprises a sealing member 63 including a central member 64 extending between the first valve seating member 61 and the second valve seating member 71. The central member 64 has a first end 65 positioned towards the first valve seating member 61 and having a face 65A, facing the second surface 61B of the first valve seating member 61, constituting a sealing member first portion. The central member 64 has an opposite second end 66 positioned towards the second valve seating member 71 and having a face 66A facing the first surface 71A of the second valve seating member 71. The sealing member 63 comprises a resilient skirt portion 67 diverging from a periphery of the second end 66 towards the first surface 71A of the second valve seating member 71. The skirt portion 67 extends between a first rim 68 connected to the second end 66 of the central member 64, and a second rim 69 constituting a sealing member second portion. The skirt portion 67 has a first surface 67A facing the first valve seating member 61 and an opposite second surface 67B facing the second valve seating member 71. The first surface 71A of the second valve seating member 71 comprises a protrusion 73 corresponding to a groove 66B formed in the face 66A of the second end 66 of the central member 64. The sealing member 63 is so positioned in the valve arrangement 60 that the groove 66B securely receives therewithin the protrusion 73 to prevent movement of the sealing member 63 in a plane parallel to the first and the second valve seating members 61 and 71. The valve arrangement 60 further comprises a sidewall 70 extending from the first valve seating member 61 to the second valve seating member 71. The valve arrangement 60 can be in fluid communication with a fluid transfer system where pressure needs to be maintained within a range via the sidewall 70, for example the air channel 27" in the illustrated example. However, in other examples, the valve arrangement 60 can be used to serve similar purposes in conjunction with fluid transfer systems not related to medical systems.

Figure 7A:
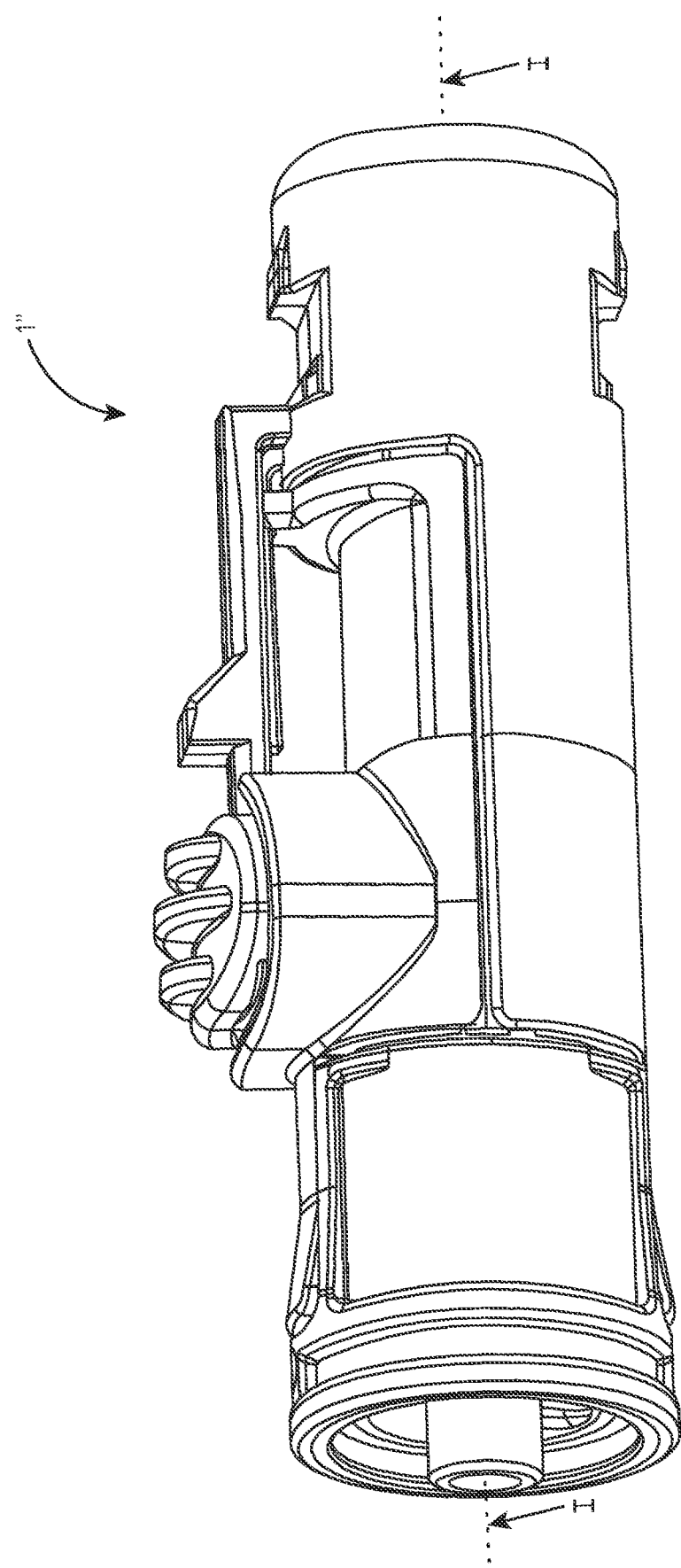
FIG. 7A is a side perspective view of an adaptor according to a third example of the presently disclosed subject matter.
Figure 7B:
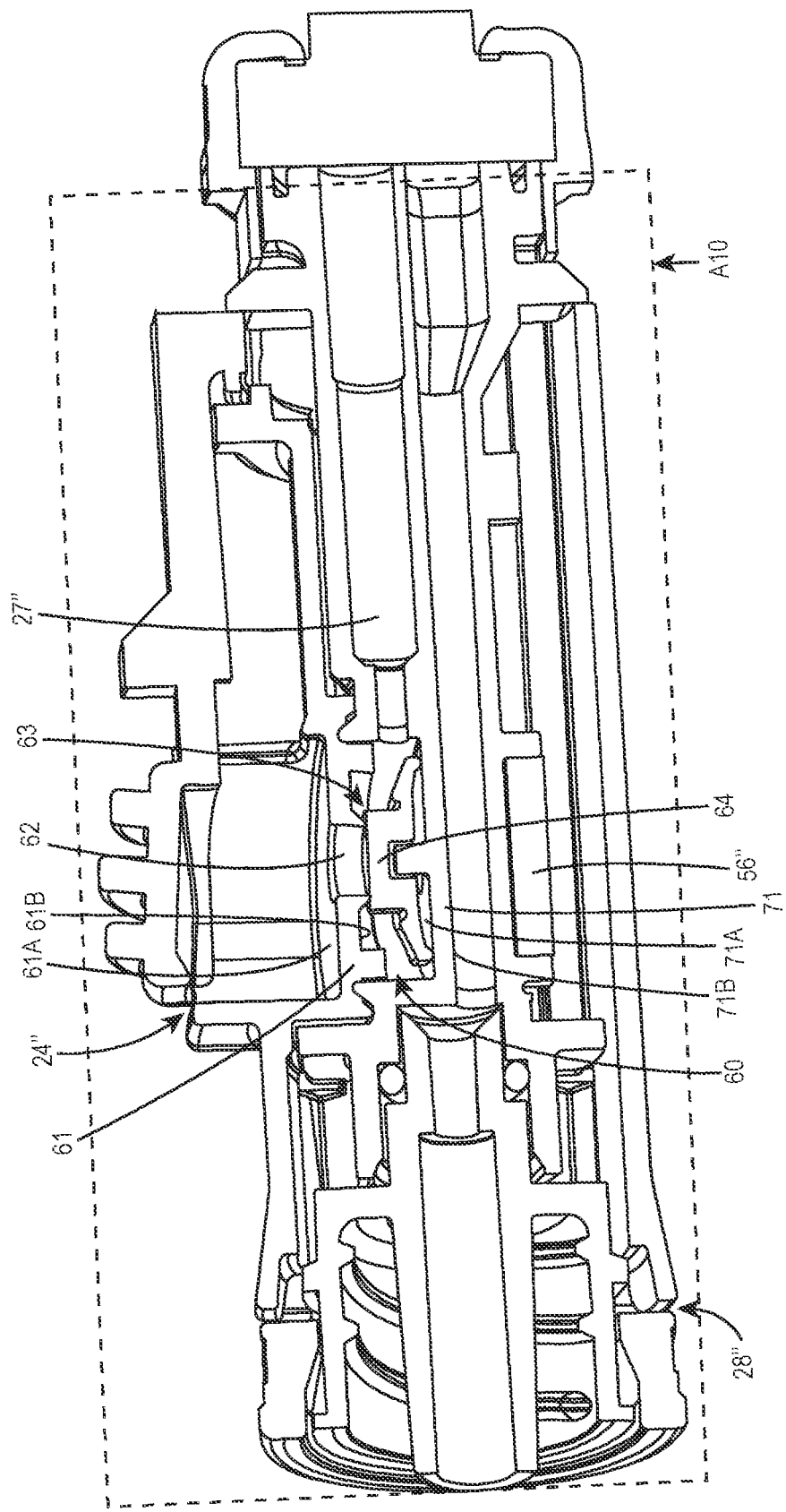
FIG. 7B is a cross-sectional view along line I-I in FIG. 7A.
Figure 7C:
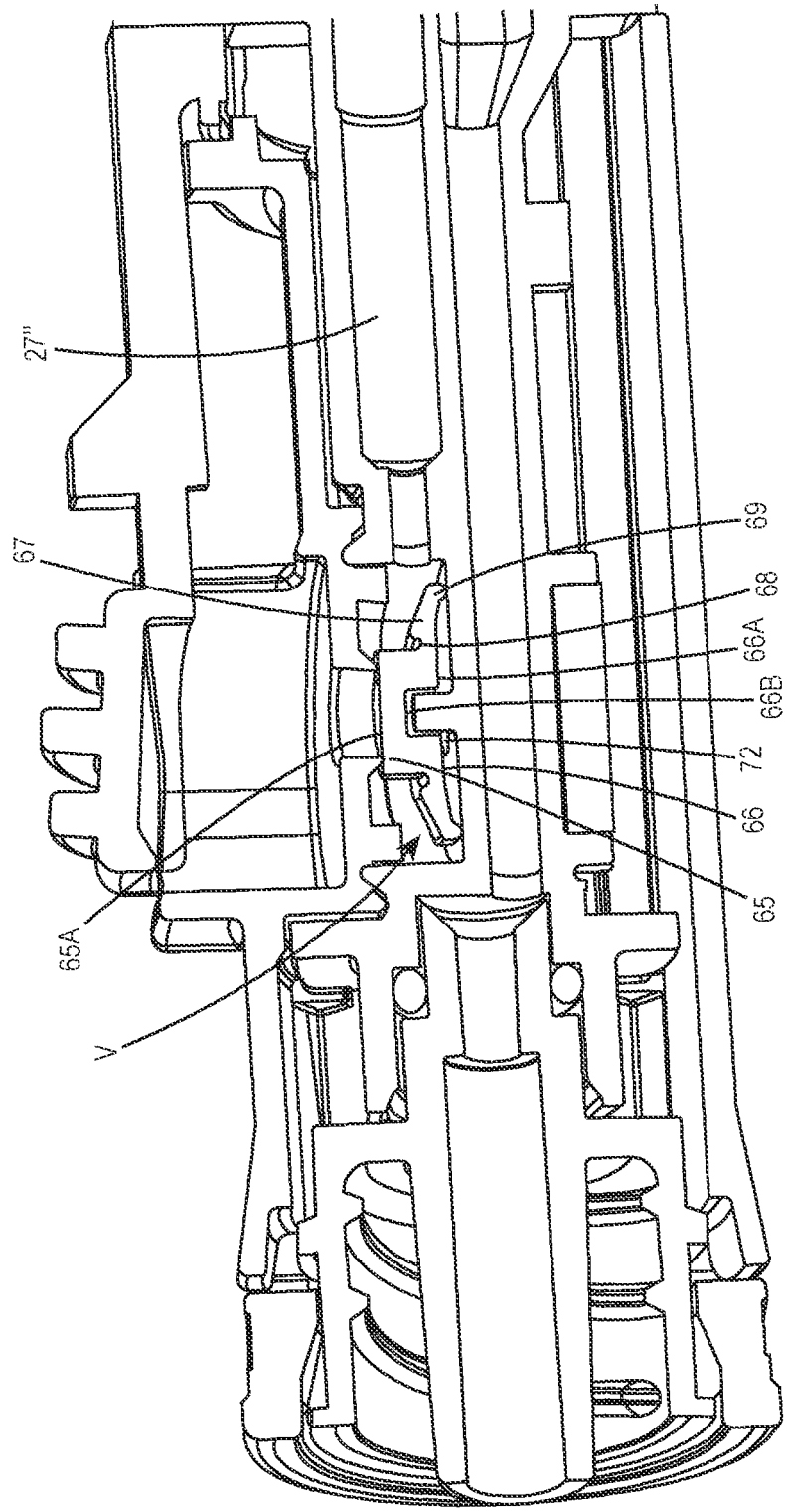
FIG. 7C is an enlarged view of section A10 of FIG. 7B.
Figure 7D:
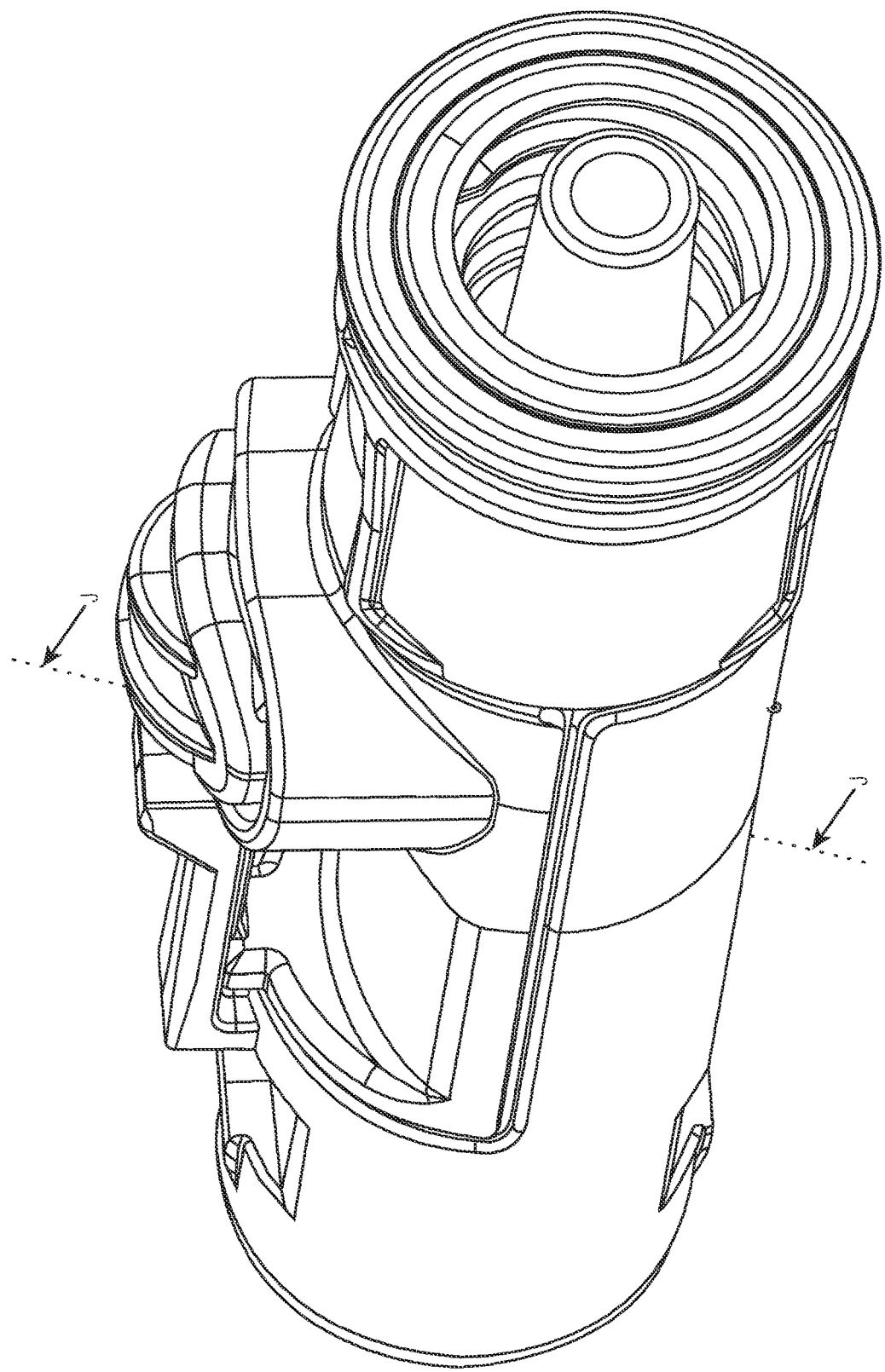
FIG. 7D is a front perspective view of the adaptor of FIG. 7A.
Figure 8A:
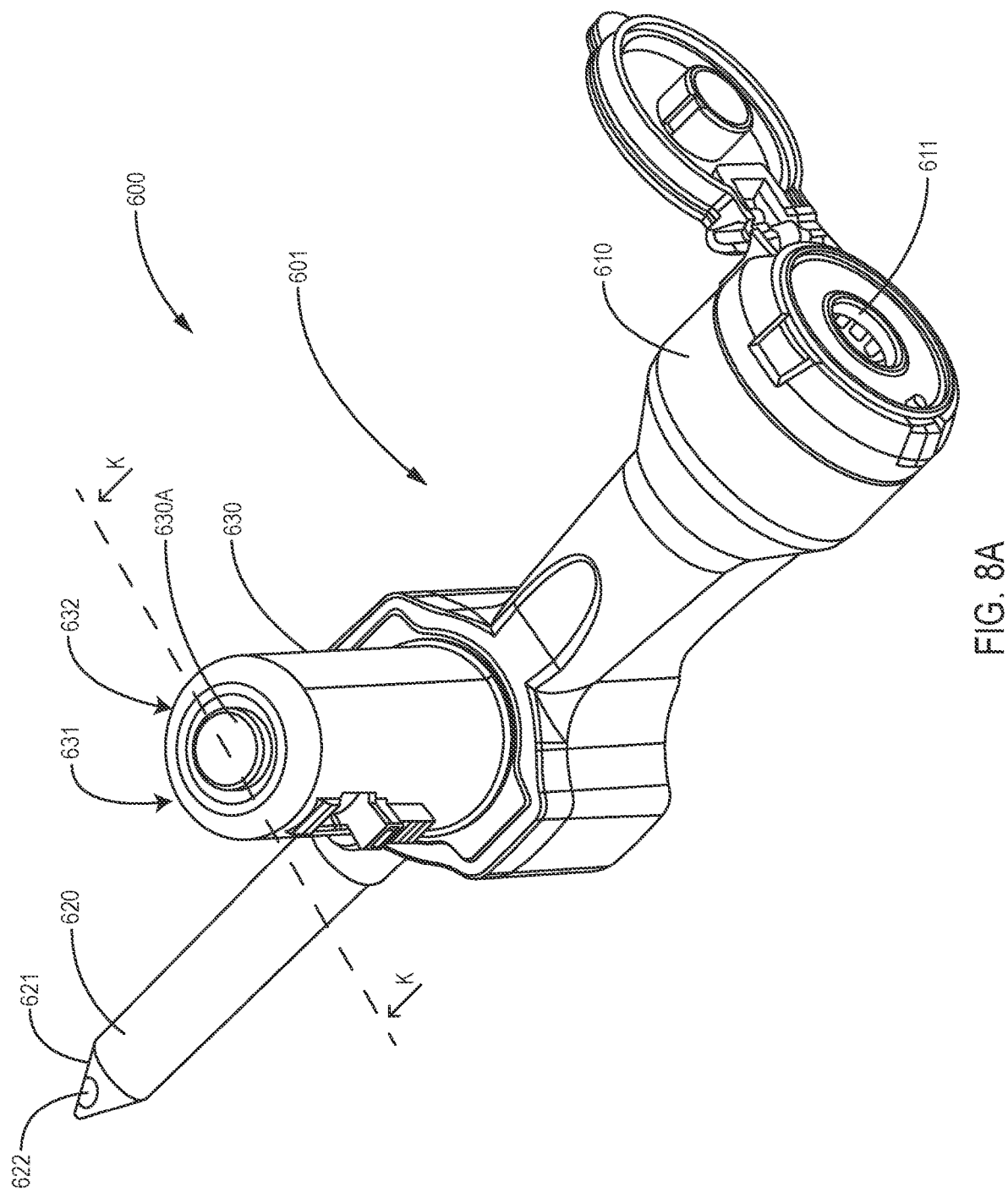
FIG. 8A is a top perspective view of an adaptor according to a fourth example of the presently disclosed subject matter.
Figure 8B:
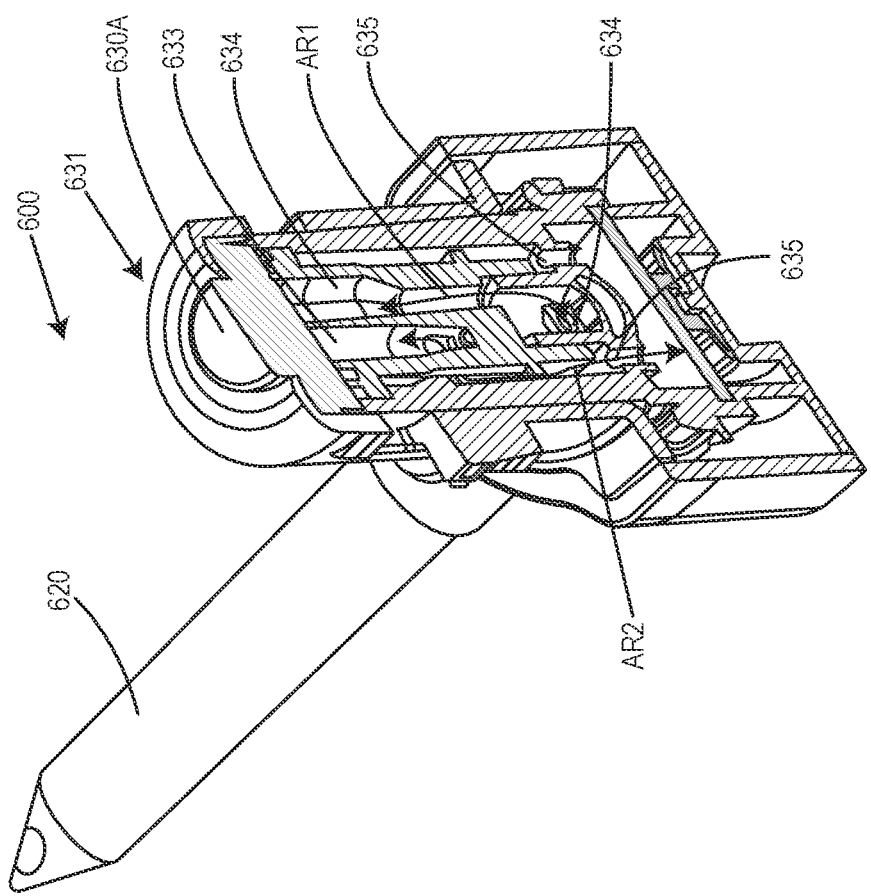
FIG. 8B is a cross-sectional view along line K-K in FIG. 8A.
Figure 8C:
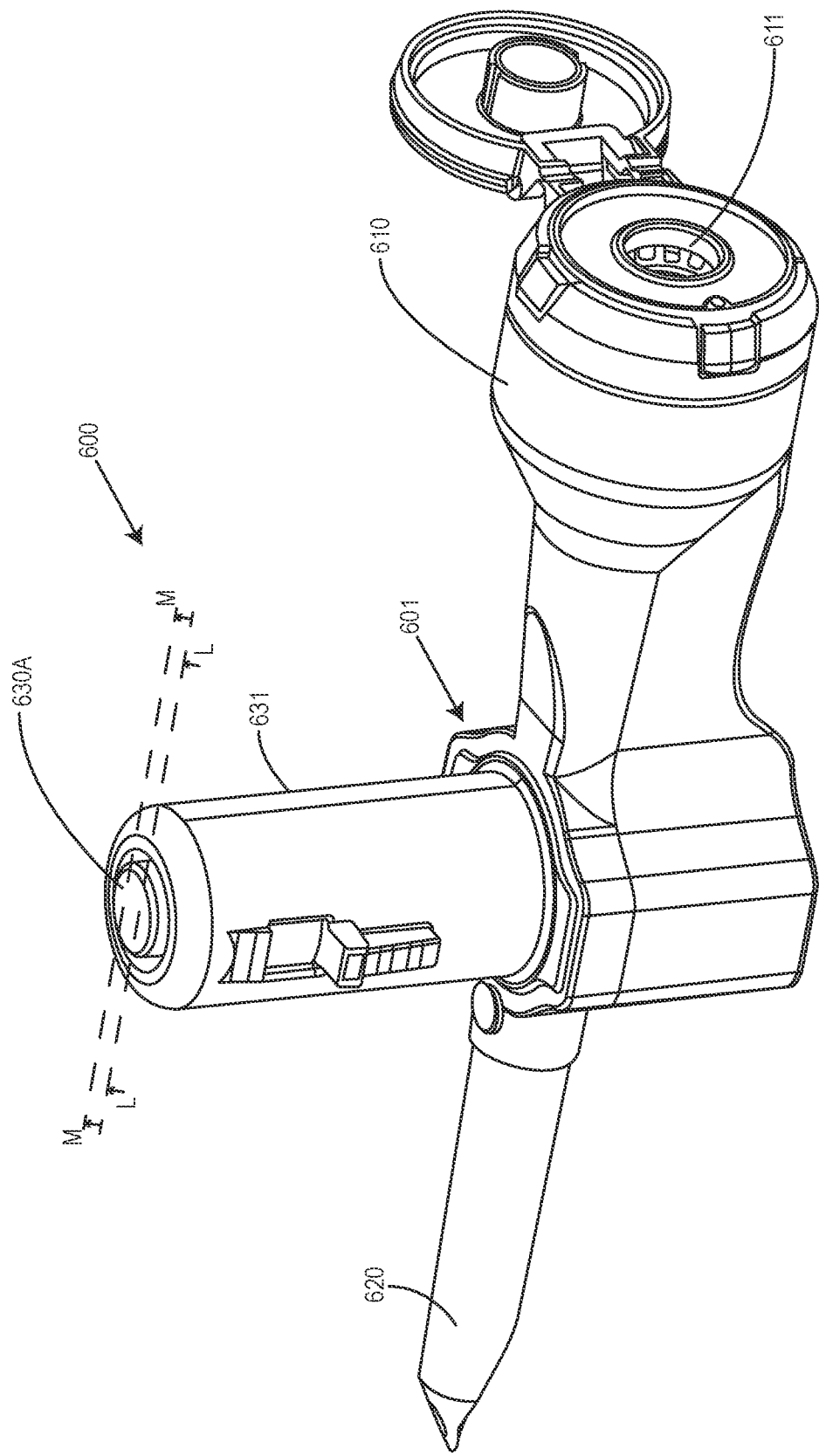
FIG. 8C is a side perspective view of the adaptor of FIG. 8A.
Figure 8D:
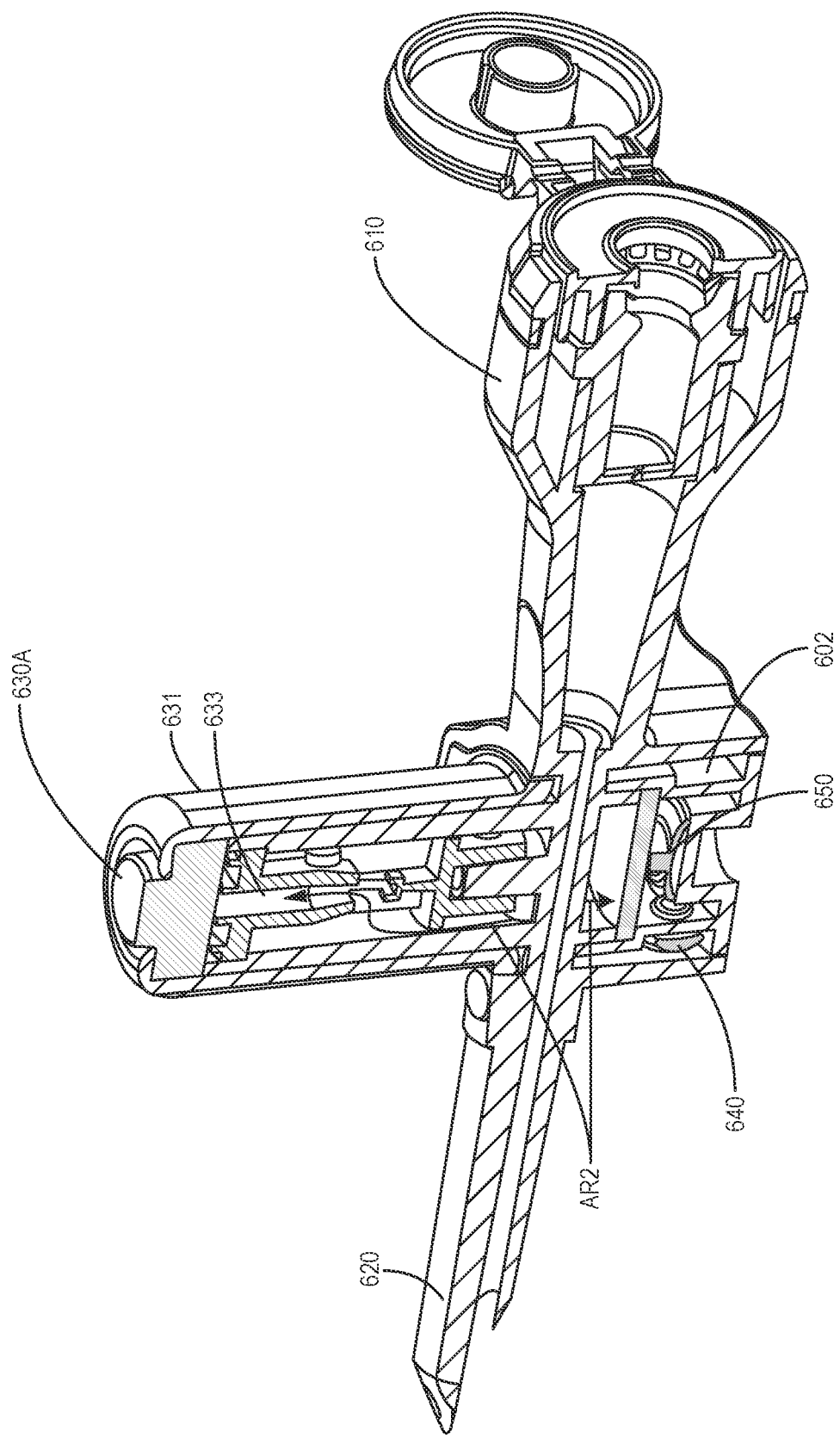
FIG. 8D is a cross-sectional view along line L-L in FIG. 8C.
Figure 8E:
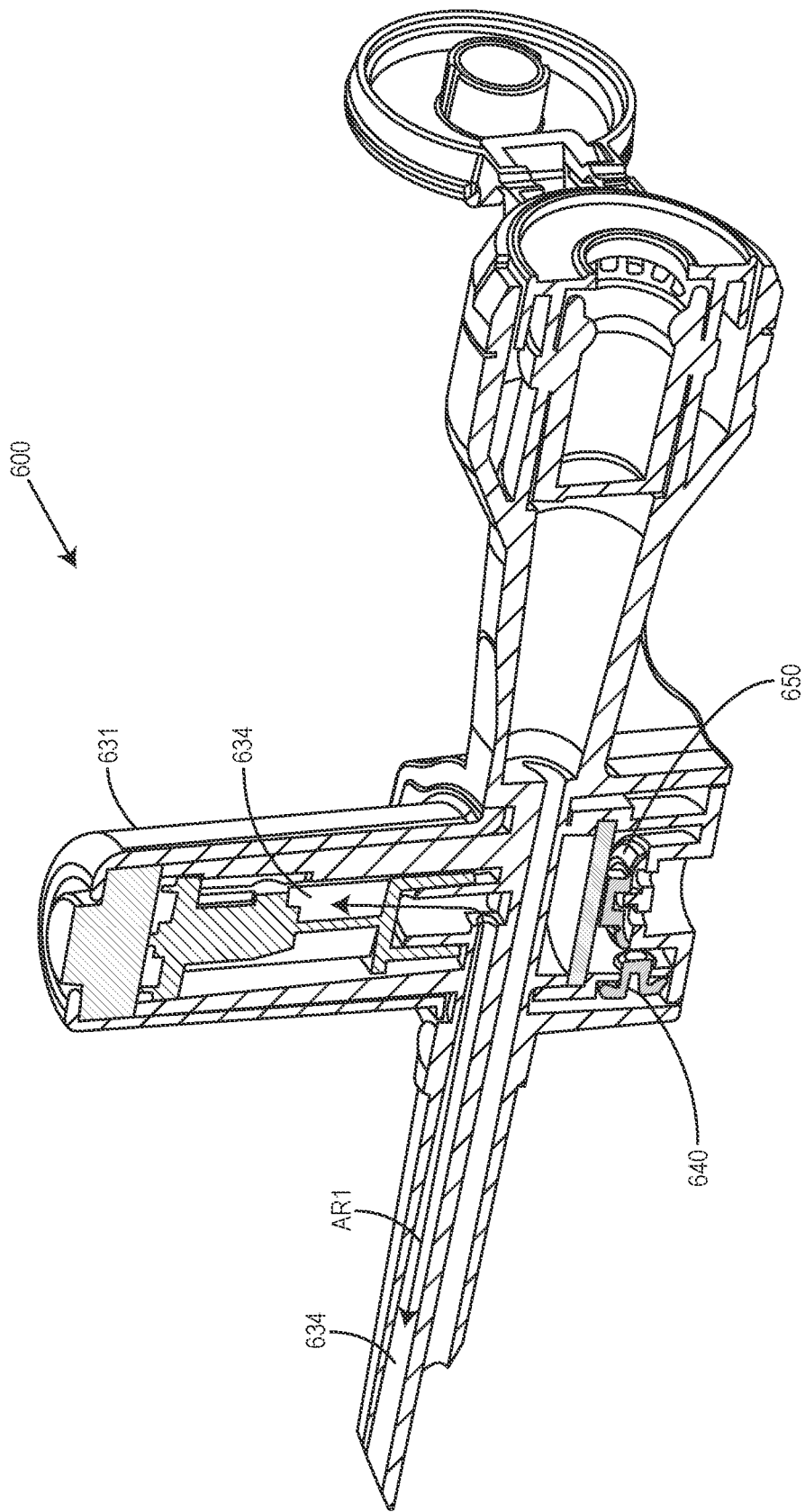
FIG. 8E is a cross-sectional view along line M-M in FIG. 8C.

As can be seen in FIGS. 7C and 7D, the valve arrangement 60 is normally at its normal fully closed state. The sealing member first portion 65A engages with the second surface 61B of the first valve seating member 61, thereby sealing the first valve passage 62. Also, the sealing member second portion 69 engages with the first surface 71A of the second valve seat, thereby sealing the second valve passage 72. At this state, there is a gap G between the face 66A and the first surface 71A of the second valve seating member 71. Further, at this normal fully closed state, the volume V defined between the second surface 61B of the first valve seating member 61, the sealing member 63, the first surface 71A of the second valve seating member 71, and the sidewall 70 defines the volume within the valve arrangement 60.

When an overpressure is created in the volume V, the air pressure within the valve arrangement exerts force on the first surface 67A of the skirt portion 67 of the sealing member 63. When the air pressure within the valve arrangement 60 exceeds a first predetermined threshold, the force applied thereby on the first surface 67A causes the first rim 68 of the skirt portion 67 flexes towards the second valve seating member 71 such that the face 66A of the second end 66 of the central member 64 flexes into the gap G towards the first surface 71A of the second valve seating member 71. This causes the sealing member first portion 65A to disengage from the second surface 61B of the first valve seating member 61, thereby unsealing the first valve passage 62 and automatically displacing the valve arrangement 60 into its first valve open state. At this first valve open state, the air flows from the volume V through the first valve passage 62 and escapes into the ambiance via the first outlet 24", thereby releasing the overpressure from the valve arrangement 60. When the air pressure being released from the valve arrangement 60 falls below the first predetermined threshold, the first rim 68 of the skirt portion 67 flexes back to its normal position thereby automatically displacing the valve arrangement 60 into its normal fully closed state. It is to be understood herein that the first predetermined threshold is greater than the ambient pressure for the air to flow from the valve arrangement 60 into the ambiance, and is selected based on how much pressure is intended to be a maximum pressure that can be built within the valve arrangement 60 before being released into the ambiance.

At the normal fully closed state of the valve arrangement 60, the air pressure within the valve arrangement 60 exerts force on the first surface 67A of the skirt portion 67 against the force applied by the ambient pressure on the second surface 67B of the skirt portion 67 via the second outlet 28", an air filter 56", and the second valve passage 72, thereby keeping the sealing member second portion 69 engaged with the first surface 71A of the second valve seating member 71.

When an underpressure is created in the volume V, the force applied by the air pressure within the valve arrangement 60 on the first surface 67A of the skirt portion 67 decreases. When the air pressure within the valve arrangement 60 falls below a second predetermined threshold, the sealing member second portion 69 automatically lifts up from the first surface 71A of the second valve seating member 71, thereby displacing the valve arrangement 60 into its second valve open state and unsealing the second valve passage 72. At this second valve open state, the air enters from the ambiance into the volume V via the second outlet 28", thereby balancing the underpressure created in the valve arrangement 60. When the air pressure in the valve arrangement 60 rises above the second predetermined threshold, the sealing member second portion 59 returns to its original position thereby automatically displacing the valve arrangement 60 into its normal fully closed state. It is to be understood herein that the second predetermined threshold is lesser than the ambient pressure for the air to flow from the ambiance into the valve arrangement 60, and is selected based on how much pressure is intended to be a minimum pressure that can be allowed within the valve arrangement 60 before being balanced from the ambiance.

It is to be understood herein that when the pressure within the valve arrangement 60 is between the first predetermined threshold and the second threshold pressure, the valve arrangement 60 is in its fully closed state. In particular, when the pressure within the valve arrangement 60 is equal to the ambient pressure, the valve arrangement 60 is in its fully closed state.

It is to be further understood that the resilience of the skirt portion 67 is selected based on the first predetermined threshold and the second predetermined threshold. It is to be further understood herein that at the first valve open state of the valve arrangement 60, the sealing member second portion 69 seals the second valve passage 72, and at the second valve open state, the sealing member first portion 65A seals the first valve passage 62.

The valve arrangement 60 as described above can be used with any fluid transfer apparatus that requires an air pressure to be maintained within a range. Also, the valve arrangement 60 as described above can be used with the adaptor 1 as described above with reference to FIGS. 6A to 6D, wherein the first valve 40 and second valve 50 can be realized as the valve arrangement 60, with the sealing members 43 and 53 being configured as a single common sealing member, such as sealing member 63.

It should be understood herein that the application of the dual function valve 60 is advantageous over application of two valves 40 and 50, in that, a single sealing member needs to be manufactured and assembled instead of two separate sealing members. Further, the single valve arrangement occupies lesser space than the two separate valves within the housing of the adaptor.

Attention is now directed to FIGS. 8A-8E of the drawings illustrating an adaptor 600, which, in this non-limiting example, is a spike adaptor configured to be connected between at least two other devices, at a time, in order to establish a fluid connection therebetween when the adaptor 600 is the intermediate device. It is noted that spike adaptors and their basic functionality are generally known in the art and are described herein briefly for the sake of clarity and completeness.

As shown in the figures, the adaptor 600 includes a body 601 having three body portions 610, 620 and 630 each being terminated with at least one fluid inlet and/or outlet. The body portion 610 includes a spike port 611 configured to receive therein a medical spike and establish fluid communication between the medical spike and the adaptor 600. The body portion 610 is therefore referred to as the spike receiving portion. The medical spike will basically form the inlet and/or outlet into a medical device such as an infusion set configured to be connected to a patient body to transfer a drug thereto.

The body portion 620 is configured as a second medical spike 621 terminated with at least one fluid inlet/outlet 622. Therefore, the body portion 620 is referred to as a spike terminal portion. The medical spike 621 is configured to be connected to a spike port of a medical device and establish a fluid communication therewith via the at least one fluid inlet/outlet 622 such that a fluid communication is established between the medical device and the adaptor 600. For example, the medical device can be an IV bag having a spike port that receives the spike 621 and such that a fluid communication is established, through the adaptor 600, between the IV bag connected to the spike 621 and the patient connected to the spike received in the spike port 611.

The body portion 630 is configured as a fluid transfer device 631 utilizing a contamination-free fluid transfer. The contamination-free fluid transfer device 631, referred to as a drug injection portion of the adaptor 600, is terminated with a fluid inlet 632 configured to connect to an external fluid transfer device, such as a syringe, to receive therefrom a fluid and transport it through the adaptor 600, via dedicated internal ducts/channels, to another external device, such as an IV bag, connected to the spike 621. This fluid transfer, controlled by fluid transfer device 631, can be used to transfer a drug into an IV bag, possibly containing another drug or saline water, and also to transfer a liquid from the IV bag to the syringe.

The syringe can be similar to the syringe 500, as described above, and include at least some of the features of the syringe 500, and particularly the air needle, the liquid needle, the air chamber, and the liquid chamber. As described above, the syringe can be used to deliver a liquid from the syringe as well as to extract a liquid into the syringe. When the syringe is connected to the adaptor 600, for example via a syringe adaptor similar to the syringe adaptor 400 described above, a fluid communication is established between the air chamber of the syringe and an air channel 633 of the fluid transfer device 631 via the air needle, and a fluid communication is established between the liquid chamber of the syringe and a liquid channel 634 of the fluid transfer device 631 via the liquid needle. The adaptor 600 includes a septum 630A configured to facilitate introduction of the needles into the fluid transfer device 631.

In some medical procedures, it is required that a syringe is used to extract a volume of saline water from an IV bag, and then replacing the extracted volume of saline water with a drug from a syringe (generally a different one). For a single spike adaptor to be able to be used for both the operations between the syringe(s) and the IV bag, the spike adaptor needs to be configured to facilitate flow of air between the air chamber of the syringe and the ambiance in both directions, i.e., discharge of air from the air chamber as well as intake of air into the air chamber, especially when the syringes to be used are similar to syringe 500, i.e., having air chamber which is sealed from fluid communication with the ambiance other than through an air needle extending from the air chamber to an exterior of the syringe.

A flow of the liquid (drug and saline water) between the syringe and the IV bag through the adaptor 600 is depicted by double sided arrow AR1, and a flow of air between the air channel 633 and a valve arrangement (detailed further below) associated with the adaptor 600 is depicted by arrow AR2. When the syringe is used to deliver the liquid through the adaptor 600, the air pressure in the air chamber of the syringe reduces, and when the syringe is operated in the opposite direction, i.e., to extract a liquid through the adaptor 600, the air pressure in the air chamber of the syringe increases. The pressure, if not controlled, can render the syringe at least partially inoperable. For instance, if the reduced air pressure in the air chamber is not compensated, the syringe and the adaptor 600 would not be usable for delivering the liquid from the syringe through the adaptor 600, and if the increased pressure in the air chamber is not discharged, the syringe and the adaptor 600 would not be usable to extract the liquid into the syringe through the adaptor 600, thereby limiting the use/operability of the adaptor. The adaptor 600, thus, includes valves 640 and 650 to regulate the pressure in the air channel of the adaptor 600, and consequently in the air chamber of the syringe, as described below.

Figure 9A:
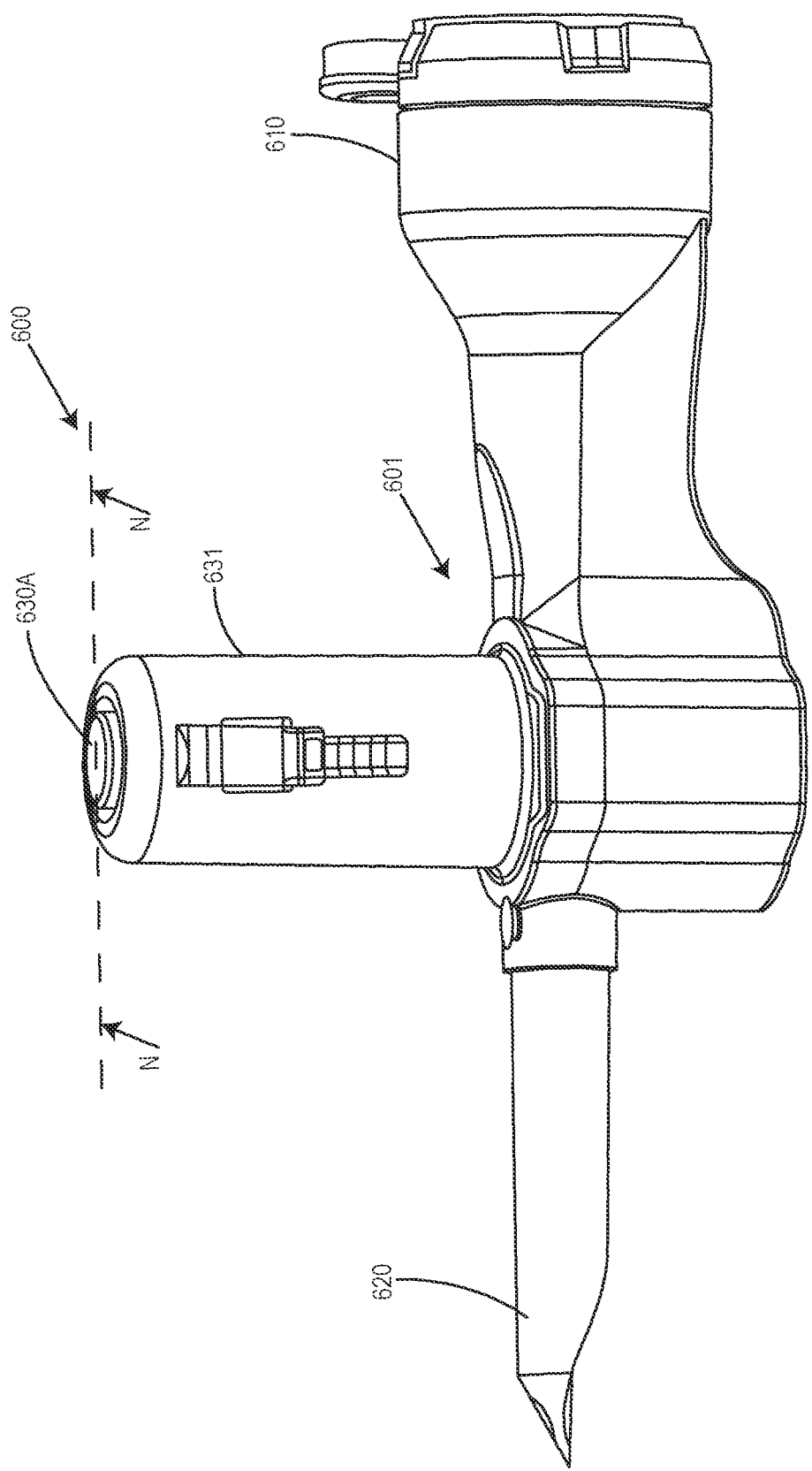
FIG. 9A is a side view of the adaptor of FIG. 8A.
Figure 9B:
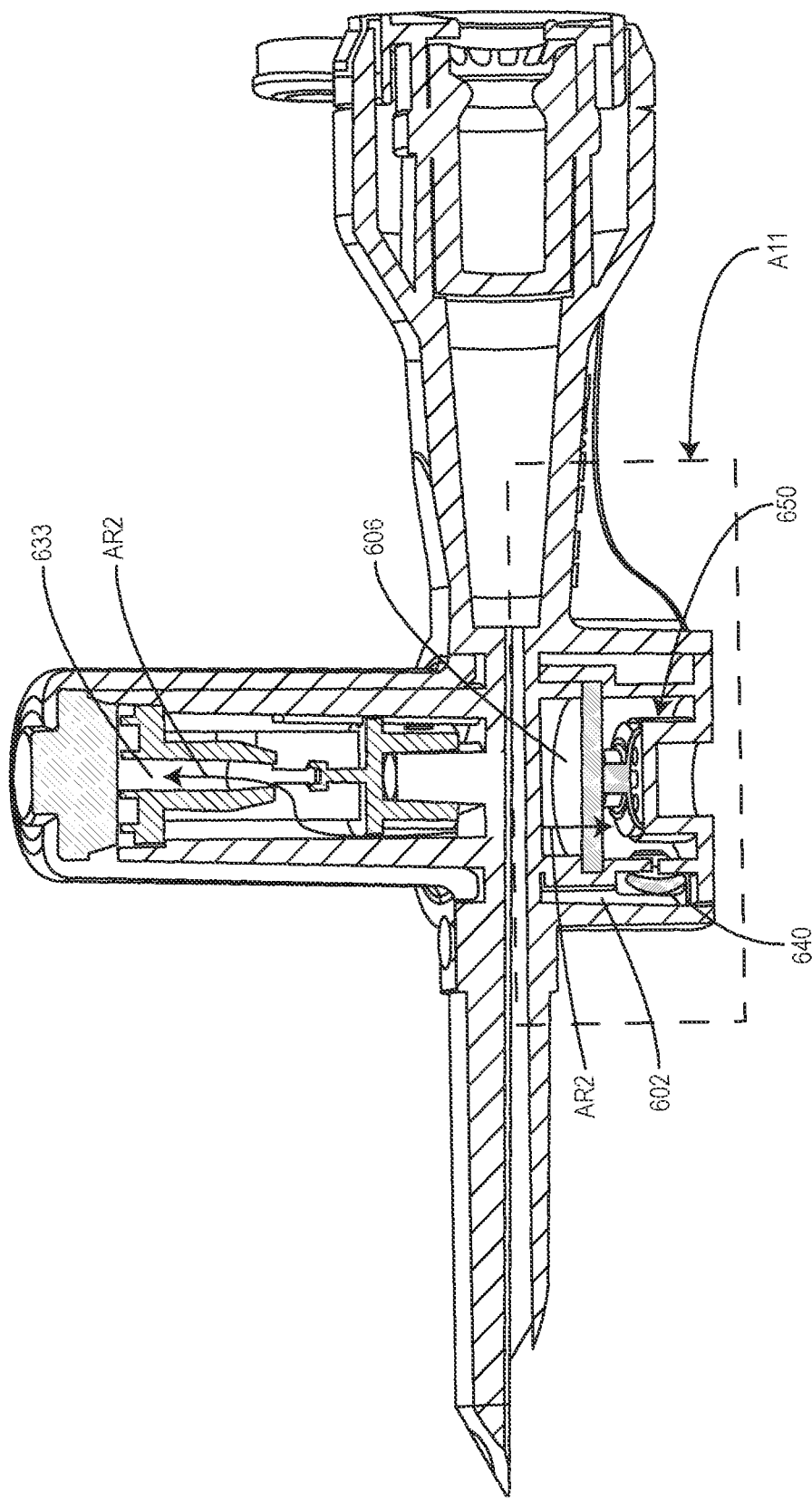
FIG. 9B is a cross-sectional view along line N-N in FIG. 9A.
Figure 9C:
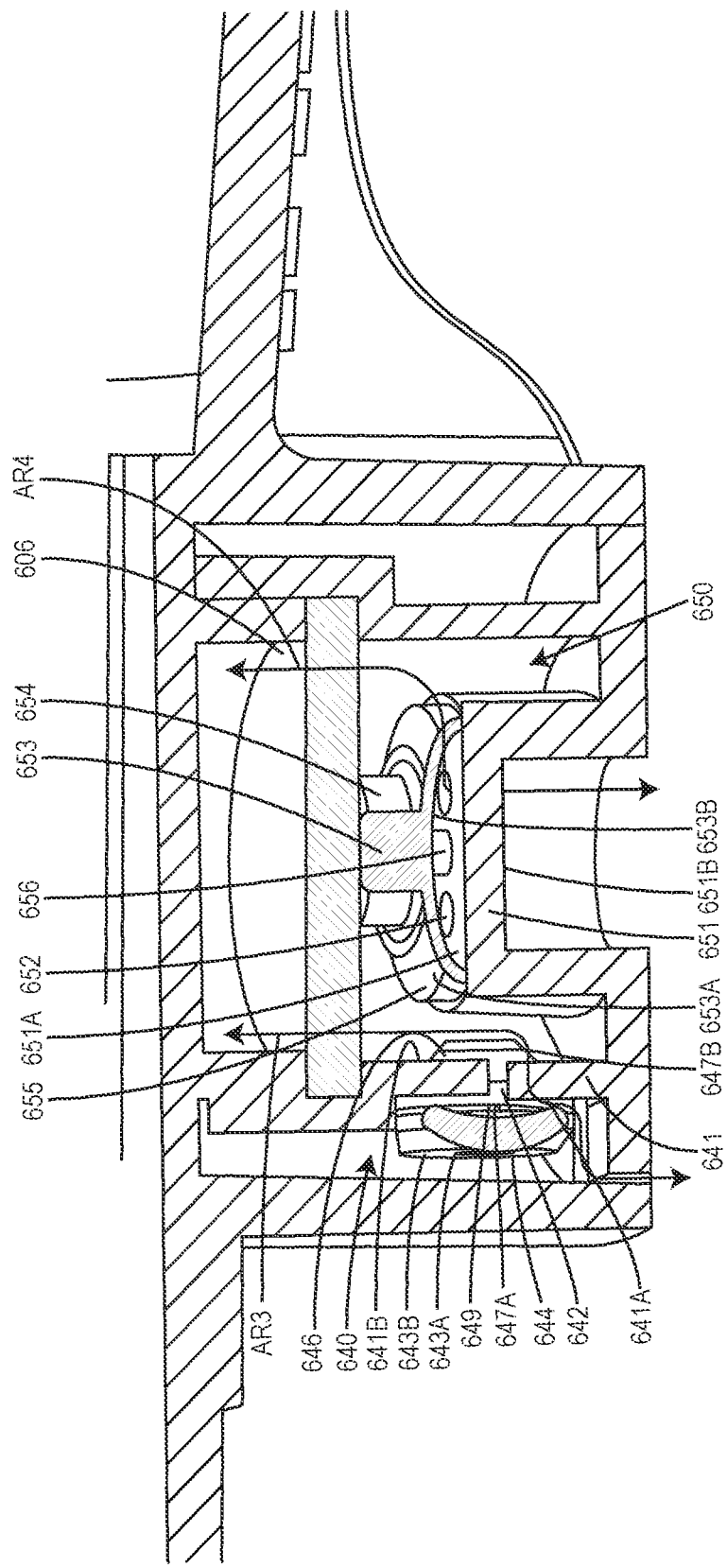
FIG. 9C is an enlarged view of section A11 of FIG. 9B.

Attention is now directed to FIGS. 9A-9C of the drawings illustrating the adaptor 600, more particularly illustrating the valves 640 and 650 for describing the control of air pressure within the adaptor 600, and consequently the syringe. The first valve 640 and the second valve 650, in the illustrated embodiment, are positioned within the body 601 and constitute a part of a common valve housing 602 constituting a fourth body portion of the body 601 of the adaptor 600. In some examples, the valves can be positioned in a separate valve housing that can be operationally articulated to the body 601. In the illustrated embodiment, the valve housing 602, and hence the valves are in fluid communication with the air channel 633 through the paths 635 (seen in FIG. 8B) and an air filter 606.

The first valve 640 comprises a first valve seating member 641, which in the illustrated example is a valve seat, defining a first valve passage 642 formed therein. The first valve seating member 641 has a first surface 641A and an opposite second surface 641B, and the first valve passage 642 extends between the first surface 641A and the second surface 641B. The adaptor 600 comprises a first fluid path, illustrated by arrow AR3, extending between the air channel 633 and the ambience through the first valve passage 642 and is selectively sealable by the first valve 640 at the first valve passage 642. The first valve 640 further comprises a first valve sealing member 643 having a central portion 644 and a skirt portion 645 extending radially outwards therefrom. The first valve sealing member 643 has a first surface 643A, and an opposite second surface 643B facing the first valve seating member 641. The first valve 640 further comprises a central member 647 extending from the central portion 644 and through the first valve passage 642, and having a first end 647A towards the central portion 644 and an opposite second end 647B. The central member 647 has flanges 646 extending from the second end 647B configured to engage the second surface 641B of the first valve seating member 641 thereby firmly holding the first valve sealing member 643 in place.

The first valve 640 is particularly in operation in association with a syringe that is used to withdraw the saline water from the IV bag through the adaptor 600. In some medical procedures, it is a protocol that only a new/unused syringe is to be used to withdraw the saline water from the IV bag, because a syringe that has already been used to handle hazardous drugs might have some harmful hazardous fumes in its air chamber that should be prevented from being released into the ambiance. Thus, as the operation of the first valve 640 is associated with the operation of the syringe that is used to withdraw the saline water from the IV bag, by controlling the operation of the first valve 650, the operation of the syringe can be controlled, as described later herein below.

The adaptor 600 further comprises the second valve 650 positioned within the housing 602. The second valve 650 comprises a second valve seating member 651, which in the illustrated example is a valve seat, defining a second valve passage 652. The second valve seating member 651 has a first surface 651A, and an opposite second surface 651B, and the second valve passage 652 extends between the first surface 651A and the second surface 651B.

The adaptor 600 comprises a second fluid path, illustrated by arrow AR4, extending between the air channel 633 and the ambience through the second valve passage 652 and is selectively sealable by the second valve 650 at the second valve passage 652. The second valve 650 further comprises a second valve sealing member 653 having a central portion 654 and a skirt portion 655 extending radially outwards therefrom. The second valve sealing member 653 has a first surface 653A, and an opposite second surface 653B facing the second valve seating member 651. The central portion 654 is connected to the second valve seating member 651 by a rigid central member 656 thereby holding the second valve sealing member 653 in place.

As can be seen in FIG. 9C, the first valve 640 is normally at its first valve normally closed state, and a rim 645A of the skirt portion 645 rests on the first surface 641A of the first valve seating member 641, thereby sealing the first valve passage 642, i.e., not allowing air flow between the air channel 633 and the ambiance. When an overpressure is created in the air channel 633, for example, when the syringe is used to extract a liquid into the syringe through the adaptor 600, the air pressure within the air channel 633 exerts force on the second surface 643B of the first valve sealing member 643 via the first valve passage 642. When the air pressure within the air channel 633 exceeds a first predetermined threshold (e.g., having a value of 0.3 bar), the force applied thereby on the second surface 643B causes the rim 645A of the skirt portion 645 to automatically lift up from the first surface 641A of the first valve seating member 641 thereby displacing the first valve 640 into its first valve open state and unsealing the first valve passage 642. At this first valve open state of the first valve 640, the air flows from the air channel 633 through the first valve passage 642 and escapes in the ambiance, illustrated by the arrow AR3, thereby releasing the overpressure from the air channel 633. When the air pressure being released from the air channel 633 falls below the first predetermined threshold, the rim 645A again returns to its original position thereby automatically displacing the first valve 640 into its first valve normally closed state. It is to be understood herein that the first predetermined threshold is generally greater than the ambient pressure for the air to flow from the air channel 627 into the ambiance. Further, the skirt portion 645 of the first valve sealing member 643 is a resilient member, whose resilience, along with its geometry and the parts surrounding it, is selected on the basis of the first predetermined threshold, which further depends on how much pressure is intended to be a maximum pressure that can be built within the air channel 633 before being released into the ambiance.

As further shown in FIG. 9C, the second valve 650 is normally at its second valve normally closed state, and a rim 655A of the skirt portion 655 rests on the first surface 651A of the second valve seating member 651, thereby sealing the second valve passage 652, i.e., not allowing air flow between the air channel 633 and the ambiance. The air pressure within the air channel 633 exerts force on the first surface 653A of the second valve sealing member 653 against the force applied by the ambient pressure on the second surface 653B of the second valve sealing member 653 through the second valve passage 652, thereby keeping the rim 655A engaged with the first surface 651A of the second valve seating member 651. When an underpressure is created in the air channel 633, for example, when the syringe is used to deliver a drug from the syringe through the adaptor 600, and the air pressure within the air channel 633 falls below a second predetermined threshold (e.g., having a value of 0.03 bar), the force applied by the ambient pressure on the second surface 653B of the second valve sealing member 653 activates the second valve 650, thereby causing the rim 655A of the skirt portion 655 to automatically lift up from the first surface 651A of the second valve seating member 651 thereby displacing the second valve 650 into its second valve open state and unsealing the second valve passage 652. At this second valve open state of the second valve 650, the air flows from the ambiance into the air channel 633 through the second valve passage 652, thereby balancing the underpressure created in the air channel 633. When the air pressure in the air channel 633 rises above the second predetermined threshold, the rim 655A returns to its original position thereby automatically displacing the second valve 650 into its second valve normally closed state.

The second valve is particularly in operation in association with a syringe that is used to deliver the drug into the IV bag through the adaptor.

It is to be understood herein that the second predetermined threshold is generally lesser than the ambient pressure for the air to flow from the ambiance into the air channel 633. Further, the skirt portion 655 of the second valve sealing member 653 is a resilient member, whose resilience, along with its geometry and the parts surrounding it, is selected on the basis of the second predetermined threshold, which further depends on how much pressure is intended to be a minimum pressure that can be allowed within the air channel 633 before being balanced from the ambiance.

It is to be understood herein that when the pressure within the air channel 633 is between the first predetermined threshold and the second threshold pressure, both the first valve 640 and the second valve 650 are in their respective closed states. In particular, when the pressure within the air channel 633 is equal to the ambient pressure, both the first valve 640 and the second valve 650 are in their respective closed states.

It is to be further understood herein that at the first valve open state, the second valve 650 remains in its second valve normally closed state, and at the second valve open state, the first valve 640 remains at its first valve normally closed state.

Attention is now directed to FIGS. 10A-10D of the drawings illustrating an adaptor 600' according to another example of the presently disclosed subject matter, configured for connection to the syringe 500. The adaptor 600' has at least some of the elements corresponding to those of the adaptor 600 as described above, and have been depicted by corresponding reference numerals for ease of understanding. Alternative to the first valve 640 and the second valve 650 as of the adaptor 600, the adaptor 600' comprises a valve arrangement 660 in fluid communication with the ambiance. The valve arrangement 660 is a dual function valve configured to perform the functioning of both of the first valve 640 and the second valve 650. For instance, the adaptor 600' is configured to solve the problem of overpressure and underpressure in the syringe 500, in that, the valve arrangement 660 is configured to facilitate escape of air from within the adaptor 600' to the ambiance in case of overpressure, and to facilitate entry of air from the ambiance into the adaptor 600' in case of underpressure.

The valve arrangement 660 comprises a first valve seating member 661, which in the illustrated example, is a central member 661, and a second valve seating member 671, which in the illustrated example, is a valve seat 671 having a seat opening 672. The central member 661 extends through the seat opening 672. In the illustrated example, the central member 661 extends from a bottom 604' of the valve housing 602'. In some examples, the central member 661 can extend from a bottom portion 631A' of the fluid transfer device 631', through an air filter 606'. The valve arrangement 660 further comprises a sealing member 663 including a longitudinal member 664 having a first end 664A and an opposite second end 664B. The sealing member 663 further comprises a sealing member first portion 665 extending radially from the first end 664A of the longitudinal member 664 towards the central member 661, and being configured to selectively engage and disengage the central member 661. The sealing member first portion 665 and the central member 661 define therebetween a first valve passage 662. The sealing member 663 further comprises a sealing member second portion 666 extending radially from the first end 664A of the longitudinal member 664 towards the valve seat 671, and being configured to selectively engage and disengage the valve seat 671. The sealing member second portion 666 and the valve seat 671 define therebetween a second valve passage 672.

The valve seat 671 has a valve seat internal surface 671A facing the air channel 633, and an opposite valve seat external surface 671B. The sealing member second portion 666 engages, and selectively disengages, the valve seat internal surface 671A. The sealing member 663 further comprises a sealing member third portion 667, which in the illustrated example is configured as a fixing member 667 extending radially from the second end 664B of the longitudinal member 664 towards the valve seat 671, and configured to engage the external surface 671B of the valve seat 671, without blocking the second valve passage 672, thereby holding the sealing member 663 in its position. The sealing member second portion 666 and the fixing member 667 holds the sealing member 663 in its position relative to the valve seat 671. For instance, when the sealing member second portion 666 disengages the valve seat 671, the fixing member 667 engaging the valve seat external surface 671B prevents axial displacement of the sealing member 663.

In the valve arrangement 660, the coordination of the central member 661 and the sealing member first portion 665 acts as the first valve, and the coordination between the valve seat 671 and the sealing member second portions 666 acts as the second valve.

Figure 10A:
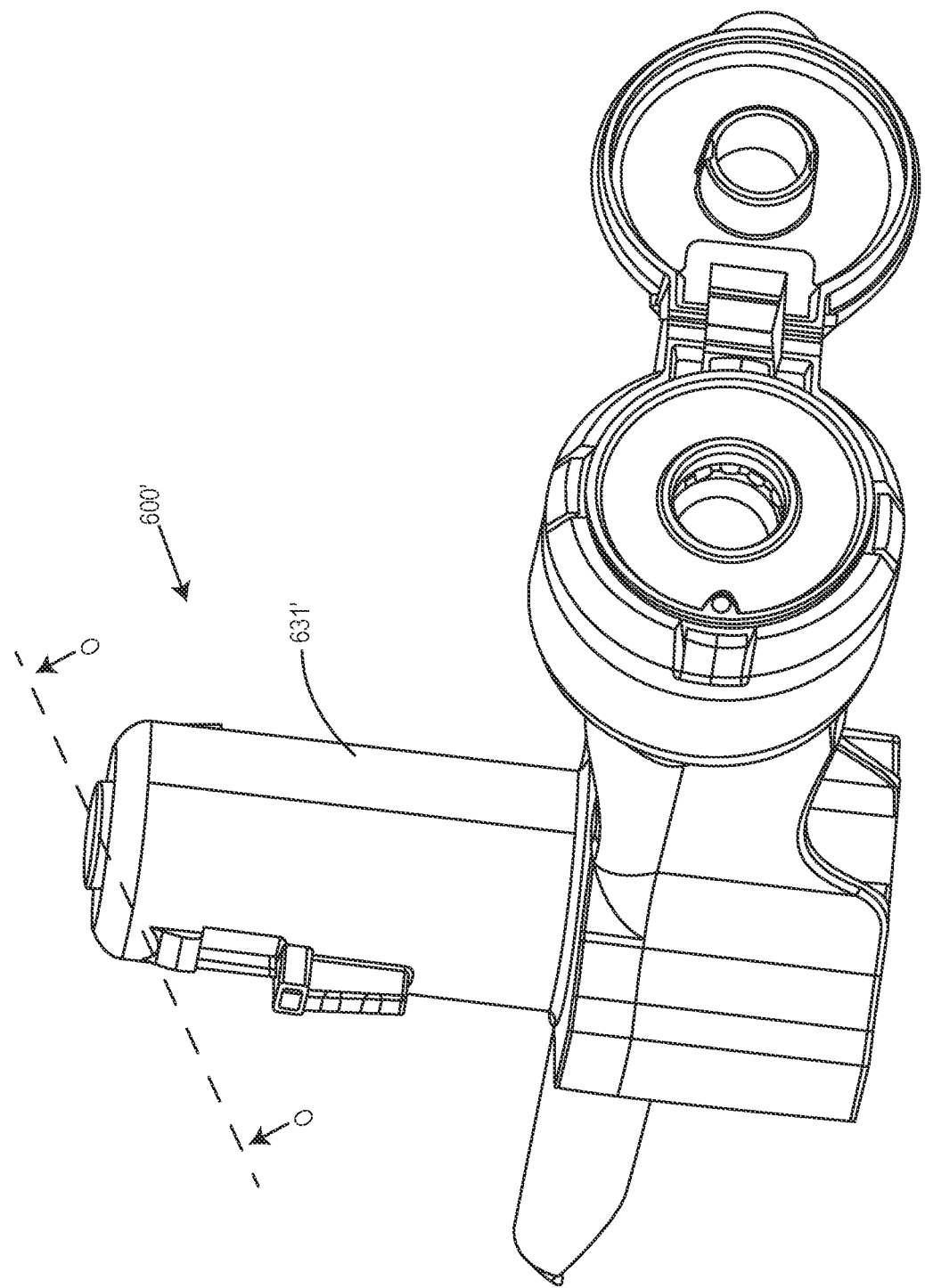
FIG. 10A is a back perspective view of an adaptor according to a fifth example of the presently disclosed subject matter.
Figure 10B:
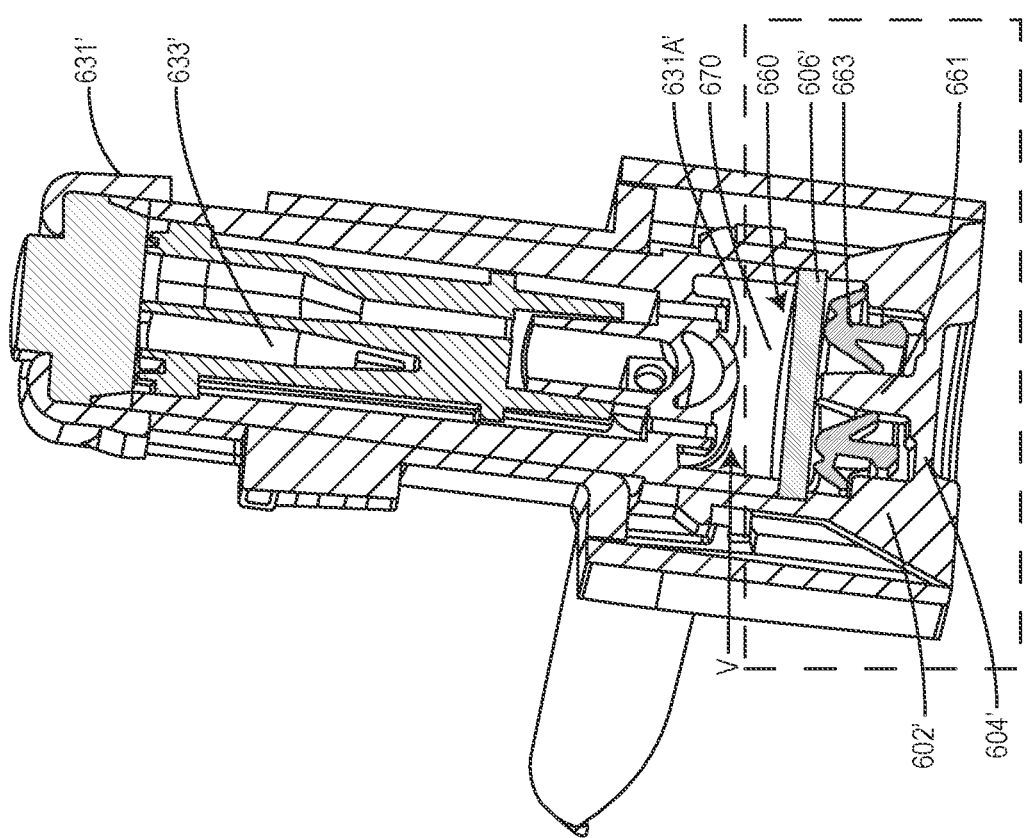
FIG. 10B is a cross-sectional view along line O-O in FIG. 10A.
Figure 10C:
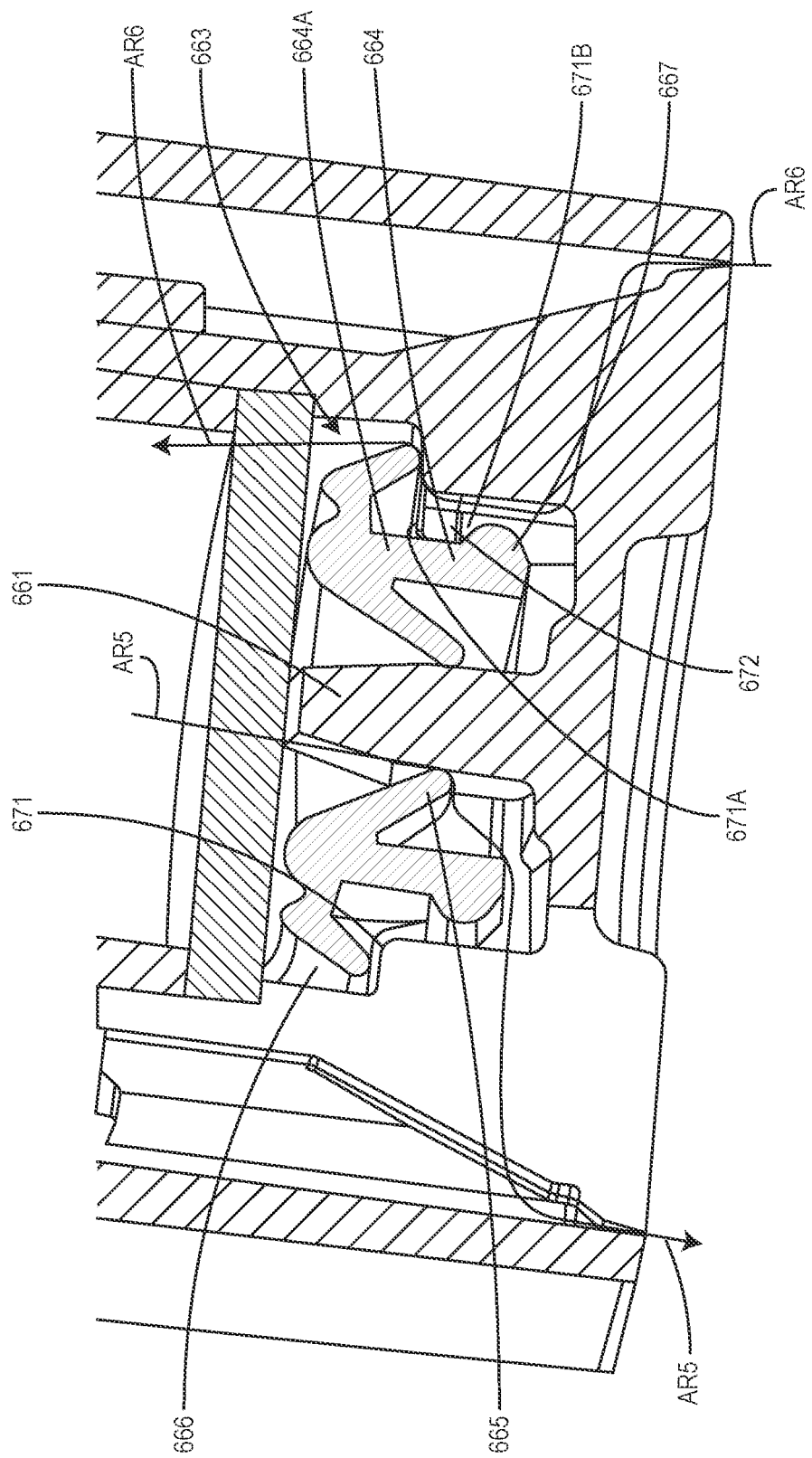
FIG. 10C is an enlarged view of section A12 of FIG. 10B.
Figure 10D:
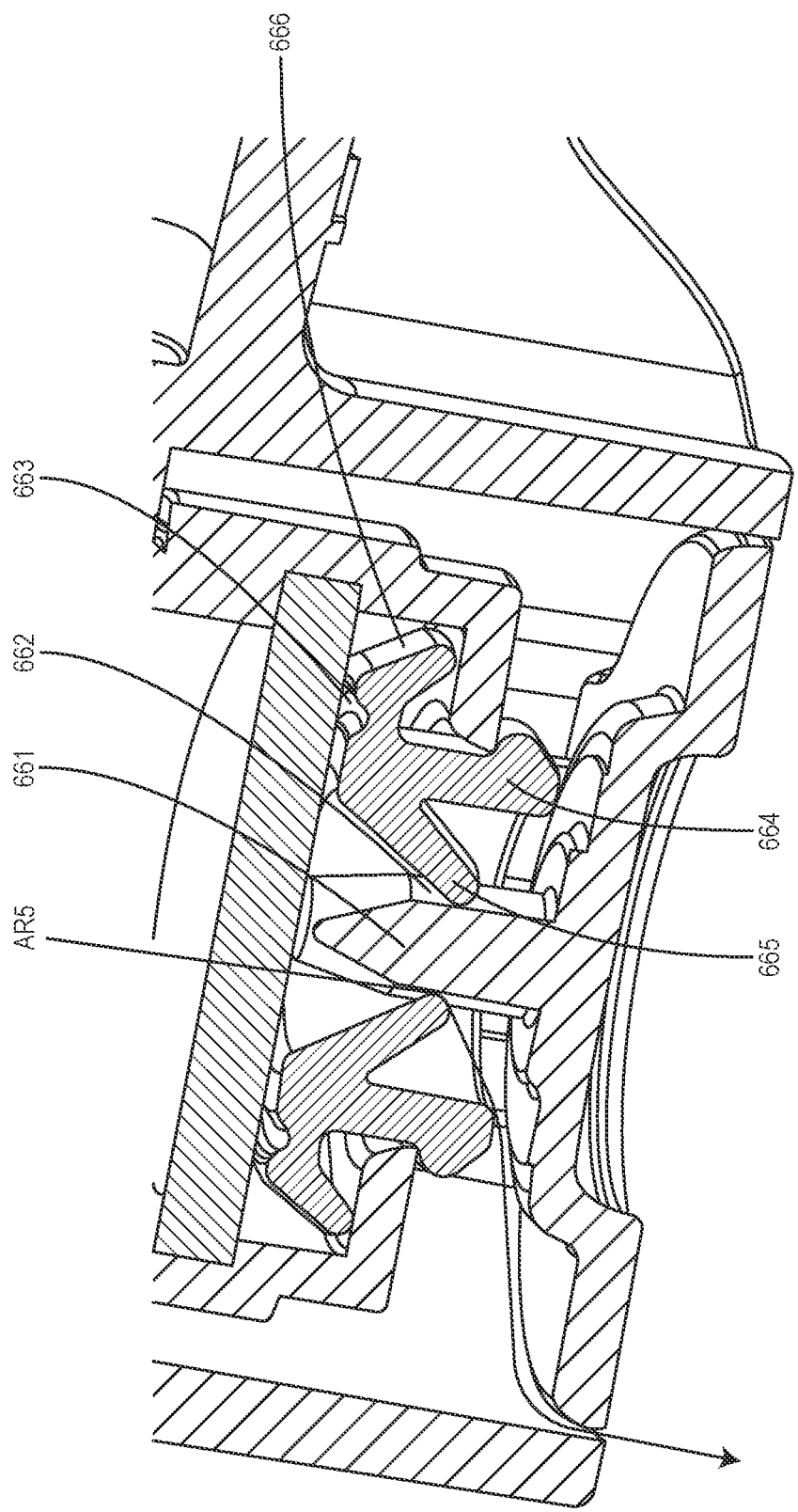
FIG. 10D is another cross-sectional view of the portion shown in FIG. 10C but with the cross section taken along a line perpendicular to the line O-O.

As can be seen in FIGS. 10C and 10D, the valve arrangement 660 is normally at its normal fully closed state. The sealing member first portion 665 engages with the central member 661, thereby sealing the first valve passage 662. Also, the sealing member second portion 666 engages with the first surface 671A of the valve seat 671, thereby sealing the second valve passage 672. At this normal fully closed state, the volume V defined between the sealing member 663, a portion 671' of the valve seat 671 not covered by the sealing member second portion, bottom portion 631'A of the fluid transfer device 631', and the sidewall 670 defines the volume within the valve arrangement 660.

When an overpressure is created in the air channel 633' and consequently in the volume V, the air pressure within the valve arrangement exerts force on the sealing member first portion 665. When the air pressure within the valve arrangement exceeds a first predetermined threshold, the force applied thereby on the sealing member first portion 665 causes the sealing member first portion 665 to flex away from the central member 661, thereby causing the sealing member first portion 665 to disengage from the central member 661, thereby unsealing the first valve passage 662 and automatically displacing the valve arrangement 660 into its first valve open state. At this first valve open state, the air flows from the air channel 633/volume V through the first valve passage 662 and escapes into the ambiance, the flow depicted by arrows AR5 in FIG. 10D. This releases the overpressure from the valve arrangement 660. When the air pressure being released from the valve arrangement 660 falls below the first predetermined threshold, the sealing member first portion 665 flexes back to its normal position thereby automatically displacing the valve arrangement 660 into its normal fully closed state. It is to be understood herein that the first predetermined threshold is generally greater than the ambient pressure for the air to flow from the valve arrangement 660 into the ambiance, and is selected based on how much pressure is intended to be a maximum pressure that can be built within the valve arrangement 660 before being released into the ambiance.

At the normal fully closed state of the valve arrangement 660, the air pressure within the volume V of the valve arrangement 660, or the air channel 633, exerts force on the sealing member second portion 666 against the force applied by the ambient pressure on the sealing member second portion 666 via the second valve passage 672, thereby keeping the sealing member second portion 666 engaged with the first surface 671A of the valve seat 671.

When an underpressure is created in the air channel 633' and consequently in the volume V, the force applied by the air pressure within the valve arrangement 660 on the sealing member second portion 666 decreases. When the air pressure within the valve arrangement 660 falls below a second predetermined threshold, the sealing member second portion 666 automatically lifts up from the first surface 671A of the second valve seating member 671, thereby displacing the valve arrangement 60 into its second valve open state and unsealing the second valve passage 672. At this second valve open state, the air enters from the ambiance into the volume V via the second valve passage 672, as depicted by arrow AR6 in FIG. 10C, thereby balancing the underpressure created in the valve arrangement 660. When the air pressure in the valve arrangement 660 rises above the second predetermined threshold, the sealing member second portion 666 returns to its original position thereby automatically displacing the valve arrangement 660 into its normal fully closed state. It is to be understood herein that the second predetermined threshold is lesser than the ambient pressure for the air to flow from the ambiance into the valve arrangement 660, and is selected based on how much pressure is intended to be a minimum pressure that can be allowed within the valve arrangement 660 before being balanced from the ambiance.

It is to be understood herein that when the pressure within the valve arrangement 660 is between the first predetermined threshold and the second threshold pressure, the valve arrangement 660 is in its fully closed state. In particular, when the pressure within the valve arrangement 660 is equal to the ambient pressure, the valve arrangement 660 is in its fully closed state.

It is to be further understood that the resilience of the sealing member first and second portions is selected based on the first predetermined threshold and the second predetermined threshold. It is to be further understood herein that at the first valve open state of the valve arrangement 660, the sealing member second portion 666 seals the second valve passage 772, and at the second valve open state, the sealing member first portion 665 seals the first valve passage 662.

The valve arrangement 660 as described above can be used with any fluid transfer apparatus that requires an air pressure to be maintained within a range. Also, the valve arrangement 660 as described above can be used with the adaptor 600 as described above with reference to FIGS. 8A to 9C, wherein the first valve 640 and second valve 650 can be realized as the valve arrangement 660, with the sealing members 643 and 653 being configured as a single common sealing member, such as sealing member 663.

It should be understood herein that the application of the dual function valve 660 is advantageous over application of two valves 640 and 650, in that, a single sealing member needs to be manufactured and assembled instead of two separate sealing members. Further, the single valve arrangement occupies lesser space than the two separate valves within the housing of the adaptor.

Attention is now directed to FIGS. 11A to 11D of the drawings illustrating a cross-sectional view of a portion of an adaptor 700 according to another example of the presently disclosed subject matter, for the purposes of describing the selective usage of the adaptor 700 in its fully operational and at least partial inoperational state. The adaptor 700 is similar in structure and operation to the adaptor 600' described above and incorporates at least some of the features of the adaptor 600' which have been designated by corresponding reference numerals for the adaptor 700.

The adaptor 700 has a valve arrangement 760 similar in structure and operation to the valve arrangement 660 as described above, with one difference being that a central member 761 extends from the bottom portion 731A of the fluid transfer device 731. In addition to the features of the adaptor 600'; the adaptor 700 includes an actuator 780, with FIGS. 11B and 11D showing a front view of the actuator 780. The actuator 780 is configured to switch the adaptor 700 between its fully operational state and at least partial inoperational state.

As also described above, the adaptor, being a spike adaptor in the illustrated example, is configured to facilitate transfer of liquid between an IV bag and a syringe in two directions via the liquid channel 734. The spike adaptor can be used to inject the liquid from within the syringe into the IV bag and to withdraw the liquid from the IV bag into the syringe through the liquid channel 734. During said transfer of the liquid, the air pressure within the air chamber of the syringe, and consequently in the air channel 733 of the adaptor 700 varies based on whether a plunger of the syringe is pulled or pushed. The spike adaptor is configured to facilitate the discharge and intake of air from and into the air channel, and consequently to the air chamber, via the valve arrangement 760. In the present application, the term fully operational state has been referred to as a state in which the spike adaptor is configured to facilitate transfer of liquid in both the directions, i.e., from the IV bag into the syringe and vice versa through the liquid channel 734, and the term at least partial inoperational state has been referred to as a state in which the spike adaptor is configured to block transfer of liquid in at least one of the two directions, which in the illustrated example is from the syringe into the IV bag and preventing the transfer of liquid in the opposite direction, i.e., from the IV bag into the syringe through the liquid channel 734.

As described above, the protocol can require a medical practitioner to use a new/unused syringe for withdrawing the saline water from the IV bag through the adaptor 700. The adaptor is configured to be selectively at its at least partial operational state so as to act as a reminder for the practitioner that a new syringe needs to be used for withdrawing the saline water from the IV bag. For instance, the adaptor 700 is configured to be normally at its at least partial inoperational state at which the flow of the liquid through the adaptor in the direction from the IV bag to the syringe is blocked. Thus, when the practitioner would want to use the adaptor for the purpose of withdrawing the saline water from the IV bag into the syringe, the adaptor would be required to be manually switched into its fully operational state by the practitioner using the actuator, thereby preventing the practitioner to accidentally and carelessly use an already used syringe for the purpose, and reminding the practitioner that as the adaptor is switched to its fully operational state, a new syringe is to be used.

In the illustrated example, at the at least partial inoperational state, the actuator 780 is configured to partially block the transfer of liquid through the liquid channel 734, i.e., in one direction, indirectly by controlling the passage of air between the ambiance and the air channel 733. As described above as well, the flow of liquid depends upon the discharge and intake of air from and into the air chamber of the syringe via the air channel 733. For instance, if the pressure is not discharged from the air chamber of the syringe, the syringe cannot be operated to extract a liquid into the syringe through the adaptor 700, in that, the air pressure in the air chamber of the syringe prevents the movement of the plunger of the syringe towards the air chamber, thereby rendering the syringe inoperable to extract the liquid into the syringe when the air pressure is not discharged. Thus, by controlling the passage of air through the air channel, the transfer of liquid can be indirectly controlled.

Figure 11A:
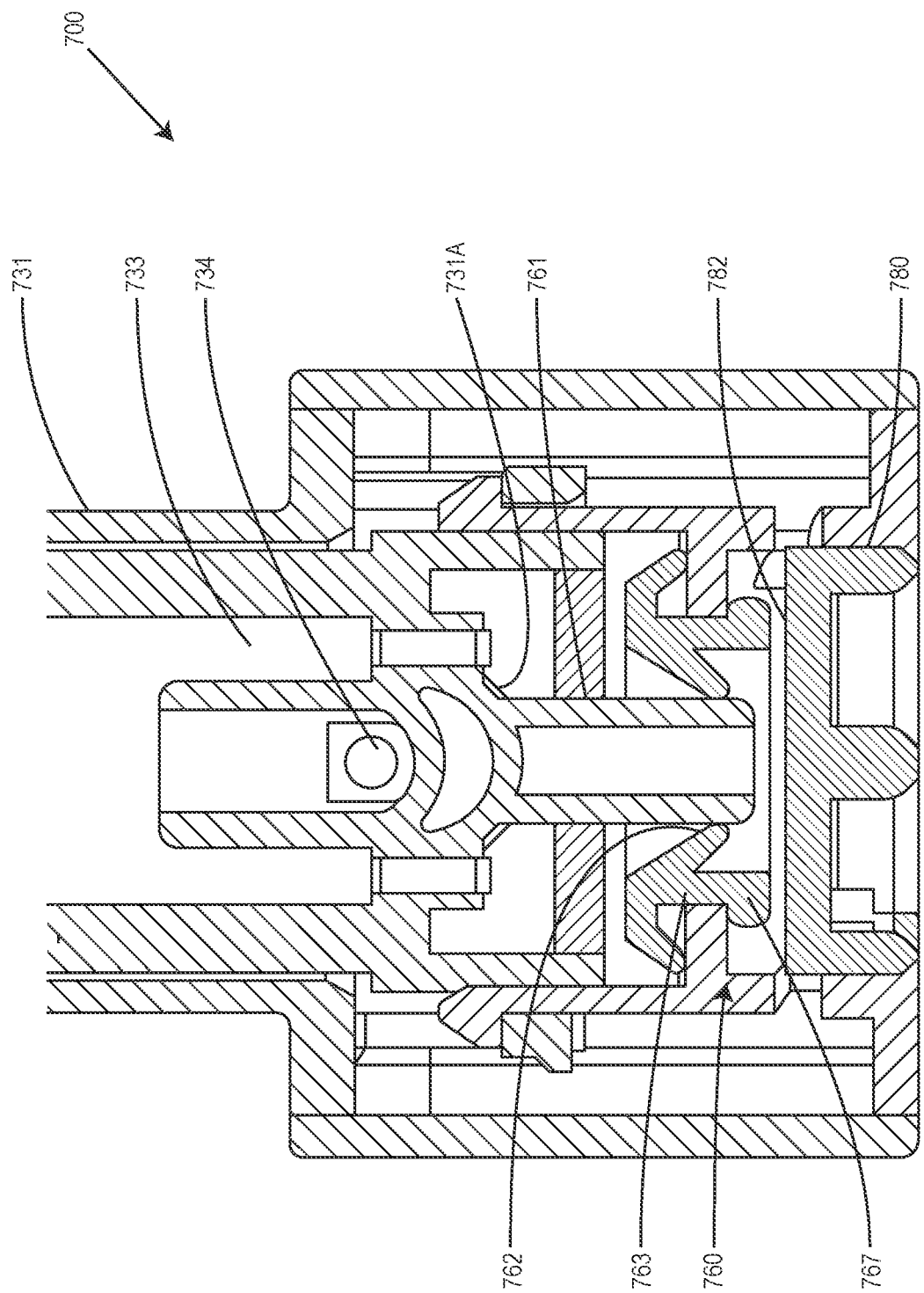
FIG. 11A is a cross-sectional view of an adaptor according to a sixth example of the presently disclosed subject matter, illustrating its valve arrangement and an actuator in its first actuator state.
Figure 11B:
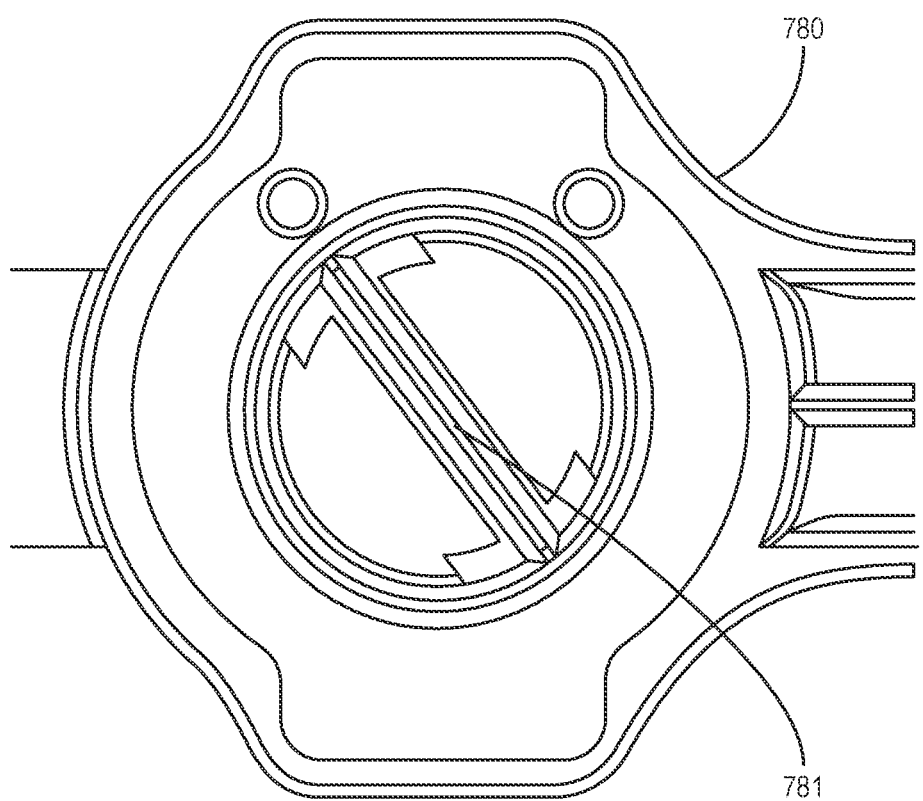
FIG. 11B is a front view of the actuator of FIG. 11A.
Figure 11C:
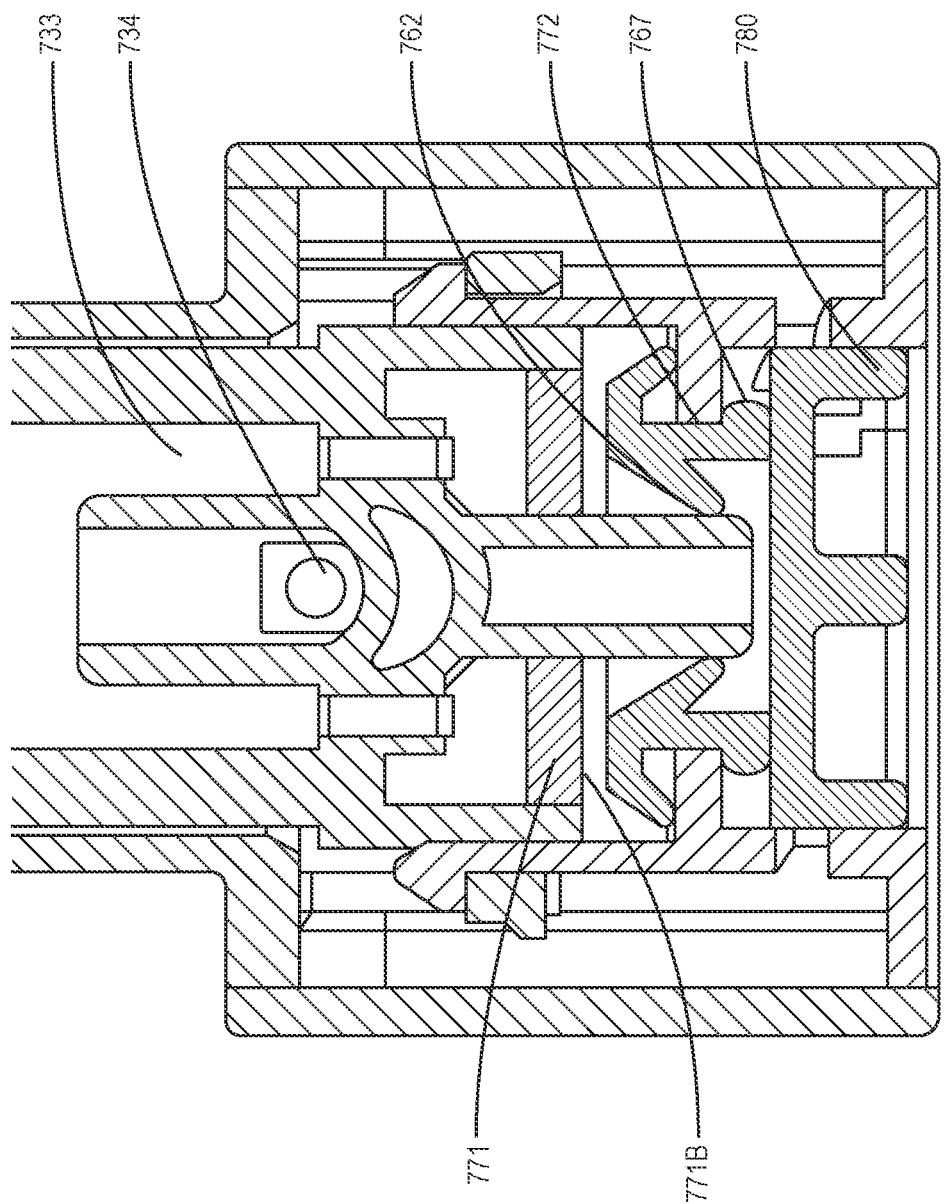
FIG. 11C is the same view as that of FIG. 11A illustrating the actuator in its second actuator state.
Figure 11D:
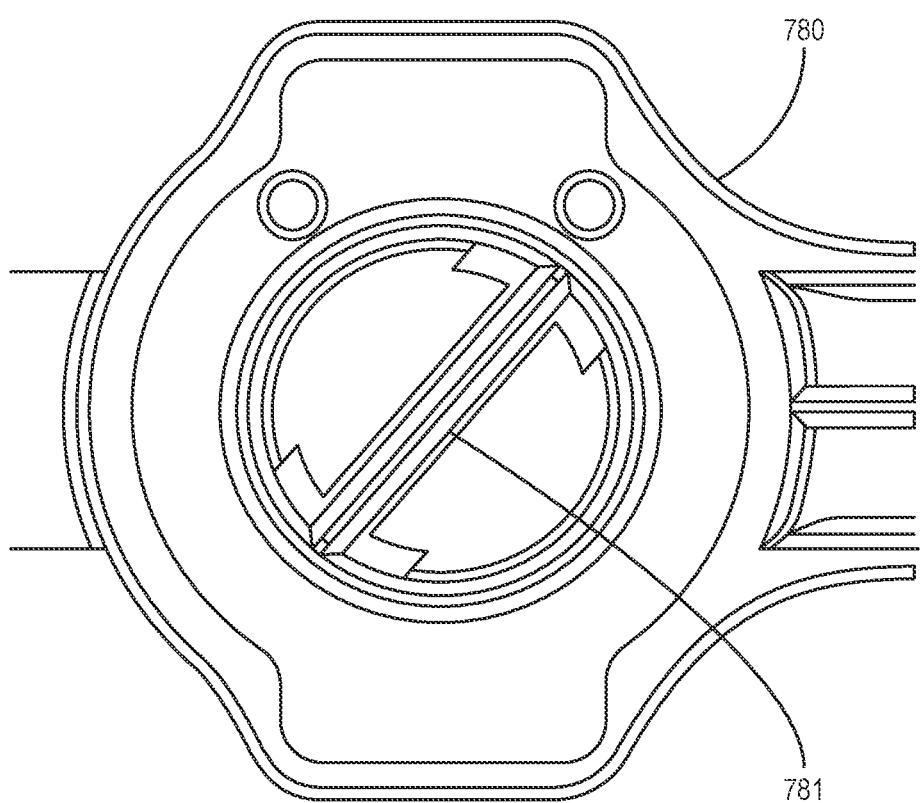
FIG. 11D is a front view of the actuator of FIG. 11C.

In the illustrated example, the actuator 780 is configured as a switch 780, which is configured to displace between a first actuator state, as shown in FIG. 11A, and a second actuator state, as shown in FIG. 11B. The switch 780 has a knob 781 configured to be held by a user to rotate the switch, in the illustrated example, to displace between first actuator state and the second actuator state. In some examples (not shown), the actuator can be displaced between the two actuator states by any other movement than rotation, for example by pushing/pulling. The switch 780 has an actuator internal surface 782 configured to engage the sealing member third portion 767 of the sealing member 763, at the actuator second state, as can be seen in FIG. 11B.

When the actuator is at its actuator first state, in FIG. 11A, the valve arrangement 760 facilitates the discharge as well as intake of air though the valve arrangement 760 between the air channel 733 and the ambiance, as described above with reference to FIGS. 10A to 10D. Thus, the actuator first state is associated with the fully operational state of the adaptor 700.

When the actuator is at its actuator second state, in FIG. 11B, the valve arrangement 760 is configured to facilitate intake of air through the second valve passage 772, however, as can be seen in FIG. 11B, the actuator internal surface 782 engages the sealing member third portion 767 so as to seal the discharge of air through the first valve passage 762. At this actuator second state, the discharge of the air from the air channel 733 and consequently from the air chamber of the syringe is prevented, thus, the syringe and hence the adaptor is inoperable, as described above, for transfer of the liquid in the direction from the IV bag into the syringe, i.e., from the spike terminal portion towards the fluid transfer device. Thus, the actuator second state is associated with the at least partial inoperational state of the adaptor 700.

The actuator 780, at its actuator second state engages the sealing member third portion 767 with the sealing member third portion being tightly engaged between the switch 780 and the second surface 771B of the valve seat 771. The valve arrangement 760 can still be displaced into the first valve open state but that would not discharge the air from the air channel, in that the air is prevented from escaping by the tight engagement between the sealing member third portion and the actuator 780. Thus, the actuator 780, at its second actuator state, is configured to prevent the discharge of the air irrespective of the state of the valve arrangement 760.

The actuator/switch 780 is configured to be normally at its actuator first state, shown in FIG. 11A, and is configured to be displaced into its actuator second state upon application of a force by a user, in the illustrated example, for rotating the switch 780. The switch 780 is configured to remain in its actuator second state upon removal of the force. The switch 780 can then be displaced to its first actuator state by rotating it in a reverse direction.

Figure 12A:
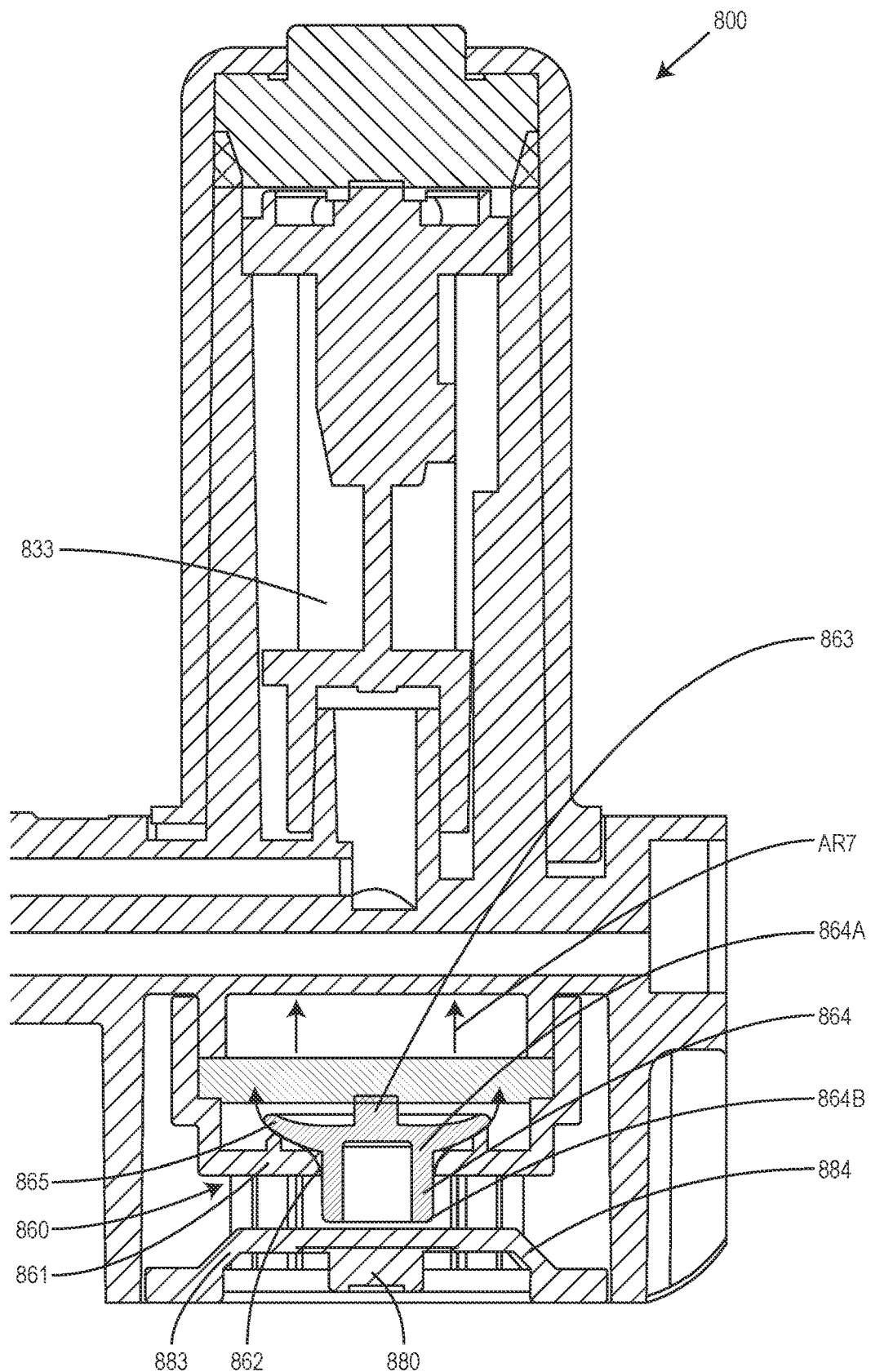
FIG. 12A is a cross-sectional view of an adaptor according to a seventh example of the presently disclosed subject matter, illustrating its valve arrangement and an actuator in its second actuator state.
Figure 12B:
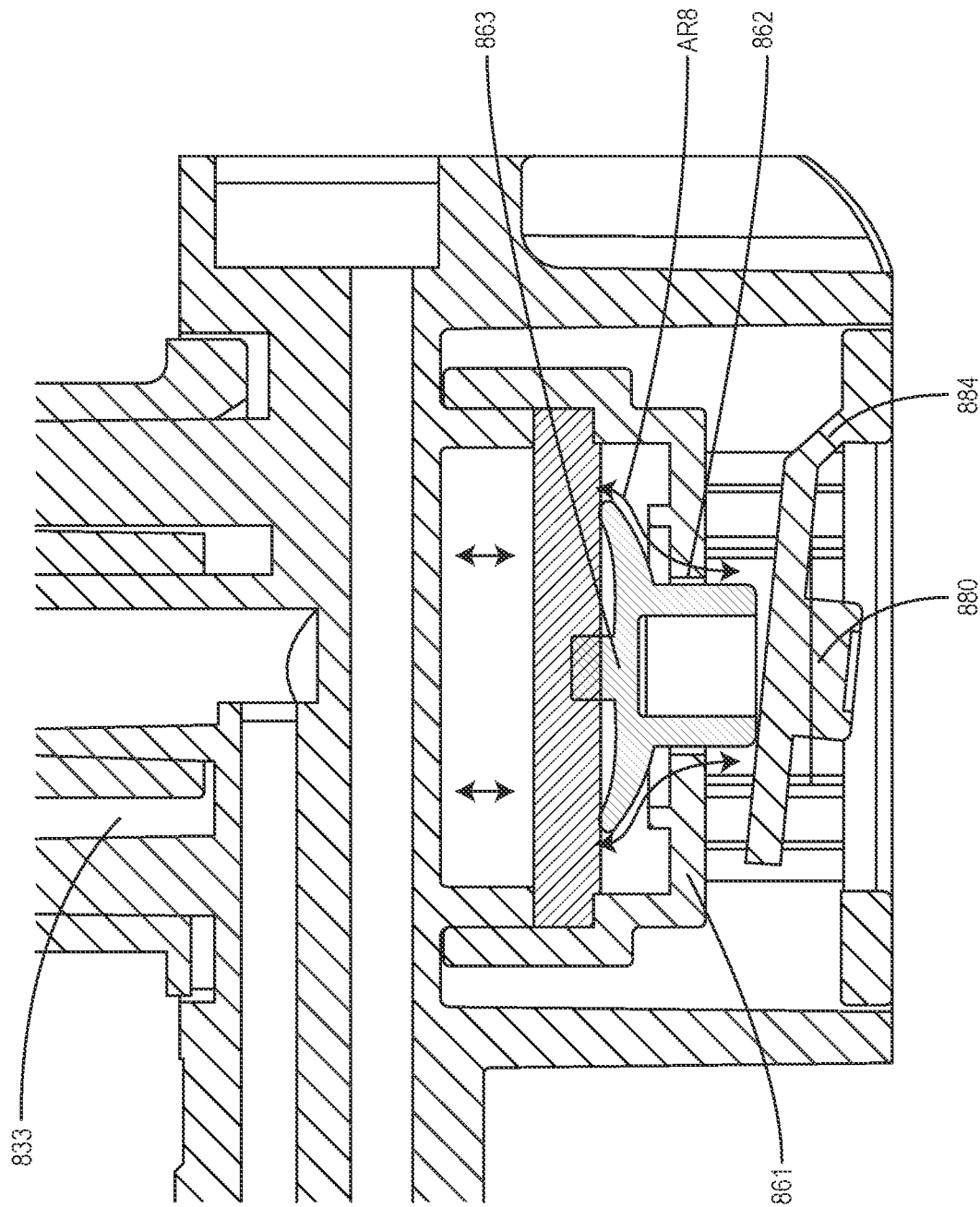
FIG. 12B is the same view as that of FIG. 12A illustrating the actuator in its first actuator state.

Attention is now directed to FIGS. 12A and 12B of the drawings illustrating a cross-sectional view of a portion of an adaptor 800 according to another example of the presently disclosed subject matter, for the purposes of describing the selective usage of the adaptor 800 in its fully operational and at least partial inoperational state. The adaptor 800 is similar in structure and operation to the adaptor 600' and/or 700 described above and incorporates at least some of the features of the adaptor 600' and/or 700 which have been designated by corresponding reference numerals for the adaptor 800. The major difference between the adaptor 800 from the adaptor 600' being in the structure of the valve arrangement, and the major difference between the adaptor 800 from the adaptor 700 being in the structure of the valve arrangement and the actuator. Apart form these, the adaptor 800 operates, specifically related to the transfer of liquid and air, in the similar manner as to the adaptors 600' and 700.

The adaptor 800 has a valve arrangement 860 having a seating member 861 defining a valve passage 862 configured to allow flow of air (intake as well as discharge) therethrough between the ambiance and the air channel 833 of the adaptor 800. The valve arrangement 860 further comprises a sealing member 863 including a central portion 864 extending through the valve passage 862 and having a first end 864A and an opposite second end 864B. The sealing member 863 has a skirt portion 865 extending radially outwards from the first end 864A of the central member 864, and configured to selectively engage the seating member 761 thereby sealing the valve passage 862.

The valve arrangement 860 is configured to be at its normally closed state, in which the skirt portion 865 engages the seating member 861 and seals the valve passage 862. When an underpressure is created in the air channel 833, and the pressure within the air channel falls below a predetermined threshold, a force exerted by the air pressure within the air channel on the skirt portion 865 becomes lesser than a force exerted by the ambient pressure on the skirt portion 865 via the valve passage 862, thereby resulting in lifting up and disengagement of the skirt portion 865 from the seating member 861 thereby unsealing the valve passage 862 and displacing the valve arrangement into its open state. The air from the ambiance can thus flow through the valve passage 862 into the air channel 833, as illustrated by arrow AR7, and subsequently into the air chamber of the syringe. However, when an overpressure is created in the air channel 833, the air pressure is not discharged through the valve passage 862, as the air pressure would not disengage the skirt portion 865 from the seating member 861.

The adaptor 800 further comprises an actuator 880 configured to be displaced between a first actuator state, as shown in FIG. 12B, and a second actuator state, as shown in FIG. 12A. In the illustrated example, the actuator 880 is a button configured to be pressed for displacing the same from its normal second actuator state (FIG. 12A) to its first actuator state (FIG. 12B). As can be seen in FIG. 12A, when the actuator is in its second actuator state, the intake of the air into the adaptor is allowed while the discharge of the air is prevented, thereby rendering the syringe and the adaptor 800 inoperable for transfer of the liquid in the direction from the IV bag to the syringe, as described above with reference to the adaptor 700. Thus, the second actuator state of the actuator is associated with the at least partial inoperational state of the actuator.

When the actuator 880 is in its first actuator state, as shown in FIG. 12B, the actuator 880 engages the second end 864B of the central member 864 of the sealing member 863 and lifts the central member 864 and consequently lifting the skirt portion 865 from the seating member 861 thereby unsealing the valve passage 862. At this state of the actuator, the air can flow into and/or out of the adaptor 800 via the valve passage 862, illustrated by arrows AR8, thereby rendering the adaptor usable for transfer of liquid through its liquid channel in both the directions as described above with reference to adaptor 700. Thus, the first actuator state is associated with the fully operational state of the adaptor 800.

In the valve arrangement 860, when the air is discharged through the valve passage 862, the valve arrangement acts as a first valve and when the air enters from the ambience into the adaptor, the valve arrangement acts as a second valve.

In the illustrated example, the actuator comprises a breakable tab 883 configured to prevent the actuator from being displaced into its first actuator state from its normal second actuator state. When the actuator is required to be displaced into its first actuator state, a user can exert a pushing force onto the button 880 thereby breaking the breaking tab 883 and pushing the button 880 into its first actuator state. As can be seen in FIG. 12B, the actuator further comprises a hinge 884 configured to facilitate pivoting of the button 880 thereabout to be displaced between its first actuator state and second actuator state. In the illustrated example, the button is configured to return automatically into its second actuator state upon removal of the pushing force. Thus, when the fully operational state of the adaptor is intended, the user has to push the button 880 until the desired fully operational state is intended, and then release the button when the at least partial inoperational state of the adaptor is intended.

In the examples illustrated herein, the actuator has been described as constituting a part of the adaptors 700 and 800, however, it is to be understood herein that, in some examples (not shown), the actuators can constitute a part of the valve arrangement and can be disposed within or constitute a part of the valve housing.

Attention is now directed to FIGS. 13A to 13D of the drawings illustrating an adaptor 900 according to another example of the presently disclosed subject matter, for the purposes of describing the actuator being configured to directly block the flow of liquid through the adaptor by blocking a liquid channel of the adaptor directly.

The adaptor 900, in the illustrated example, is a luer lock adaptor configured to facilitate transfer of liquids between a syringe and an external container through a liquid channel 926. A syringe (not shown) can be connected to the adaptor 900 while inserting a liquid needle of the syringe through a septum 930 of the adaptor 900. An external container (not shown) can be connected to a luer lock connector 910 of the adaptor 900. The luer lock connector 910 is similar in construction and operation to that of the luer lock connector 10 described above. The adaptor 900 has a valve arrangement 920 configured to facilitate flow of air between the ambiance and an interior of the adaptor 900.

Figure 13A:
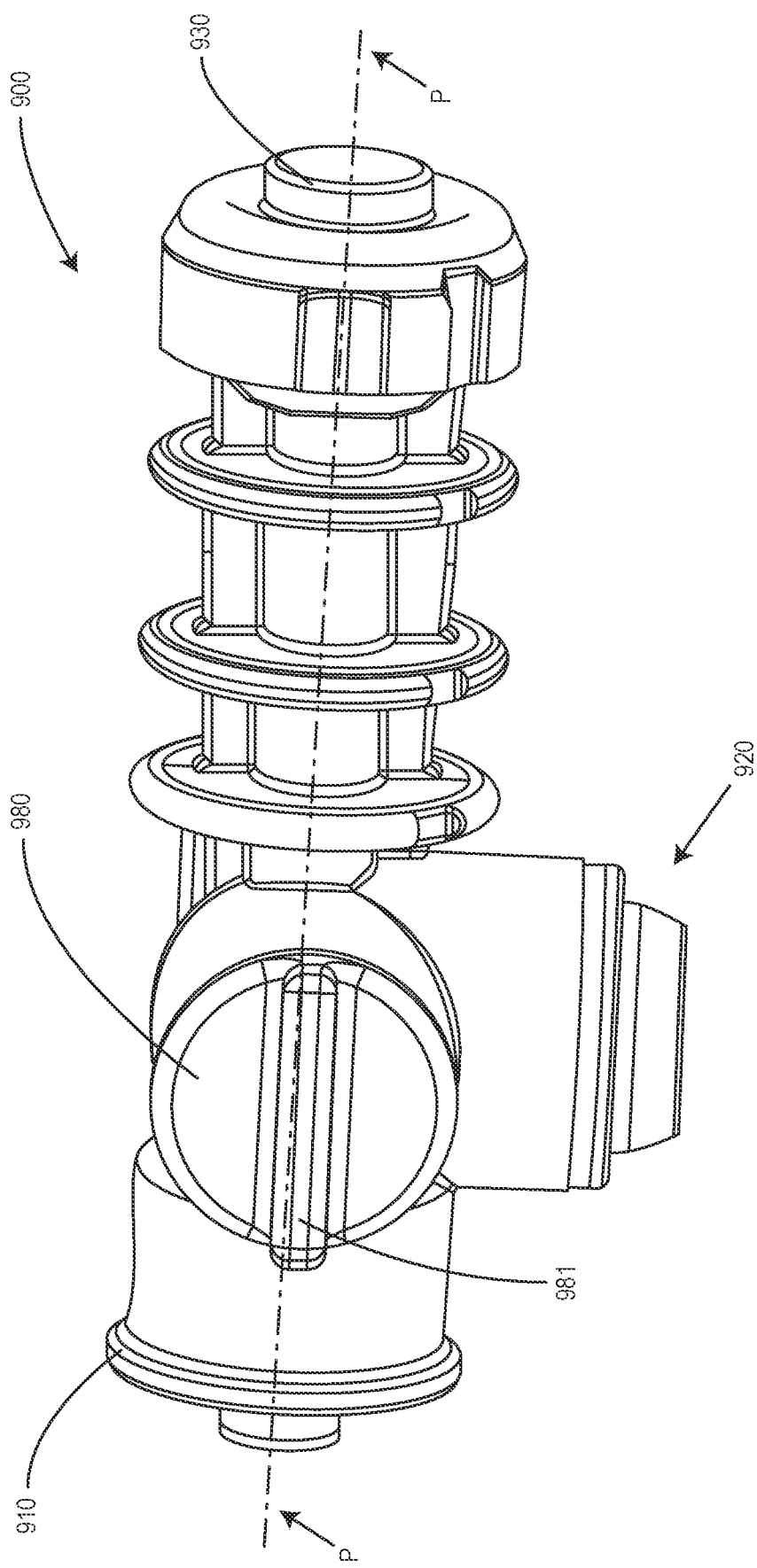
FIG. 13A is side perspective view of an adaptor according to a seventh example of the presently disclosed subject matter, illustrating an actuator configured to directly block a liquid channel thereof, the actuator in its first actuator state.

The adaptor 90 further includes an actuator 980 positioned partially in the liquid channel 926 so as to selective block the passage of liquid therethrough. The actuator 980 has a knob 981 that is configured to be held by a user to displace the actuator 980 between its first actuator state as shown in FIGS. 13A and 13B and a second actuator state as shown in FIGS. 13C and 13D.

Figure 13B:
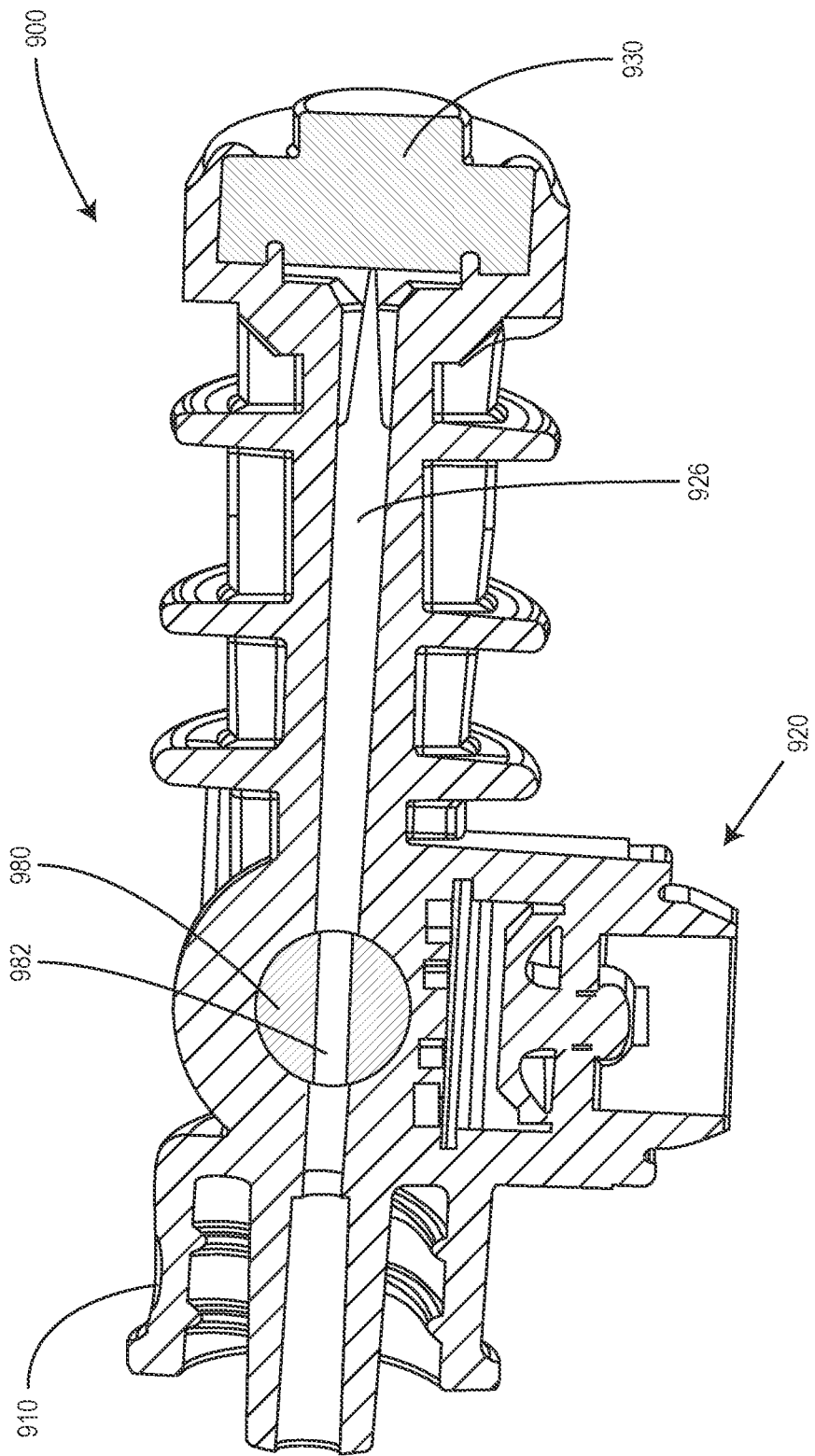
FIG. 13B is a cross-sectional view along line P-P in FIG. 13A.
Figure 13C:
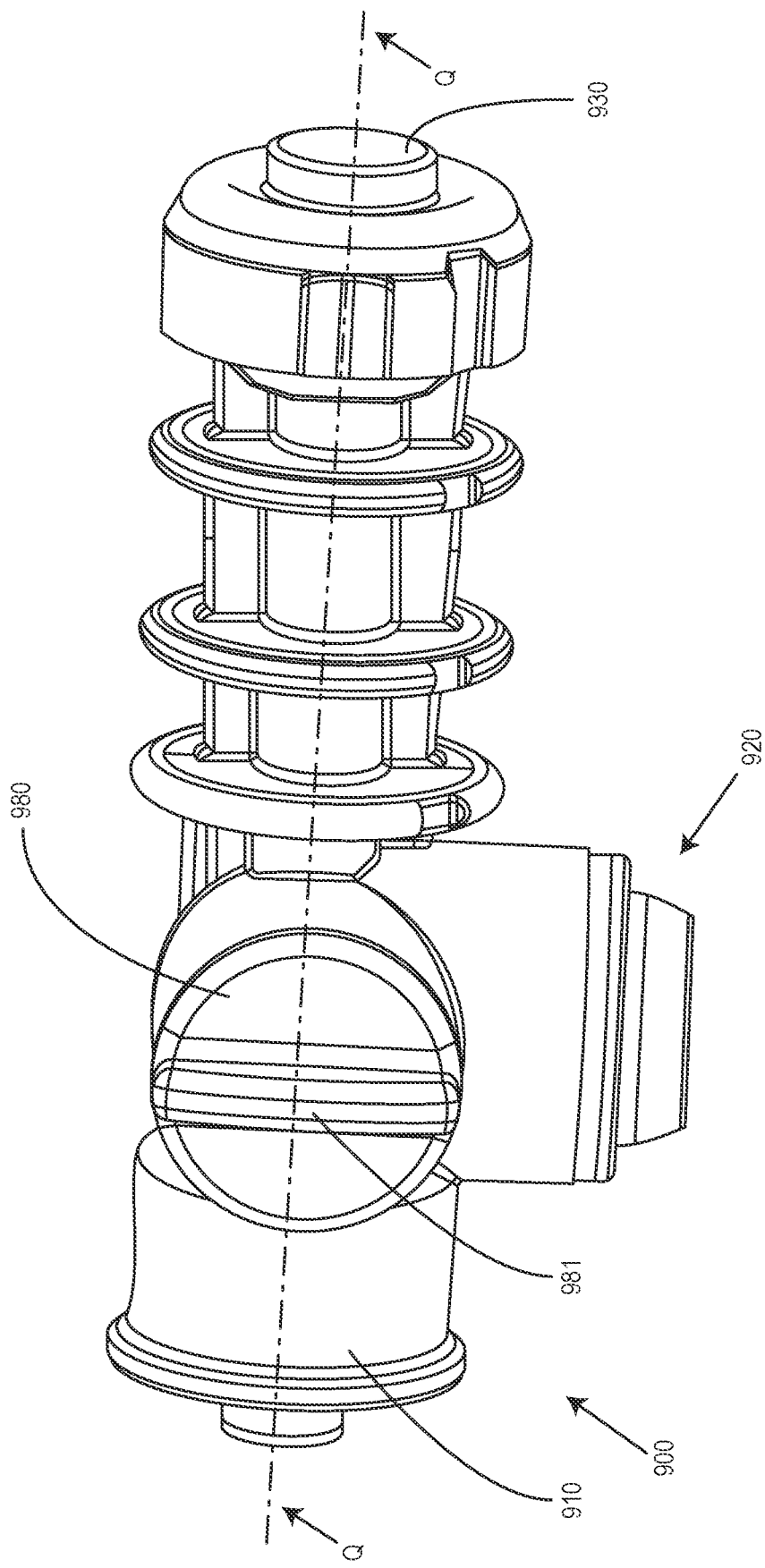
FIG. 13C is the same view as that of FIG. 13A illustrating the actuator in its second actuator state.
Figure 13D:
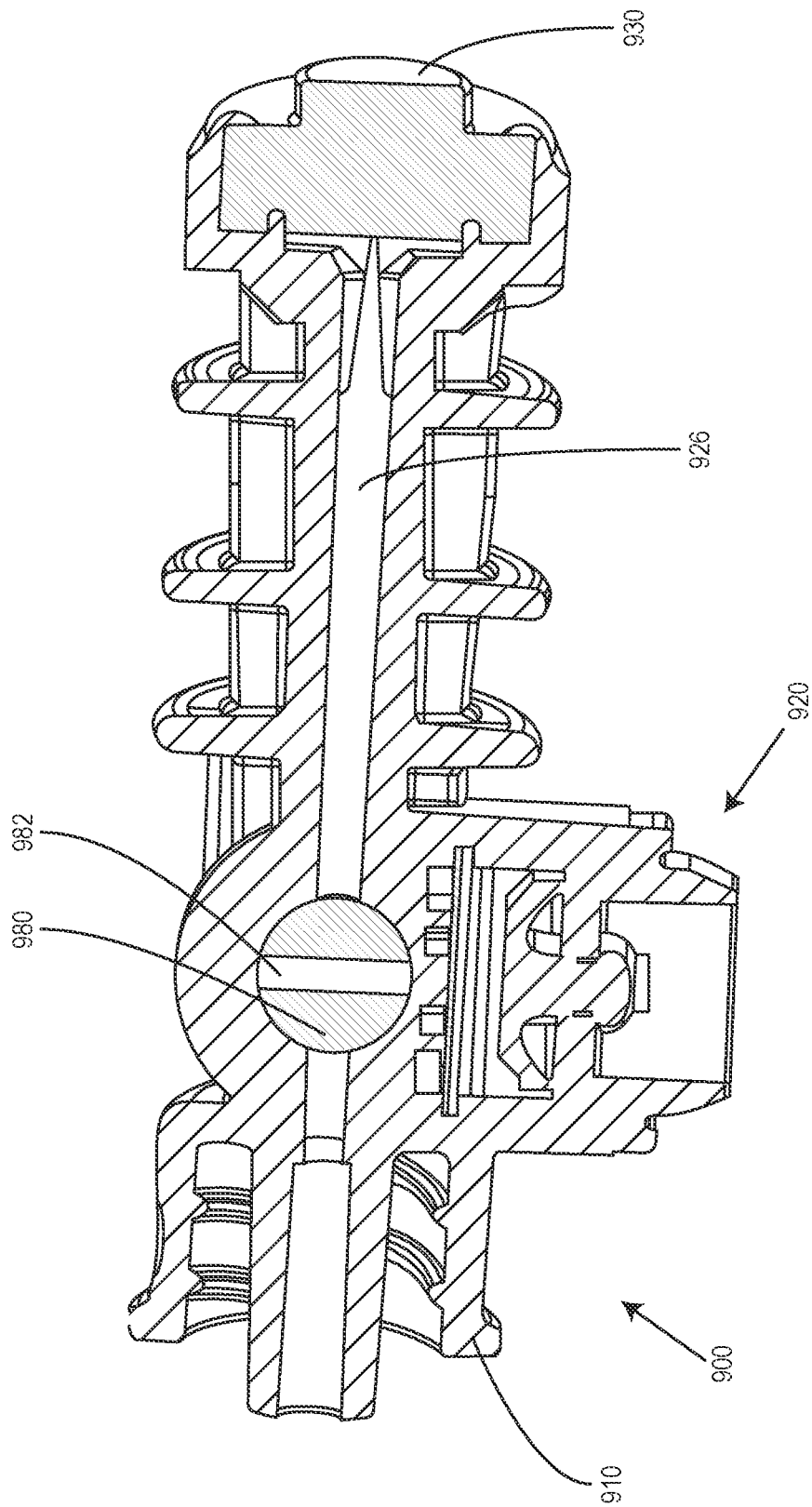
FIG. 13D is a cross-sectional view along line Q-Q in FIG. 13C.

As can be seen in FIGS. 13B and 13D, the actuator comprises a flow path 82, which in the first actuator state, shown in FIG. 13B is aligned with the liquid channel 926 to allow flow of liquid therethrough in both the directions, i.e., from the septum 930 to the connector 910 and vice versa, thus, at this actuator state, the adaptor 900 is at its fully operational state. In FIG. 13D, the actuator is in its second actuator state and the flow path 982 is not aligned with the liquid channel 926 thereby blocking the flow of the liquid therethrough in both the directions, thus, at this actuator state, the adaptor 900 is at its at least partial inoperational state. In the illustrated example, at the at least partial inopertional state, the adaptor is fully inoperable to facilitate the flow of liquid therethrough.

The actuator 980 is configured to be displaceable between the first and the second actuator state upon application of a force by a user, which in the illustrated example, is a rotational force. In some examples, the actuator can be displaceable between its states by a push/pull or a combination of a push/pull and rotation. In some examples, the actuator can be configured to be normally at one of its first and second state and to be displaced into the other state upon application of force and return automatically into the normal state upon removal of the force. In some examples, the actuator can be configured to independently retain both of its states in the absence of the force.

In the illustrated embodiment, the adaptor 900 is different from those described above, for instance, does not include an air channel unlike the luer lock adaptor 1 described above, and the adaptor 900 can be used with a syringe having only a liquid needle unlike the syringe 500 described above. However, in some examples, the actuator 980 can be used with any of the adaptors (luer lock adaptors as well as spike adaptors) described above while being positioned in the corresponding liquid channels of those adaptors without affecting the additional functioning of those adaptors.

In some examples (not shown), a no-return valve or a one-way valve can be positioned within the flow path of the actuator such that in the second actuator state, the flow of liquid through the liquid channel of the adaptor is blocked in one direction and allowed in the opposite direction.

The invention claimed is:

1. A connector for connection with a fluid transfer device, said connector comprising:
   an outer body having a longitudinal axis;

a luer lock connection port positioned within the outer body and configured to be coupled with an external port of said fluid transfer device, the luer lock connection port being rotatable about the longitudinal axis in a clockwise direction as well as a counter-clockwise direction at least prior to initiation of coupling thereof with the external port, wherein the outer body is structured, and the luer lock connection port is positioned therewithin, such that to prevent an operator to access, through the outer body, directly by fingertips an exterior of the luer lock connection port after the luer lock connection port has been coupled with the external port; and a decoupling facilitating mechanism configured to selectively assume a decoupling disabled state at which it allows rotation of the luer lock connection port about the longitudinal axis thereof at least in the counter-clockwise direction, and a decoupling enabled state at which it restricts the rotation of the luer lock connection port at least in the counter-clockwise direction so as to allow decoupling of the external port from the luer lock connection port.

2. The connector according to claim 1, wherein the luer lock connection port is rotatable about the longitudinal axis in both of the clockwise direction and the counter-clockwise direction upon coupling thereof with the external port.

3. The connector according to claim 1, further comprising a coupling facilitating mechanism configured to selectively assume a coupling enabled state at which it restricts the rotation of the luer lock connection port at least in the clockwise direction, and a coupling disabled state at which it allows the rotation of the luer lock connection port at least in the clockwise direction, wherein the coupling facilitating mechanism is configured to assume the coupling enabled state at least during the time when coupling of the luer lock connection port with the external port is under process, wherein the coupling facilitating mechanism, in its coupling enable state, is configured to allow rotation of the luer lock connection port about the longitudinal axis in a counter-clockwise direction, and wherein the coupling facilitating mechanism, in its coupling disable state, is configured to allow rotation of the luer lock connection port about the longitudinal axis in a counter-clockwise direction.

4. The connector according to claim 3, wherein the luer lock connection port is configured to axially displace along the longitudinal axis between a first position associated with the coupling disabled state, and a second position associated with the coupling enabled state.

5. The connector according to claim 4, wherein the luer lock connection port is configured to freely displace from the first position to the second position upon application of a pushing or pulling force by the external port during the coupling.

6. The connector according to claim 4, wherein the coupling facilitating mechanism comprises at least one locking member mounted on an external surface of the luer lock connection port and at least one arresting member mounted on an internal surface of the outer body, wherein at the second position, the locking member engages with the arresting member thereby restricting the rotation of the luer lock connection port at least in the clockwise direction, wherein at the first position, the locking member disengages from the arresting member.

7. The connector accord to claim 1, wherein the outer body comprises a sidewall with at least one opening formed therein and configured to be used in conjunction with said decoupling facilitating mechanism so as to provide access to an external surface of the luer lock connection port at least at said decoupling enabled state, wherein the decoupling facilitating mechanism comprises an actuator at least partially positioned in the opening, the actuator having an actuator internal surface facing the luer lock connection port and an opposite actuator external surface, the decoupling facilitating mechanism being configured to assume the decoupling enabled state upon application of a pressing force on the actuator, and the decoupling disabled state upon removal of said force.

8. The connector according to claim 7, wherein at the decoupling enabled state, a minimum distance between the longitudinal axis and the actuator external surface is lesser than a minimum distance between the longitudinal axis and an external surface of a rim of the opening.

9. The connector according to claim 7, wherein at the decoupling enabled state, at least a majority of the actuator external surface is positioned below an imaginary surface defined by a rim of the opening.

10. The connector according to claim 7, wherein the actuator has a first portion extending from the outer body, and a second portion extending from the first portion, wherein the first portion forms a part of the outer body, wherein the first portion and the second portion constitute a lever.

11. The connector according claim 7, wherein the decoupling mechanism comprises a first engaging portion constituting a part of an external surface of the luer lock connection port, and a second engaging portion constituting a part of the actuator internal surface, wherein at the decoupling enabled state, the first engaging portion engages with the second engaging portion thereby restricting the rotation of the luer lock connection port at least in the counter-clockwise direction wherein at the decoupling disabled state, the first engaging portion disengages from the second engaging portion.

12. The connector according to claim 11, wherein the first engaging portion comprises at least one protrusion formed on the external surface of the luer lock connection port, and the second engaging portion comprises at least one tooth projecting from the actuator internal surface, wherein at the decoupling enabled state, the at least one tooth engages with the at least one protrusion thereby restricting the rotation of the luer lock connection port at least in the counter-clockwise direction.

13. The connector according to claim 12, wherein the actuator is configured to be pressed only when the at least one protrusion is radially displaced with respect to the at least one tooth.

14. The connector according to claim 12, wherein the at least one protrusion has a protrusion side surface extending from the external surface of the luer lock connection port towards the actuator, and the at least one tooth has a tooth side surface extending from the actuator internal surface towards the luer lock connection port, wherein at the decoupling enabled state, the tooth side surface engages the protrusion side surface, wherein at the decoupling disabled state, the at least one tooth disengages from the at least one protrusion.

15. The connector according to claim 4, wherein the luer lock connection port is configured to axially displace along the longitudinal axis into a third position, wherein the third position is the first position, or any position between the first position and the second position or the second position is any position between the first position and the third position, or the first position is any position between the second and third position, wherein the luer lock connection port is configured to freely displace from the first or second position to the third position upon application of a pushing or pulling force during decoupling the external port from the luer lock connection port, wherein the decoupling facilitating mechanism is configured to assume the decoupling enabled state upon the luer lock connection port displacing into the second or third position.

16. The connector according to claim 1, wherein the luer lock connection port is a male luer lock connection port comprising an elongate central member and a collar surrounding the elongate central member, wherein the male luer lock connection port is configured to be coupled to the external port by threadingly receiving the external port between the collar and the elongate central member, such that upon coupling, the collar is positioned between the external port and the outer body.

17. The connector according to claim 16, wherein the collar extends parallel to the elongate central member, and a length of the collar ranges between 5.4 mm to 8 mm.

18. The connector according to claim 16, wherein the outer body covers at least a majority of the collar.

19. The connector according to claim 1, wherein the outer body radially covers at least a majority of a sidewall of the luer lock connection port.

20. An adaptor configured for use in medical fluid transfer devices, the adaptor comprising the connector according to claim 1, wherein the connector constitutes a proximal portion of the adaptor, wherein the adaptor comprises a septum positioned at a distal end thereof configured to receive at least one needle of a syringe therethrough.

* * * * *